US011173139B2

United States Patent
Cash

(10) Patent No.: US 11,173,139 B2
(45) Date of Patent: Nov. 16, 2021

(54) METHOD FOR EXTENDING LIFESPAN DELAYING THE ONSET OF AGE-RELATED DISEASE

(71) Applicant: Alan B. Cash, San Diego, CA (US)

(72) Inventor: Alan B. Cash, San Diego, CA (US)

(*) Notice: Subject to any disclaimer, the term of this patent is extended or adjusted under 35 U.S.C. 154(b) by 0 days.

(21) Appl. No.: 16/001,796

(22) Filed: Jun. 6, 2018

(65) Prior Publication Data

US 2019/0008816 A1  Jan. 10, 2019

Related U.S. Application Data

(63) Continuation of application No. 11/792,703, filed as application No. PCT/US2005/046130 on Dec. 15, 2005, now Pat. No. 10,016,385.

(60) Provisional application No. 60/637,287, filed on Dec. 17, 2004.

(51) Int. Cl.
| | |
|---|---|
| *A61K 31/22* | (2006.01) |
| *A23L 33/10* | (2016.01) |
| *A61K 31/194* | (2006.01) |
| *A61K 31/195* | (2006.01) |
| *A61K 45/06* | (2006.01) |

(52) U.S. Cl.
CPC .......... *A61K 31/22* (2013.01); *A23L 33/10* (2016.08); *A61K 31/194* (2013.01); *A61K 31/195* (2013.01); *A61K 45/06* (2013.01)

(58) Field of Classification Search
CPC ...... A61K 31/22; A61K 31/195; A61K 45/06; A61K 31/194; A23L 33/10
See application file for complete search history.

(56) References Cited

U.S. PATENT DOCUMENTS

| | | |
|---|---|---|
| 2,798,053 A | 7/1975 | Brown et al. |
| 4,573,996 A | 3/1986 | Kwiatek et al. |
| 4,597,961 A | 7/1986 | Etscorn |
| 4,839,174 A | 6/1989 | Baker et al. |
| 4,908,213 A | 3/1990 | Govil et al. |
| 4,943,435 A | 7/1990 | Baker et al. |
| 5,006,551 A | 4/1991 | Groke et al. |
| 5,183,674 A | 2/1993 | Olin |
| 5,328,454 A | 6/1994 | Sibalis |
| 5,336,168 A | 8/1994 | Sibalis |
| 5,474,527 A | 12/1995 | Bettinger |
| 5,676,969 A | 10/1997 | Wick et al. |
| 5,747,538 A | 5/1998 | Meybeck et al. |
| 10,016,385 B2 | 7/2018 | Cash |
| 2001/0049349 A1 | 12/2001 | Chinery et al. |
| 2002/0006910 A1 | 1/2002 | Miasnikov et al. |
| 2002/0031483 A1 | 3/2002 | Beck et al. |
| 2002/0107250 A1* | 8/2002 | Hariharan ............ A61K 31/351 514/247 |
| 2003/0039690 A1 | 2/2003 | Byrd |
| 2003/0176365 A1 | 9/2003 | Blass |

FOREIGN PATENT DOCUMENTS

| | | |
|---|---|---|
| EP | 0326826 A | 8/1989 |
| FR | 2730635 A | 8/1996 |
| WO | WO-99/55302 | 11/1999 |

OTHER PUBLICATIONS

Walpole et al. (BMC Public Health 2012, 12:439). (Year: 2012).*
Yamamoto et al., Toxicology Letters vol. 143, Issue 2, Jul. 20, 2003, pp. 115-122 (Year: 2003).*
Anderson, R.M. et al. (Dec. 19, 2003; e-published on Nov. 6, 2003). "Yeast Life-Span Extension by Calorie Restriction Is Independent of NAD Fluctuation" *Science* 302(5653):2124-2126.
Bauer, M. et al. (Feb. 3, 2004). "Starvation Response in Mouse Liver Shows Strong Correlation With Lifespan Prolonging Processes," *Physiological Genomics* 17(2):230-244.
Bertino, J.R. et al. (2000). "Principles of Cancer Therapy," Chapter 198 in *Cecil Textbook of Medicine*, 21$^{st}$ edition vol. 1, Goldman,L. ed., Bennett, J.C. ed., W.B. Saunders Company,Philadelphia, Pennsylvania, pp. 1060-1074.
Calabrese, P.R. et al. (Aug. 1977). "Lymphangiomyomatosis with Chylous Ascites-Treatment with Dietary Fat Restriction and Medium Chain Triglycerides," *Cancer* 40:895-897.
Cao, S.X. et al. (Sep. 11, 2001). "Genomic Profiling of Short-And Long-Term Caloric Restriction Effects in the Liver of Aging Mice," *Proc Natl Acad Sci* 98(19):10630-10635.
Cash, A. (2009). "Oxaloacetic Acid Supplementation as a Mimic of Calorie Restriction," *Open Longevity Science* 3:22-27.
Cash, A. (2013). "Use of the Metabolite "Oxaloacetate" for the Dietary Management of Parkinson's Disease," Poster, the Movement Disorders Program at UCLA, one page.
Cash, A.B. (2009). "Modification of the NAD+/NADH Ratio Via Oxaloacetic Acid Supplementation to Mimic Calorie Restriction Metabolic Pathways and Increase Lifespan," Chapter 6 in Anti-Aging Therapeutics, vol. XII, Dr. Ronald Klatz, ed. and Dr. Robert Goldman, ed., A4M Publications, Chicago, IL, pp. 43-51.

(Continued)

*Primary Examiner* — Kortney L. Klinkel
*Assistant Examiner* — William Y Lee
(74) *Attorney, Agent, or Firm* — Morrison & Foerster LLP

(57) ABSTRACT

A method and composition for extending the lifespan of an individual and delaying the onset of age-related disease is provided. The method includes the administration of an effective dose of oxaloacetate, wherein the oxaloacetate acts to mimic the cellular conditions obtained under caloric restriction to provide similar benefits. The invention further includes methods and compositions for reducing the incidence or treatment of cancer. Compositions and methods for reducing body fat by administering an effective amount of oxaloacetate are likewise provided. Compositions for DNA repair in UV damaged cells is provided are also provided. Similarly, a method for treating a hang-over comprising administering an effective amount of oxaloacetate is disclosed.

9 Claims, 9 Drawing Sheets

(56) References Cited

OTHER PUBLICATIONS

Champ, C.E. et al. (2013). "Nutrient Restriction and Radiation Therapy for Cancer Treatment: When Less Is More," *The Oncologist* 18:97-103.
Chany C., and Cerutti I. "Aspartate-Assisted Immune Stimulation: Its Importance in Antitumor and Antiviral Protection", International Journal of Cancer, 1986, vol. 38, No. 2, pp. 259-264, XP002524523.
Daitoku, H. et al. (Jul. 6, 2004). "Silent Information Regulator 2 Potentates Foxo1-Mediated Transcription Through Its Deacetylase Activity," *Proc Natl Acad Sci U.S.A.* 101(27):10042-10047.
Dunn, S.E. (1997). "Dietary Restriction Reduces Insulin-like Growth Factor Levels, Which Modulates Apoptosis, Cell Proliferation, and Tumor Progression in p53-deficient Mice," *Cancer Res.* 57:4667-4672.
Fernandes, G. et al. (Oct. 7, 1976). "Suppression of adenocarcinoma by the immunological consequences of calorie restriction," *Nature* 263:504-507.
First Examination Report by Government of India Patent Office dated Aug. 29, 2012.
Fontana, L. et al. (Apr. 27, 2004; e-published on Apr. 19, 2004). "Long-Term Calorie Restriction is Highly Effective in Reducing the Risk for Atherosclerosis in Humans," *PNAS* 101(17):6659-6663.
Giovanella et al. (Feb. 1982). "Calorie Restriction: Effect on Growth of Hunab Tumors Heterotransplanted in Nude Mice," *JNCI* 68(2):249-257.
Good, R.A. et al. (1990). "Experimental Approaches to Nutrition and Cancer: Fats, Calories, Vitamins and Minerals," *Med. Oncol. & Tumor Pharmacother* 7(⅔):183-192.
Guarente, L. (Jul. 1, 2001). "SIR2 and Aging—The Exception that Proves the Rule," *Trends Genet.* 17(7):391-392.
Guarente, L. (Nov. 18, 1999). "Mutant Mice Live Longer," *Nature* 402:243-245.
Hekimi, S. et al. (Feb. 28, 2003). "Genetics and the Specificity of the Aging Process," *Science* 299(5611):1351-1354.
Hipkiss, A.R. (Oct. 2010). "Proteotoxicity and the contrasting effects of oxaloacetate and glycerol on Caenorhabditis elegans life span: a role for methylglyoxal?" Rejuvenations Res. 13(5):547-551, one page, (Abstract only).
Howitz, K.T. et al. (Sep. 11, 2003). "Small Molecule Activators Of Sirtuins Extend *Saccharomyces cerevisiae* Lifespan," *Nature* 425:191-196.
Ido, Y. et al. (Jan. 13, 2004; e-published on Jan. 13, 2004). "NADH Augments Blood Flow in Physiologically Activated Retina and Visual Cortex," *PNAS* 101(2):653-658.
Jain R.M., et al. "Effect of Ketoacids on H0 Induced Cataraet", Indian Journal of Clinical Biochemistrv, 2003, vol. 18, No. 1, pp. 91-95, XP002524519.
Kaeberlein, M. et al. (Sep. 2004). "Sir2-Independent Life Span Extension by Calorie Restriction in Yeast," *PloS Biology* 2(9)e296:1381-1387.
Kahn, A.M. et al. (Mar. 2002). "Insulin Increases NADH/NAD$^+$ Redox State, Which Stimulates Guanylate Cyclase in Vascular Smooth Muscle," *American Journal of Hypertension* 15(3):273-279.
Karsegard V. L., et al. "L-Ornithine a-Ketoglutarate in HIV Infection: Effects on Muscle, Gastrointestinal, and Immune Functions", Nutrition, 2004, vol. 20, No. 6, pp. 515-552, XP002524520.
Kitani, K. et al. (1992). "Chronic Treatment of(-) Deprenyl Prolongs the Life Span of Male Fischer 344 Rats. Further Evidence," *Life Sciences* 52:281-288.
Kjellman U.W. et al. "Insulin (GIK) Improves Myocardial Metabolism in Patients During Blood Cardioplegia", Scandinavin Cardiovascular Journal, Scandinavian University Press, 2000, vol. 34, No. 3, pp. 321-330.
Koubova, J. et al. (Jan. 22, 2003). "How Does Calorie Restriction Work?," *Genes & Development* 17:313-321.
Lamming, D.W. et al. (Aug. 2004). "Small Molecules That Regulate Lifespan: Evidence For Xenohormesis," *Molecular Microbiology* 53(4):1003-1009.

Lane, M.A. et al. (1999). "Short-Term Calorie Restriction Improves Disease-Related Markers in Older Male Rhesus Monkeys (*Macaca mulatta*)," *Mechanisms of Ageing and Development* 112(3):185-196.
Lane, M.A. et al. (Jan. 1, 1999). "Nutritional Modulation of Aging in Nonhuman Primates," *The Journal of Nutrition, Health & Aging* 3(2):69-76.
Lebricon T., Cynober L. Field CJ, Baracos Ve "Supplemental Nutrition with Ornithine Alpha-Ketoglutarate in Rats with Cancer-Associated Cachexia—Surgical Treatment of the Tumor Improves Efficacy of Nutritional Support", 1995, vol. 125, XP002524517.
Lee, C.K. et al. (Apr. 15, 2004). "The Impact of α-Lipoic Acid, Coenzyme $Q_{10}$, and Caloric Restriction on Life Span and Gene Expression Patterns in Mice," *Free Radical Biology & Medicine* 36(8):1043-1057.
Licastro, F. et al. (Apr. 1988). "Effect Of Dietary Restriction Upon the Age-Associated Decline of Lymphocyte DNA Repair Activity in Mice," *Age* 11(2):48-52.
Lin, S.J. et al. (Jul. 18, 2002). "Calorie Restriction Extends *Saccharomyces cerevisiae* Lifespan by Increasing Respiration," *Nature* 418(6895):344-348.
Lin, S.J. et al. (Sep. 22, 2000). "Requirement of NAD and SIR2 for Life-Span Extension by Calorie Restriction in *Saccharomyces cerevisiae*," *Science* 289(5487):2126-2128.
Lipman, J.M. et al. (May 1989). "The Influence of Dietary Restriction on DNA Repair In Rodents: A Preliminary Study," *Mechanisms of Ageing and Development* 48(2):135-143.
Ludwig A. et al. "Effects of Various HTK Solution Regimens on Proteinuria After Renal Transplantation in Dogs", Urological Research, Springer Verlag, Berlin, DE, 1995, vol. 23, No. 5, pp. 351-360.
Macdonald, M.J. et al. (Mar. 2002). "Histochemical Evidence for Pathways Insulin Cells Use to Oxidize Glycolysis-Derived NADH," *Metabolism* 51(3):318-321.
Mai, V. (Apr. 25, 2002). "Even Moderate Caloric Restriction Lowers Cancer Risk in Mice," Federation of American Societies for Experimental Biology, Science Daily, 2 pages.
Mai, V. et al. (Apr. 15, 2003). "Calorie Restriction and Diet Composition Modulate Spontaneous Intestinal Tumorigenesis in $Apc^{Min}$ Mice through Different Mechanisms," *Cancer Research* 63:1752-1755.
Masternak, M.M. et. al. (Aug. 1, 2004). "Divergent Effects of Caloric Restriction on Gene Expression in Normal and Long-Lived Mice," *Journal of Gerontology: Biological Sciences* 59A(8):784-788.
Matsuzaki, J. et al. (2000). "Implanted Tumor Growth Is Suppressed and Survival Is Prolonged in Sixty Percent of Food-Restricted Mice," *The Journal of Nutrition* 130:111-115.
Picard, F. et al. (Jun. 17, 2004; e-published on Jun. 2, 2004). "Sirt1 Promotes Fat Mobilization in White Adipocytes by Repressing PPAR-γ," *Nature* 429(6993):771-776.
Pistell, P.J. et al. (Oct. 13-17, 2012). "Evaluating Two Novel Calorie Restriction Mimetics for Treating Alzheimer's Disease," Poster, presented at Society for Neuroscience Annual Meeting, New Orleans, LA, one page.
Riedel, E.E. et al. (Jan. 1, 1996). "α-Ketoglutarate application in hemodialysis patients improves amino acid metabolism," *Nephron, Switzerland* 74:261-265, XP009094145.
Roth et al. (2000). "Caloric Restriction in Primates and Relevance to Humans," *Annals of the New York Academy of Sciences* pp. 305-315.
Roth, G.S. et al. (2016). "Manipulation of health span and function by dietary caloric restriction mimetics," *Annals of the New York Academy of Sciences* 1363:5-10.
Sheldon, W.G. et al. (1995). "Age-Related Neoplasia in a Lifetime Study of Ad Libitum-Fed and Food-Restricted B6C3F1 Mice," *Toxicologic Pathology* 23(4):458-476.
Siegel I. et al. (1988). "Effects of Short-Term Dietary Restriction on Survival of Mammary Ascites Tumor-Bearing Rats," *Cancer Investigations* 6(6):677-680.
Spindler, S.R., "Caloric Restriction Enhances the Expression of Key Metabolic Enzymes Associated With Protein Renewal During Aging," Annals of the New York Academy of Sciences, New York, NY, US, vol. 928, Jan. 1, 2000, pp. 296-304 XP002961486.

(56) References Cited

OTHER PUBLICATIONS

Srivastava, V.K. et al. (Jan. 31, 1992). "Decreased Fidelity Of DNA Polymerases And Decreased DNA Excision Repair In Aging Mice: Effects Of Caloric Restriction," *Biochemical and Biophysical Research Communications* 182(2):712-721.

Sugie, S. et al. (1993). "Effect of restricted caloric intake on the development of the azoxymethane-induced glutathione S-transferase placental form positive heptatocellular foci in male F344 rats," *Cancer Letters* 68:67-73.

Tilley, R. et al. (Apr. 1992). "Enhanced Unscheduled DNA Synthesis By Secondary Cultures of Lung Cells Established From Calorically Restricted Aged Rats," *Mechanisms of Ageing and Development* 63(2):165-176.

Tissenbaum, H.A. et al. (Mar. 8, 2001). "Increased Dosage of a Sir-2 Gene Extends Lifespan In *Caenorhabditis elegans*," *Nature* 410(6825):227-230.

Varma S. D. et al. Formation of Advanced Glycation end (AGE) Products in Diabetes: Prevention by Pyruvate and α-keto Glutarate, Molecular and Cellular Biochemistry, 1997, vol. 171, pp. 23-28, XP002903871.

Weinberg J. M. et al. "Anaerobic and Aerobic Pathways for Salvage of Proximal Tubules from Hypoxia-Induced Mitochondrial Injury", American Journal of Physiology—Renal Physiology, 2000, vol. 279, No. 5 48-5, pp. F927-F943, XP002524518.

Weindruch, R. et al. (Mar. 12, 1982). "Dietary restriction in mice beginning at 1 year of age: effect on life-span and spontaneous cancer incidence," *Science* 215(4538):1415-1418.

Weraarchakul, N.L et al. (Mar. 1989). "The Effect of Aging and Dietary Restriction on DNA Repair," *Experimental Cell Research* 181(1):197-204.

Wood J.P.M. et al. (Oct. 1, 2003). "Zinc and Energy Reguirements in Induction of Oxidative Stress to Retinal Pigmented Epithelial Cells", Neurochemical Research, 28(10):1525-1533.

Wood, J.G. et al. (Aug. 5, 2004; e-published on Jul. 14, 2004). "Sirtuin Activators Mimic Caloric Restriction and Delay Ageing in Metazoans," *Nature* 430:686-689.

Wood, J.G. et al. (Sep. 3, 2004). "Sirtuin Activators Mimic Caloric Restriction and Delay Ageing in Metazoans," *Nature (Addendum)* 431:107, (one page).

Yamamoto H.-A. et al. "Effect of α-ketoglutarate and Oxaloacetate on Brain Mitochondrial DNA Damage and Seizures Induced by Kainic Acid in Mice" Toxicology Letters, 2003, vol. 143, No. 2, pp. 115-122, XP002524522.

Yoshikawa K. "Studies on Anti-diabetic Effect of Sodium Oxaloacetate", Tohoku Journal of Experimental Medicine, 1968, vol. 96(2) pp. 127-141.

Zhu, P. et al. (Feb. 5, 1991). "Effect of dietary calorie and fat restriction on mammary tumor growth and hepatic as well as tumor glutathione in rats," *Cancer Letters* 57:145-152.

European Search Report dated Jun. 2, 2009 for European Application 05854787.8.

Wilkins, H.M. et al. (Apr. 2016). "Oxaloacetate Enhances Neuronal Cell Bioenergetic Fluxes and Infrastructure," J. Neurochem. 137(1):76-87, 26 pages.

Fahn, S. et al. (Dec. 9, 2004). "Levodopa and The Progression of Parkinson's Disease," *The New England Journal of Medicine* 351(24):2498-2508.

Floyd, R.A. (Dec. 1999). "Antioxidants, Oxidative Stress, and Degenerative Neurological Disorders," Exp Biol Med. 222(3):236-245.

Gorelick, G. (Aug. 6, 2013). "Recurrent Stage 4 Glioblastoma Multiforme-Effect of Gliaxal Medical Food and Chemotherapy," Case Study, four pages.

Heilbronn, L.K. et al. (Sep. 2003). "Calorie Restriction and Aging: Review Of The Literature and Implications For Studies In Humans," Am J Clin Nutr 78(3):361-369.

Hristozov, D. et al. (2001). "Evaluation of Oxidative Stress in Patients with Cancer," Archives of Physiology and Biochemistry 109(4):331-336.

Kalous, M. et al. (1996). The Role Of Mitochondria In Aging, Physiol Res. 45(5):351-359. (Abstract only).

Lamson, D.W. et al. (1999). "Antioxidants In Cancer Therapy; Their Actions an Interactions With Oncologic Therapies," Alternative Medicine Review 4(5):304-329.

Mahoney, B.P. et al. (2003). "Tumor Acidity, Ion Trapping and Chemotherapeutics I. Acid pH Affects the Distribution of Chemotherapeutic Agents in Vitro," Biochemical Pharmacology 66:1207-1218.

Marty, M. et al. (Jul. 1, 2005). "Randomized Phase II Trial of the Efficacy and Safety of Trastuzumab Combined With Docetaxel in Patients With Human Epidermal Growth Factor Receptor 2—Positive Metastatic Breast Cancer Administered As First-Line Treatment: the M77001 Study Group," J. Clin. Oncology 23(19):4265-4274.

Maswood, N. et al. (Dec. 28, 2004). "Caloric Restriction Increases Neurotrophic Factor Levels and Attenuates Neurochemical and Behavioral Deficits in a Primate Model of Parkinson's Disease," 101(52):18171-18176.

Mattison, J.A. et al. (Sep. 13, 2012). "Impact Of Caloric Restriction On Health And Survival In Rhesus Monkeys From The NIA Study," Nature 489:318-321.

Portero-Otin, M. et al. (2004, e-pub. Sep. 7, 2004). "Protein Nonenzymatic Modifications and Proteasome Activity In Skeletal Muscle From The Short-Lived Rat and Long-Lived Pigeon," Experimental Gerontology 39:1527-1535.

Robertson, J.M.C.D. et al. (Dec. 1989). "Vitamin E Intake and Risk of Cataracts in Humans," Annals of the New York Academy of Sciences 570:372-382.

Rogers, S.L. et al. (Jan. 1998). "A 24-Week, Double-Blind, Placebo-Controlled Trial of Donepezil in Patients with Alzheimer's Disease," Neurology 50(1):136-145, 1 page (Abstract Only).

Roth, G.S. et al. (Jan. 1, 2000). "Effects Of Reduced Energy Intake On The Biology Of Aging: The Primate Model," European Journal of Clinical Nutrition, 54(Supp. 3):S15-S20.

Wang, J. et al. (Apr. 2005). "Caloric Restriction Attenuates β-Amyloid Neuropathology in a Mouse Model of Alzheimer's Disease," The FASEB Journal 19(6):659-661, 18 pages.

Yatin, S.M. et al. (2000). "Vitamin E Prevents Alzheimer's Amyloid β-Peptide (1-42)-Induced Neuronal Protein Oxidation and Reactive Oxygen Species Production," Journal of Alzheimer's Disease 2:123-131.

Zhou, Z. et al. (Sep. 2003). "A Critical Involvement of Oxidative Stress in Acute Alcohol-Induced Hepatic TNF-α Production," American Journal of Pathology 163(3):1137-1146.

\* cited by examiner

METHOD FOR EXTENDING LIFESPAN DELAYING THE ONSET OF AGE-RELATED DISEASE

CROSS REFERENCE TO RELATED APPLICATIONS

This application is a continuation of U.S. patent application Ser. No. 11/792,703, filed May 13, 2008, which is a National Phase Application under 35 U.S.C. § 371 of International Application No. PCT/US2005/46130, filed Dec. 15, 2005, which claims priority benefit to U.S. Provisional Application No. 60/637,287, filed Dec. 17, 2004, the disclosures of each of which are herein incorporated by reference in their entirety.

BACKGROUND OF THE INVENTION

Field of the Invention

The present invention pertains to a method of extending life span in organisms and delays the onset and many of the complications associated with age-related diseases, including cancer. More particularly, the invention relates to the administration of a chemical agent to upregulate and down-regulate the expression (i.e. gene activation) of the same beneficial genes that are activated in caloric restriction. The genes are activated by mimicking the same intracellular conditions as are seen in caloric restriction, but without the need to reduce caloric intake. Compositions and methods to prolong life and protect an organism from age-related diseases are likewise provided.

Description of the Related Art

Many attempts have been made to extend life span in single cell organisms and multi-cellular animals. These attempts have included various nutritionally-based interventions, vitamin supplements, antioxidant supplements, exercise, hormonal, pharmaceutical and other paradigms (Lane, M. et al. Nutritional Modulation of aging in nonhuman primates, 1999 The Journal of Nutrition, Health & Aging, Vol. 3, No. 2 pp 69-76). While these attempts sometimes result in better health, in the last 70 years, only activation of beneficial genes has caused an increase in lifespan. Three methods of beneficial gene activation have been proven to extend mean and maximal lifespan: 1) gene activation by calorie restriction (CR); 2) certain types of animals receiving genetic engineering (the artificial addition or deletion of genes); and 3) the use of chemicals that activate the Sir2 gene by lowering the Michaelis constants, $K_m$, of the Sir-2 enzymes for the co-substrate NAD+[24]. CR is the limitation of total calories derived from carbohydrates, fats, or proteins to a level 25% to 60% below that of control animals fed ad libitum (Koubova et al, How does calorie restriction work? 2003 Genes & Development. Vol. 17 pp 212-221). Success in extending lifespan with gene activation by CR includes a wide range of different organisms including yeast, rotifers, guppies, spiders, fruit flies, hamsters, rats, mice and it is now indicated at extending lifespan in primates (Lane et al.; Koubova et al.; Lane et al, Short-term calorie restriction improves disease-related markers in older male rhesus monkeys (*Macaca mulatta*) 1999 Mechanisms of Ageing and Development Vol. 112 pp 185-196). Success in extending lifespan with genetic engineering has been successful in yeast, worms, fruit flies and mice (Hekimi, S. et al, Genetics and the Specificity of the Aging Process, Science. 2003 Feb. 28; 299(5611):1351-4. Review; Guarente, L. SIR2 and aging—the exception that proves the rule, Trends Genet. 2001 July; 17(7):391-2; Tissenbaum, H et al. Increased dosage of a sir-2 gene extends lifespan in *Caenorhabditis elegans,* 2001 Nature Vol 410 pp 227-230; Lin, S et al, Requirement of NAD and SIR2 for Life-Span Extension by Calorie Restriction in *Saccharomyces cerevisiae* 2000 Science Vol. 289 pp 294-297; Lin, S et al, Calorie restriction extends *Saccharomyces cerevisiae* lifespan by increasing respiration 2002 Nature, Vol. 110 pp 244-248; Guarente, L. Mutant mice live longer, 1999 Nature Vol. 402 pp 243-245). Success in extending lifespan with chemicals that lower the Michaelis constant of the Sir-2 enzymes for NAD has been shown in yeast and worms (Howitz et al., Small molecule activators of sirtuins extend *Saccharomyces cerevisiae* lifespan, Nature 425: 191-196; Wood et al., Sirtuin activators mimic caloric restriction and delay ageing in metazoans, Nature, Volume 430, 5 Aug. 2004. In all cases, expansion of lifespan required the activation of beneficial genes.

It is significant that CR works on such a wide range of organisms, from the single celled to very complex (including primates). The wide range of success of CR indicates that the process of life extension is based on the effects within the individual cells of the organisms, and that the process allowing life span extension is preserved across species. In rodents, the extension in life span can approach 50% (Koubova et al.). This lifespan comes at a price, however, as the organism needs to be fed at least 25% less calories than it would normally consume.

The benefits of CR are numerous. In addition to lifespan extension, the onsets of aging-related diseases are also delayed, leading to a healthier organism for a longer time. In mammals, CR delays all kidney disease, autoimmune disease, and diabetes. CR reduces age associated neuron loss in mouse models of Parkinson's disease and Alzheimer's disease (Koubova et al.). It is also noted that even moderate CR lowers cancer risk in mammals (Mai, V. Even Moderate Caloric Restriction Lowers Cancer Risk in Mice, Experimental Biology Conference 2002 Apr. 23 meeting). Additionally, CR mammals have been observed to have less body fat (Picard, et al., Sirt1 promotes fat mobilization in white adipocytes by repressing ppar gama, Nature, Vol. 429, 17 Jun. 2004.). CR has been shown to enhance the repair of DNA in skin and other tissues after exposure to ultraviolet light (Lipman et al, "The influence of dietary restriction on DNA repair in rodents: a preliminary study", Mech Ageing Dev 1989: 48: 135-43; Weraarchakul et al, "The effect of aging and dietary restriction on DNA repair", Exp Cell Res 1989; 181:197-204; Licastro et al, "Effect of dietary restriction upon the age-associated decline of lymphocyte DNA repair activity in mice", Age 1988: 11: 48-52; Srivastava et al, "Decreased fidelity of DNA polymerases and decreased DNA excision repair in aging mice: Effects of caloric restriction", Biochem Biophys Res Commun 1992: 182: 712-21; Tilley et al, "Enhanced unscheduled DNA synthesis by secondary cultures of lung cells established from calorically restricted aged rats", Mech Ageing Dev 1992: 63" 165-76). DNA repair is critical for skin repair and to prevent skin aging. It also reduces skin cancer incidence. Studies of humans undergoing CR for 3 to 15 years have shown reduced risk for atherosclerosis along with reductions in fasting glucose, fasting insulin, Hs-CRP levels, systolic and diastolic blood pressure, triglycerides, total cholesterol, and LDL cholesterol as compared to equivalent age-matched controls (Fontana, et al, "Long-term calorie restriction is highly effective in reducing the risk for atherosclerosis in humans, PNAS, Apr. 27, 2004, Vol. 101, no. 17, pp 6659-6663).

The benefits of CR are not due to dietary antioxidants, as single agents or combinations of antioxidants do not produce an increase in lifespan or delay tumorigenesis and other age related disease. Instead, CR works due to signaling changes that activate gene expression that reduce cellular proliferation or increase apoptosis. Multiple genes involved in the electron transport chain, immune response, protein turnover and protein synthesis are changed in CR (Lee, et al., The impact of α-Lipoic Acid, Coenzyme Q10, and Caloric Restriction on Life Span and Gene Expression Patterns in Mice, Free Radical Biology & Medicine, Vol. 36, No. 8, pp. 1043-1057, 2004). Masternak et al shows that genes related to insulin and insulin growth factor 1 (IGF1) are altered including PPARα, a gene suggested to play an important role in metabolic control and the accumulation and preservation of fat storage cells. (Masternak, et. al., Divergent Effects of Caloric Restriction on Gene Expression in Normal and Long-Lived Mice, Journal of Genontology, 2004, Vol. 59A, No. 8, 784-788). The activity of FOXO genes have also been shown to change under caloric restriction (Daitoku, et al., Silent information regulator 2 potentates Foxo1-mediated transcription through its deacetylase activity, PNAS, Jul. 6, 2004).

Within the last decade, it has been determined that the Silenced Information Regulator 2 (Sir2) gene in yeast and worms (Sir2.1 in worms, SIRT1 in humans) is also one of the genes that regulates lifespan and is activated in CR. Mutant worms and yeast with extra copies of Sir2 or Sir2.1 live longer, while mutations in the Sir2 gene severely reduce lifespan. See, e.g. Tissenbaum et al. Other animals contain similar genes or homologues to the Sir2 gene, including humans (the SIRT1 gene). CR creates a set of conditions in the cell that signals the activation of beneficial genes to lengthen lifespan and delay the onset of age-related disease. The activation of Sir2 by CR is one pathway to increased lifespan. CR also stimulates other genes that increase lifespan independent of Sir2 in a parallel pathway. Kaeberlein et al, "Sir2-Independent Life Span Extension by Calorie Restriction in Yeast" 2004, PloS Biology: 2: 9: e296: 1381-1387

It has been shown that activation of Sir2 can activate or silence other genes and proteins, including FOXO type genes. Also, the activation of the Sir2 gene (SIRT1 in humans) normally turned on in CR blunted the protein PPAR gamma that activated fat-storage genes, so that fat cells would shed fat and prevented cells from differentiating into fat cells. See, e.g. Picard et al. supra. This would explain the low amounts of fat seen in mammals under CR.

Lin et al. determined that the internal cellular signaling condition generated by CR to activate beneficial genes is the increase in NAD+/NADH (oxidized and reduced nicotinamide adenine dinucleotide) ratios within the cell as compared to non-CR conditions. Lin, S. et al, Calorie restriction extends yeast life span by lowering the level of NADH. 2004 Genes & Development Vol. 18 pp 12-16. Lin also noted that NAD+ levels in cells remain constant between CR and non-CR conditions, while the reduced form of NAD+, NADH, is significantly lowered in CR (up to 50%), which allows activation of at least one beneficial gene, the Sir2 type gene. High levels of NADH are an inhibitor of the Sir2 gene.

Lin's study showed at least one of the intracellular requirements for signaling the activation of beneficial genes resulting in increased longevity and health benefits found during CR. The study used recombinant genetic modifications to achieve the increase the ratio of NAD+/NADH, (without the restriction in calories) and thereby "mimic" caloric restriction results of increased lifespan and general improvement in health. The important characteristic shown was that calories did not have to be reduced, but rather that beneficial genes need to be activated within the individual cells in order to achieve the same benefits of CR.

In other studies by Horitz, Wood and Lamming, researchers have discovered an alternate pathway for increasing life span that is distinct from CR and genetic engineering to increase the NAD+/NADH ratio to stimulate at least one beneficial gene. Instead of inserting genes to modify the NAD+/NADH ratio or to add additional copies of a beneficial gene by genetic engineering, they instead used chemical agents to lower the substrate-binding affinity between NAD+ and Sir2 allowing the Sir2 (SIRT1 in humans) to activate more readily. Howitz et al., Small molecule activators of sirtuins extend *Saccharomyces cerevisiae* lifespan, Nature 425: 191-196; Wood et al., Sirtuin activators mimic caloric restriction and delay ageing in metazoans, Nature, Volume 430, 5 Aug. 2004; Lamming et al., Small molecules that regulate lifespan: evidence for xenohonnesis, Molecular Microbiology, 2004, Vol. 53(4), 1003-1009. The chemical agents discovered are polyphenols and include the compound resveratrol. The polyphenols are found in plants, but are not part of the natural chemical makeup of mammals including humans. The polyphenols are very specific in the activation of the Sir2 gene and its homologues. The Sir2 gene extends lifespan, but does not activate all of the beneficial genes activated by CR. As a result of this, the Sir2 activating polyphenols produce a lower increase in lifespan extension than does CR. Kaeberlein et al, "Sir2-Independent Life Span Extension by Calorie Restriction in Yeast" 2004, PloS Biology: 2: 9: e296: 1381-1387.

Changing the inter-cellular binding potential with chemical agents or using genetic engineering to increase lifespan, reduce fat accumulation, and delay cancer and age related disease and improve overall health is a marvelous achievement. As a caution, however, genetic engineering is hardly a well-understood field, and is unlikely to help increase the lifespan of humans any time in the near future. Using chemical agents to lower the binding affinity of certain enzymes in order to stimulate Sir2 or Sirt1 (in humans) is also an uncertain path, as there is no long-term determination of risks. Additionally, the Sir2 or Sirt1 gene is only one of the genes that can be activated to increase lifespan, and produces a modest increase, whereas activation of more beneficial genes can result in longer increases in in lifespan. Finally, what if the application of the foreign chemicals such as Resveratrol cause harm in some isolated area of the human body?

The only long-term studies performed to extend lifespan, reduce body fat and delay cancer and other age-related conditions focused on actual caloric restriction. The studies, done since the 1930's, have shown the many benefits of caloric restriction, with the only noted potential disadvantages being that organisms took longer before they were of age to reproduce, and the organisms tended to be smaller than non-calorie restricted organisms.

We have been taught that the intercellular conditions seen in CR to activate beneficial genes include an increase in the NAD+/NADH ratio, which acts as a switching mechanism for the cell. To lower overall risk, it would be better to stimulate the same set of beneficial genes seen in CR by using the identical signaling method for the genes involved with CR. It would be beneficial to activate other life-extending genes in addition to or besides the Sir2 gene. Moreover, it would be of great benefit to find chemical agents that increase the NAD+/NADH ratio. Chemical agents that increase NAD+/NADH could provide a proven safe pathway (70 years of research) for lifespan expansion and the delay in the onset of age-related diseases. It would also be beneficial if the activation agent to increase the NAD+/NADH ratio was a chemical that is already found in mammals including humans, rather than introducing foreign compounds with unknown long-term results.

Due to the wide variety of chemical reactions available to the cell, each cell reacts in a manner to conserve the NAD+/NADH ratio. It is, in effect, a buffered response. It is especially difficult to increase the ratio. However, ethanol can decrease the NAD+/NADH ratio, which results in higher triglycerides and "fatty liver" disease.

Finding a compound to increase the NAD+/NADH ratio to activate beneficial genes is not trivial. One reason for this is due to the difficulty in directly measuring the NAD+/NADH ratio with current technology. Instead of measuring NAD+/NADH directly, the ratio is inferred indirectly by the measurement of the pyruvate/lactate ratio. Typically, when the amount of pyruvate to lactate increases, NAD+/NADH increases.

Thus, one method of increasing the NAD+/NADH ratio in the cells would be to increase the amount of pyruvate into the cell. In gluconeogenesis, pyruvate can be converted to glucose and converts a NADH to NAD+, which will increase the NAD+/NADH ratio. Also, under anaerobic conditions, pyruvate is converted to lactate by the enzyme lactate dehydrogenase. The conversion of pyruvate to lactate under anaerobic conditions again converts a NADH to NAD+. There are reports of an increase in the NAD+/NADH ratio with the injection of pyruvate into rats. Work done by Ido on the study of blood flow in the retina and visual cortex show that NADH levels in the cytosol can be dropped by 50%, doubling the NAD+/NADH ratio. Ido, et al, NADH augments blood flow in physiologically activated retina and visual cortex, PNAS, Jan. 13, 2004, Vol. 101, no. 2 pp 653-658. Despite this reported temporary change in the ratio, no extension of lifespan occurs with pyruvate because pyruvate also penetrates the inner mitochondrial membrane and preferentially engages in lowering the NAD+/NADH ratio through the Citric Acid Cycle. The ratio, temporarily raised by pyruvate, is then lowered when the pyruvate is processed through the Citric Acid Cycle. The typical cell buffers against increases in the NAD+/NADH ratio.

Anderson, et al. also had difficulty in using chemical agents to increase the NAD+/NADH ratio and activate beneficial genes. Anderson used acetaldehyde, known to reduce NADH in cells, but did not see any increase in the activity of beneficial genes. There is also some debate that changing the NAD+/NADH ratio will activate beneficial genes at all. Based on his work, Anderson teaches, "variations in NADH are unlikely to affect the activity of Sir2 or SIRT1" (beneficial genes) Anderson et al., Yeast Life-Span Extension by Calorie Restriction Is Independent of NAD Fluct . . . , Science 2003 302: 2124-2126.

There is a current need to create intracellular conditions similar to CR (i.e. increase of the NAD+/NADH ratio) with a Caloric Restriction "mimic" chemical that would allow beneficial genes to be implemented. Thus, the benefits of increased lifespan, lower cancer rates, lower body fat content and the delay in age-related disease without the heavy restrictions of diet imposed by CR or by genetic modification of the individual organism can be realized. The preference would be to have the chemical agents be currently part of human metabolism. The present invention provides such a chemical and method for the novel activation of beneficial genes.

SUMMARY OF THE INVENTION

The disclosure of the invention relates to methods and compositions for extending the lifespan and delaying the onset of age-related disease in an individual in need thereof. In one aspect of the invention, a method for extending the lifespan of an organism is provided. The method includes administering an effective amount of a compound such as oxaloacetate, oxaloacetic acid, an oxaloacetate salt, or its metabolic precursors alpha-ketoglutarate or aspartate. The compound can be administered orally, topically, and/or parenterally. Advantageously, the compound is formulated with a buffer. Optionally, the organism is a mammal. In one aspect of the invention, the mammal is a human.

In another aspect of the invention, a method of mimicking the beneficial health effect of caloric restriction without reducing caloric intake is described, wherein the method includes administering an effective amount of oxaloacetate, oxaloacetic acid, or an oxaloacetate salt. The beneficial health effect of caloric restriction can include weight loss, improvement of cardiac function, reversal of diabetes, and extension of life span. Advantageously, the compound is formulated for oral, parenteral, or topical administration. In a further aspect of the invention, the compound can include a buffer. Optionally, the method can include the step of administering a therapeutic agent such as an antibacterial, an antifungal, a chemotherapeutic agent, an anti-histamine, protein, enzyme, hormone, non-steroidal anti-inflammatory, an immuno-stimulatory compound, or a steroid. The therapeutic agent can be administered separately from the compound or substantially contemporaneously with the compound.

In another aspect of the invention, a composition for treating symptoms of skin aging is described. The composition can include an effective amount of oxaloacetate, oxaloacetic acid, an oxaloaceate salt, alpha-ketoglutarate, or aspartate, and a pharmaceutically effective carrier. Advantageously, the pharmaceutically effective carrier can be a cream, a soap, a shampoo, a conditioner, an ointment, a lotion, a gel, a salve, or an aerosol spray. Optionally, the composition can include a second beneficial agent such as an emollient, sunscreen, moisturizer, and/or buffer. The composition can be useful in treating symptoms of skin aging such as rhytids, wrinkles, jowls, sun damage, dull appearance of skin, loss of skin taughtness, keratosis, hyperpigmentation, melasma, and skin discoloration. The composition can further include a lipophilic agent, wherein the lipophilic agent acts to modify the rate of absorption of the composition.

A method for reducing the signs of skin aging is likewise provided. The method includes topically administering an effective amount of oxaloacetate, oxaloacetic acid, an oxaloacetate salt, alpha-ketoglutarate, or aspartate and a pharmaceutically acceptable carrier.

In yet another aspect of the invention, a method for protecting DNA and enhancing DNA damage repair from sun exposure is described. The method includes topically administering an effective amount of oxaloacetate, oxaloacetic acid, an oxaloacetate salt, alpha-ketoglutarate and aspartate and a pharmaceutically acceptable carrier.

In still another aspect of the invention, an improved animal chow formulation for increasing the life span of an animal is described, wherein the animal chow includes oxaloacetate, oxaloacetic acid, an oxaloacetate salt, alpha-ketoglutarate, or aspartate.

A method for activating beneficial genes and gene homologues by administering an effective amount of oxaloacetate, oxaloacetic acid, an oxaloacetate salt, alpha-ketoglutarate or aspartate is likewise described. The Oxaloacetate administration induces the change in expression of 356 genes in liver tissue in a similar manner as expressed by animals under Calorie Restriction. The change in these genes was sufficient to induce increases in health span and life span. The oxaloacetate can be administered orally, topically, or parenterally and is advantageously formulated with a buffer.

In another aspect of the invention, a method for reducing the incidence of cancer, treating cancer, and increasing the effectiveness of cancer treatment is described. The method includes administering to an individual in need thereof a pharmaceutically effective amount of a compound such as oxaloacetate, oxaloacetic acid, an oxaloacetate salt, alpha-ketoglutarate and aspartate. Optionally, the method can include the administration of a chemotherapeutic agent such as cyclophosphamide, chlorambucil, melphalan, estramustine, iphosphamide, prednimustin, busulphan, tiottepa, carmustin, lomustine, methotrexate, azathioprine, mercaptopurine, thioguanine, cytarabine, fluorouracil, vinblastine, vincristine, vindesine, etoposide, teniposide, dactinomucin, doxorubin, dunorubicine, epirubicine, bleomycin, nitomycin, cisplatin, carboplatin, procarbazine, amacrine, mitoxantron, tamoxifen, nilutamid, or aminoglutemide. The compound can be administered orally, topically, or parenterally. In some aspects of the invention, the chemotherapeutic agent is administered prior to administering the oxaloacetate compound. In other aspects, the chemotherapeutic agent is administered after or substantially contemporaneously with administering the compound. The cancer can be primary or metastatic malignant solid tumor disease or a hematological malignancy. If the cancer is a hematological malignancy, it may include acute and chronic myelogenous leukemia, acute and chronic lymphatic leukemia, multiple myeloma, Waldenstrom's macroglobulinemia, hairy cell leukemia, myelodisplastic syndrome, polycytaemia vera, and essential thrombocytosis.

In another aspect of the invention, a method of treating a disease associated with aging is described. The method includes administering a pharmaceutically acceptable amount of a compound selected from the group consisting of oxaloacetate, oxaloacetic acid, an oxaloacetate salt, alpha-ketoglutarate and aspartate, wherein the compound is formulated with a pharmaceutically acceptable carrier. A disease associated with aging can include osteoporosis, bone loss, arthritis, stiffening joints, cataracts, macular degeneration, diabetes, inflammation and heart disease. Optionally, the disease can be a neurodegenerative disease such as Alzheimer disease or Parkinson's disease.

In still another aspect of the invention, a method of reducing the symptoms associated with over-consumption of alcohol is provided. The method includes identifying an individual suffering from over-consumption of alcohol and administering a pharmaceutically effective amount of oxaloacetate, oxaloacetic acid, an oxaloacetate salt, alpha-ketoglutarate or aspartate. Symptoms of over-consumption of alcohol include, for example, headache, poor sense of overall well-being, diarrhea, loss of appetite, shakiness, fatigue, and nausea.

In another aspect of the invention, a composition of matter formulated for topical administration is described, wherein the composition includes oxaloacetate, oxaloacetic acid, an oxaloacetate salt, alpha-ketoglutarate, or aspartate, and a sunscreen.

In yet another aspect of the invention, a cosmetic composition formulated for topical administration is provided, wherein the cosmetic composition includes a compound such as oxaloacetate, oxaloacetic acid, an oxaloacetate salt, alpha-ketoglutarate or aspartate, and a cosmetic carrier.

In still another aspect of the invention, a composition of matter formulated for oral administration is disclosed, wherein the composition includes oxaloacetate, oxaloacetic acid, an oxaloacetate salt, alpha-ketoglutarate or aspartate and a vitamin.

In another aspect of the invention, a therapeutic composition is disclosed, wherein the composition includes a compound such as oxaloacetate, oxaloacetic acid, an oxaloacetate salt, alpha-ketoglutarate or aspartate and a therapeutic agent.

DETAILED DESCRIPTION OF THE PREFERRED EMBODIMENT

The present invention relates to compositions and methods for extending lifespan and treating disorders associated with aging in an individual in need thereof. The present invention is based, in part, on the surprising discovery that the administration of oxaloacetate and chemical precursors, including alpha-ketoglutarate and aspartate, results in a dose dependent lifespan increase in average population life span of up to 36% and up to 40% increase in maximal life span over similar populations of multi-cell control organisms including simple animals such as the nematode C. elegans, the more complicated fly D. melanogaster and in complex mammals. Without being bound to a particular theory, it is believed that external cellular contact with an oxaloacetate compound or its precursors, and subsequent transfer of the oxaloacetate into the cell, leads to metabolic signaling changes that activate beneficial genes that increase the lifespan of organisms. As used herein, the term "oxaloacetate" includes oxaloacetate, its salts, and chemical precursors of oxaloacetate including, without limitation, alpha-ketoglutarate and aspartate. The phrase "individual in need thereof" refers to any multi-cellular organism that would benefit from the life-extending and/or anti-aging effects of oxaloacetate. An individual includes, without limitation, any vertebrate or invertebrate susceptible to oxaloacetate administration. Exemplary vertebrates include fish, amphibians, reptiles, birds, and mammals such as humans, primates, canines, felines, or other animals.

Figure 1:
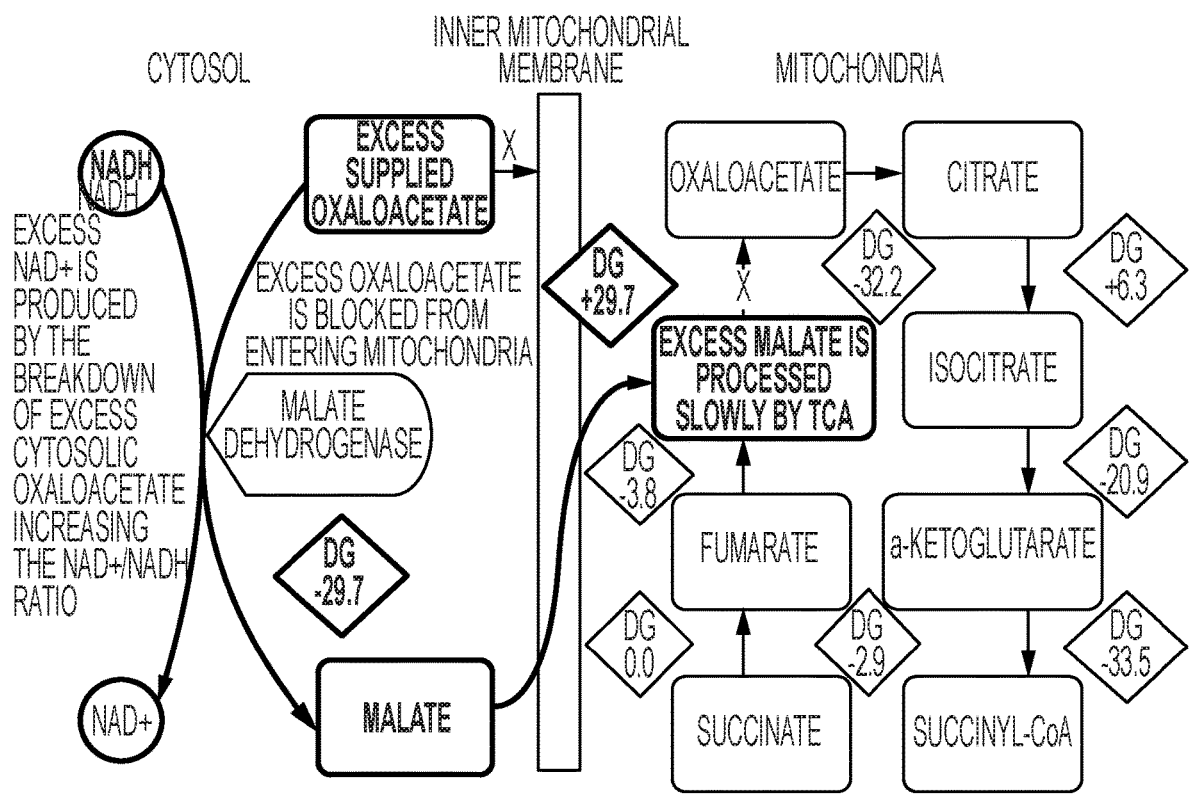
FIG. 1 is a schematic representation of the effect of oxaloacetate supplementation on increasing the ratio of NAD+/NADH to create a biological diode. The NAD+/NADH ratio is increased by the addition of Oxaloacetate. Supplied extra-cellular Oxaloacetate penetrates the cell membrane but can not penetrate the inner mitochondrial membrane. Oxaloacetate converts to malate in the cytosol due to the high negative delta G of the reaction. The cytosolic malate produced diffuses into the mitochondria, but is only slowly converted by the Citric Acid Cycle back into oxaloacetate (then into citrate) due to the high positive delta G of the reaction. Energy that typically fuels this conversion is not accessable because of the entry point of malate into the Citric Acid Cycle. This keeps the NAD+/NADH ratio higher than would normally occur, mimicking the conditions of Caloric Restriction. The increase in NAD+/NADH acts as a signal to regulate genes to produce beneficial repairs, reduces the incindence of cancer and other age related disease, block fat production, reduces apoptosis and increases the overall lifespan of the organism.

The present invention is based, in part, on the observation that oxaloacetate introduced into a cell cannot cross the inner membrane of the mitochondria [23]. The additional oxaloacetate introduced into the cytosol is reduced to malate by the enzyme malate dehydrogenase. This reaction also converts NADH into NAD+, increasing the NAD+/NADH ratio. The malate formed by the introduction of additional oxaloacetate to the cytosol can cross the mitochondria membrane through an exchange for α-ketoglutarate. Once in the mitochondria, the malate can be converted back into oxaloacetate by way of the Citric Acid Cycle. Conversion of the malate back into oxaloacetate would generate NADH from NAD+, and lower the NAD+/NADH ratio, as occurs in pyruvate which prevents the increase in lifespan. The lowering of the NAD+/NADH ratio, however, does not occur with the addition of oxaloacetate in the cytosol, because the Gibbs Free Energy, delta G, is highly positive (+29.7) for the reaction of malate to oxaloacetate. Under normal conditions, the only reason the reaction of malate to oxaloacetate proceeds at all in the Citric Acid Cycle is due to the energy gained due to the conversion of oxaloacetate to acetyl CoA in the mitochondria (delta G of −32.2) and the energy of the other intermediates of the Citric Acid Cycle. Because the oxaloacetate added to the cytosol cannot penetrate the mitochondrial membrane, there is no additional oxaloacetate in the mitochondria to power the reaction of malate to oxaloacetate in the Citric Acid Cycle. Thus, the ratio of NAD+/NADH stays high with the addition of oxaloacetate to the cytosol. In effect, an electron biological diode is created by the addition of oxaloacetate to the cytosol, the inability of oxaloacetate to penetrate the mitochondria, and the high delta G of the reaction of malate back into oxaloacetate in the mitochondria. FIG. 1 illustrates the effect of oxaloacetate supplementation on increasing the ratio of NAD+/NADH. As indicated in FIG. 1, the supplementation of extra-cellular oxaloacetate acts to penetrate the cell membrane but is precluded from penetrating the inner mitochondrial membrane. The maintained increase in the NAD+/NADH ratio is a signaling effect that starts the increase in the expression of beneficial genes and the increase in associated beneficial proteins along with the decrease in the expression of non-beneficial genes and the decrease in associate non-beneficial proteins. By keeping the NAD+/NADH ratio higher than would normally occur, oxaloacetate effectively mimics the effect of CR and facilitates the regulation of genes to produce beneficial repairs, reduce the incidence of cancer and other age-related disease, block fat production, reduce apoptosis, and increase the overall lifespan of an organism.

The increase in NAD+/NADH ratio by oxaloacetate allows the activation of beneficial genes, which results in the same benefits as those seen in CR because the signaling mechanism is similar. The beneficial genes upregulated in CR include the following classes of genes: lipid catabolism and activation of the oxidative stress response; regulation of central metabolic pathways including SAM and urea cycles; regulation of hormonal pathways; DHEA and insulin/Igf signaling; genome instability and apoptosis. Reviews of these gene types can be found in works by Bauer (Bauer, et al, "Starvation response in mouse liver shows strong correlation with lifespan prolonging processes", Physiologicaly Genomics, Feb. 3, 2004, 10.1152/physiolgenomics.00203.2003), Cao (Cao, et al, "Genomic profiling of short- and long-term caloric restriction effects in the liver of aging mice", Proc Natl Acad Sci 98: 10630-10635, 2001), and Lee (Lee, et al., The impact of α-Lipoic Acid, Coenzyme Q10, and Caloric Restriction on Life Span and Gene Expression Patterns in Mice, Free Radical Biology & Medicine, Vol. 36, No. 8, pp. 1043-1057, 2004) hereby incorporated by reference in their entireties. The inventor shows that mice subjected to calorie restriction results in the change of levels of gene expression in 1,763 genes in liver tissue as compared to a control group fed freely. Mice fed oxaloacetate but allowed to eat freely resulted in a change of expression in 765 genes. Because these are pooled results, many of the changes in gene expression are due to individual variations within the mice. However, when genes that are changed from the control group are commonly expressed by both the calorie restricted mice and the oxaloacetate administered mice, these genes can be considered as the driving reason for similarities in physical changes as compared to the control group fed freely that they are compared against. The physical changes documented include the decrease in body weight, an increase in health span and resistance to disease, and an increase in lifespan. 363 genes showed a common change from the control mice. Of these 363 genes, 357 show either an upregulation of the expression of the gene or a down regulation in the expression of the gene in the same direction away from the control group. It is apparent that these 357 genes expressed in similar fashion as compared to the control are responsible for the positive changes in lifespan (98% of all genes changed in common as compared to the control group). Homologues of these genes expressed in other animals will have a similar physical effect. Note that there may be other genes expressed in other tissues other than the liver that undoubtedly also assist in lifespan extension, however the liver is one of the key organs for the regulation of metabolism, that through calorie restriction has shown to be critical to increases in mammalian lifespan and health span.

The beneficial genes activated and non-beneficial genes down-regulated in the liver tissue are shown in Tables 1 and 2.

TABLE 1

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| Gene Symbol | Gene Title | Affymatrix No. | CR to C Signal Log Ratio | CR to C Change | OX to C Signal Log Ratio | OX to C Change | Gene Movement in Same Direction? |
|---|---|---|---|---|---|---|---|
| Aacs | acetoacetyl-CoA synthetase | 8056 | 1.5 | I | −0.2 | D | NO |
| Abcg2 | ATP-binding cassette, sub-family G (WHITE), member 2 | 7165 | −0.5 | D | −0.3 | D | YES |
| Abhd6 | abhydrolase domain containing 6 | 3498 | −0.3 | D | −0.4 | D | YES |
| Acaa1 | acetyl-Coenzyme A acyltransferase 1 | 1341 | −0.3 | D | −0.3 | D | YES |
| Acp1 | acid phosphatase 1, soluble | 6975 | −1.1 | D | −0.9 | D | YES |
| Actb | actin, beta, cytoplasmic | 46 | −0.3 | D | −0.2 | D | YES |
| Actg | actin, gamma, cytoplasmic | 174 | −0.4 | D | −0.5 | D | YES |
| Adn | adipsin | 2262 | −1.1 | D | −0.7 | D | YES |
| Ahcyl1 | S-adenosylhomocysteine hydrolase-like 1 | 11090 | −0.6 | D | −0.4 | D | YES |
| AI746432 | expressed sequence AI746432 | 8752 | −0.3 | D | −0.3 | D | YES |
| AI746432 | expressed sequence AI746432 | 19500 | −0.4 | D | −0.5 | D | YES |
| Akr1d1 | aldo-keto reductase family 1, member D1 | 21474 | −0.7 | D | −0.5 | D | YES |
| Aldh3a2 | aldehyde dehydrogenase family 3, subfamily A2 | 171 | −0.3 | D | −0.4 | D | YES |
| Anxa5 | annexin A5 | 9826 | −0.7 | D | −0.4 | D | YES |
| Aof1 | amine oxidase, flavin containing 1 | 27011 | −0.7 | D | −0.7 | D | YES |
| Aox1 | aldehyde oxidase 1 | 3830 | −0.3 | D | −0.4 | D | YES |
| Ap3s2 | adaptor-related protein complex 3, sigma 2 subunit | 3760 | −0.3 | D | −0.3 | D | YES |
| Ap3s2 | adaptor-related protein complex 3, sigma 2 subunit | 17618 | −0.2 | D | −0.3 | D | YES |
| Apoa4 | apolipoprotein A-IV | 2156 | −0.7 | D | −0.8 | D | YES |
| Apoa4 | apolipoprotein A-IV | 14772 | −0.7 | D | −1 | D | YES |
| Asb13 | ankyrin repeat and SOCS box-containing protein 13 | 3796 | −0.9 | D | −0.7 | D | YES |
| Asb13 | ankyrin repeat and SOCS box-containing protein 13 | 17635 | −0.8 | D | −0.3 | D | YES |
| Atp6v1h | ATPase, H+ transporting, lysosomal 50/57 kDa, V1 subunit H | 221 | −0.4 | D | −0.5 | D | YES |
| Bpnt1 | bisphosphate 3′-nucleotidase 1 | 17387 | −0.6 | D | −0.7 | D | YES |
| Bnp17 | brain protein 17 | 3141 | −1.1 | D | −0.4 | D | YES |
| Btf3 | basic transcription factor 3 | 8098 | −0.4 | D | −0.5 | D | YES |
| Btg1 | B-cell translocation gene 1, anti-proliferative | 10342 | −0.9 | D | −0.3 | D | YES |
| Btg2 | B-cell translocation gene 2, anti-proliferative | 16448 | −0.8 | D | −0.4 | D | YES |
| C330018J07Rik | RIKEN cDNA C330018J07 gene | 11390 | −0.6 | D | −0.6 | D | YES |
| Cald1 | caldesmon 1 | 9027 | −0.4 | D | −0.4 | D | YES |
| Calm1 | calmodulin 1 | 21261 | −0.5 | D | −0.3 | D | YES |
| Car14 | carbonic anhydrase 14 | 18852 | −0.4 | D | −0.6 | D | YES |
| Cbx1 | chromobox homolog 1 (Drosophila HP1 beta) | 13736 | −0.5 | D | −0.4 | D | YES |
| Ccng1 | cyclin G1 | 5086 | −0.9 | D | −0.3 | D | YES |
| Cct6a | chaperonin subunit 6a (zeta) | 21805 | −0.5 | D | −0.2 | D | YES |
| Cd151 | CD151 antigen | 21861 | −0.8 | D | −0.5 | D | YES |
| Cd163 | CD163 antigen | 3539 | −1 | D | −0.4 | D | YES |
| Cd36 | CD36 antigen | 7425 | −1.1 | D | −0.7 | D | YES |
| Cd36 | CD36 antigen | 19010 | −1.2 | D | −0.8 | D | YES |
| Cd36 | CD36 antigen | 19011 | −1.3 | D | −0.3 | D | YES |
| Cd59a | CD59a antigen | 3105 | −0.3 | D | −0.3 | D | YES |
| Cd59a | CD59a antigen | 12906 | −0.5 | D | −0.3 | D | YES |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | | | | |
|---|---|---|---|---|---|---|
| Cdc42 | cell division cycle 42 homolog (S. cerevisiae) | 119 | D | −0.4 | −0.5 | YES |
| Ces3 | carboxylesterase 3 | 14412 | D | −0.5 | −0.4 | YES |
| Chc1l | chromosome condensation 1-like | 784 | D | −0.7 | −0.5 | YES |
| Chpt1 | choline phosphotransferase 1 | 10405 | D | −0.6 | −0.4 | YES |
| Chpt1 | choline phosphotransferase 1 | 14436 | D | −0.4 | −0.3 | YES |
| Cklfsf6 | chemokine-like factor super family 6 | 8051 | D | −0.3 | −0.5 | YES |
| Cml5 | camello-like 5 | 9070 | D | −1.3 | −0.7 | YES |
| Cnbp | cellular nucleic acid binding protein | 15347 | D | −0.9 | −0.5 | YES |
| Cnn3 | calponin 3, acidic | 21628 | D | 0.5 | −0.4 | YES |
| Col3a1 | procollagen, type III, alpha 1 | 12142 | I | −1.1 | −0.7 | YES |
| Cryz | crystallin, zeta | 15627 | D | −0.7 | −0.7 | YES |
| Cugbp2 | CUG triplet repeat, RNA binding protein 2 | 19281 | D | −0.5 | −0.9 | YES |
| Cxadr | coxsackievirus and adenovirus receptor | 39334 | D | −0.5 | −0.4 | YES |
| Cyp17a1 | cytochrome P450, family 17, subfamily a, polypeptide 1 | 1412 | D | −1.1 | −0.4 | YES |
| Cyp2b20 | cytochrome P450, family 2, subfamily b, polypeptide 20 | 6516 | D | −1 | −0.3 | YES |
| Cyp2b20 | cytochrome P450, family 2, subfamily b, polypeptide 20 | 9904 | D | −1.1 | −0.3 | YES |
| Cyp2b20 | cytochrome P450, family 2, subfamily b, polypeptide 20 | 19914 | D | −0.8 | −0.3 | YES |
| Cyp2b9 | cytochrome P450, family 2, subfamily b, polypeptide 9 | 3985 | D | −2.5 | −1 | YES |
| Cyp2c38 | cytochrome P450, family 2, subfamily c, polypeptide 38 | 20628 | D | −0.9 | −0.6 | YES |
| Cyp2j5 | cytochrome P450, family 2, subfamily j, polypeptide 5 | 1926 | D | −0.2 | −0.3 | YES |
| Cyp2j5 | cytochrome P450, family 2, subfamily j, polypeptide 5 | 1927 | D | −0.7 | −0.5 | YES |
| Cyp4a10 | cytochrome P450, family 4, subfamily a, polypeptide 10 | 9112 | D | −0.5 | −0.6 | YES |
| Cyp7a1 | cytochrome P450, family 7, subfamily a, polypeptide 1 | 15692 | I | 1.6 | 0.6 | YES |
| D10Ertd641e | DNA segment, Chr 10, ERATO Doi 641, expressed | 17514 | D | −0.5 | −0.2 | YES |
| D11Ertd175e | DNA segment, Chr 11, ERATO Doi 175, expressed | 1000 | D | −0.3 | −0.3 | YES |
| D11Ertd672e | DNA segment, Chr 11, ERATO Doi 672, expressed | 15860 | D | −0.8 | −0.5 | YES |
| D19Wsu12e | DNA segment, Chr 19, Wayne State University 12, expressed | 13728 | D | −0.7 | −0.3 | YES |
| D430028G21Rik | RIKEN cDNA D430028G21 gene | 15861 | D | −0.5 | −0.8 | YES |
| D530020C15Rik | RIKEN cDNA D530020C15 gene | 8006 | D | −0.8 | −0.7 | YES |
| D630002G06 | hypothetical protein D630002G06 | 19762 | D | −1.3 | −0.5 | YES |
| D8Wsu49e | DNA segment, Chr 8, Wayne State University 49, expressed | 14498 | D | −0.4 | −0.7 | YES |
| Ddc | dopa decarboxylase | 10474 | D | −1.1 | −0.4 | YES |
| Desrt | developmentally and sexually retarded with transient immune abnormalities | 27378 | I | 0.9 | 0.7 | YES |
| Desrt | developmentally and sexually retarded with transient immune abnormalities | 33187 | I | 1.3 | 0.6 | YES |
| Dgat2l1 | diacylglycerol O-acyltransferase 2-like 1 | 3899 | D | −1.8 | −1.4 | YES |
| Dio1 | deiodinase, iodothyronine, type I | 2386 | D | −0.8 | −0.4 | YES |
| Dmd | dystrophin, muscular dystrophy | 16841 | D | −1 | −0.6 | YES |
| Dpp4 | dipeptidylpeptidase 4 | 44785 | D | −0.5 | −0.6 | YES |
| Dusp1 | dual specificity phosphatase 1 | 17006 | D | −0.5 | −1 | YES |
| Egfl5 | EGF-like-domain, multiple 5 | 27189 | D | −0.8 | −0.7 | YES |
| Egfr | epidermal growth factor receptor | 22508 | I | 1.1 | 0.5 | YES |
| Egr1 | early growth response 1 | 1460 | D | −0.6 | 1.2 | NO |
| EII2 | elongation factor RNA polymerase II 2 | 18871 | D | −0.3 | −0.4 | YES |
| Elovl6 | ELOVL family member 6, elongation of long chain fatty acids (yeast) | 1798 | D | −1.2 | −0.6 | YES |
| Elovl6 | ELOVL family member 6, elongation of long chain fatty acids (yeast) | 1799 | D | −1.3 | −0.6 | YES |
| Entpd5 | ectonucleoside triphosphate diphosphohydrolase 5 | 1778 | D | −0.3 | −0.4 | YES |
| Entpd5 | ectonucleoside triphosphate diphosphohydrolase 5 | 19892 | D | −0.6 | −0.4 | YES |
| Ephx1 | epoxide hydrolase 1, microsomal | 6697 | D | −0.3 | −0.3 | YES |
| Etohi1 | ethanol induced 1 | 23890 | D | −0.9 | −0.4 | YES |
| Fabp4 | fatty acid binding protein 4, adipocyte | 1418 | D | −1.4 | −0.8 | YES |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| Gene | Description | ID | Val1 | Dir1 | Val2 | Dir2 | Common |
|---|---|---|---|---|---|---|---|
| Fabp4 | fatty acid binding protein 4, adipocyte | 19390 | -1.7 | D | -1.4 | D | YES |
| Fabp5 | fatty acid binding protein 5, epidermal | 416 | 0.8 | I | 1.4 | I | YES |
| Fabp5 | fatty acid binding protein 5, epidermal | 417 | 1.2 | I | 1.8 | I | YES |
| Fasn | fatty acid synthase | 8087 | -1 | D | -0.3 | D | YES |
| Fbxo17 | F-box only protein 17 | 8360 | 0.9 | I | 0.8 | I | YES |
| Fgd4 | FYVE, RhoGEF and PH domain containing 4 | 40830 | -0.7 | D | -0.3 | D | YES |
| Fin15 | fibroblast growth factor inducible 15 | 5793 | -0.7 | D | -0.6 | D | YES |
| Fkbp1a | FK506 binding protein 1a | 21907 | -0.4 | D | -0.4 | D | YES |
| Fmo5 | flavin containing monooxygenase 5 | 5968 | -0.7 | D | -0.5 | D | YES |
| Foxa1 | forkhead box A1 | 2891 | 0.3 | I | 0.4 | I | YES |
| Foxa3 | forkhead box A3 | 13370 | 1 | I | 0.7 | I | YES |
| Foxq1 | forkhead box Q1 | 6994 | 1.1 | I | 2.1 | I | YES |
| Foxq1 | forkhead box Q1 | 30006 | 1.9 | I | 2.2 | I | YES |
| Fsp27 | fat specific gene 27 | 20387 | -1 | D | -0.9 | D | YES |
| G0s2 | G0/G1 switch gene 2 | 16876 | -0.6 | D | -0.5 | D | YES |
| Gas2 | growth arrest specific 2 | 18239 | -0.7 | D | -0.6 | D | YES |
| Gbe1 | glucan (1,4-alpha-), branching enzyme 1 | 4913 | -0.7 | D | -0.3 | D | YES |
| Gdf15 | growth differentiation factor 15 | 3344 | -1.3 | D | -0.6 | D | YES |
| Gga2 | golgi associated, gamma adaptin ear containing, ARF binding protein 2 | 12397 | -0.5 | D | -0.4 | D | YES |
| Ggcx | gamma-glutamyl carboxylase | 15640 | -0.3 | D | -0.4 | D | YES |
| Gpam | glycerol-3-phosphate acyltransferase, mitochondrial | 3894 | -0.8 | D | -0.4 | D | YES |
| Gpam | glycerol-3-phosphate acyltransferase, mitochondrial | 10093 | -1 | D | -0.6 | D | YES |
| Gpd1 | glycerol-3-phosphate dehydrogenase 1 (soluble) | 599 | -0.5 | D | -0.6 | D | YES |
| Grsf1 | G-rich RNA sequence binding factor 1 | 15337 | -0.4 | D | -0.5 | D | YES |
| Gsta2 | glutathione S-transferase, alpha 2 (Yc2) | 5299 | -0.3 | D | -1.2 | D | YES |
| Gsta2 | glutathione S-transferase, alpha 2 (Yc2) | 5300 | -0.6 | D | -1 | D | YES |
| Gstm3 | glutathione S-transferase, mu 3 | 11732 | -1.3 | D | -1.1 | D | YES |
| Gstm3 | glutathione S-transferase, mu 3 | 11733 | -1 | D | -1.1 | D | YES |
| Gys2 | glycogen synthase 2 | 9074 | 0.6 | I | -0.4 | D | NO |
| H2afz | H2A histone family, member Z | 21834 | -0.5 | D | -0.5 | D | YES |
| Hadh2 | hydroxyacyl-Coenzyme A dehydrogenase type II | 15557 | -0.5 | D | -0.3 | D | YES |
| Hao3 | hydroxyacid oxidase (glycolate oxidase) 3 | 3049 | -0.9 | D | -0.4 | D | YES |
| Hnmt | histamine N-methyltransferase | 2097 | -0.7 | D | -0.6 | D | YES |
| Hnrpr | heterogeneous nuclear ribonucleoprotein R | 15204 | -0.7 | D | -0.7 | D | YES |
| Hpgd | hydroxyprostaglandin dehydrogenase 15 (NAD) | 4263 | -0.3 | D | -0.3 | D | YES |
| Hsd17b4 | hydroxysteroid (17-beta) dehydrogenase 4 | 21694 | -0.5 | D | -0.4 | D | YES |
| Hsp105 | heat shock protein 105 | 7825 | -0.9 | D | -0.3 | D | YES |
| Hspb1 | heat shock protein 1 | 7202 | -0.9 | D | -0.5 | D | YES |
| Hspb1 | heat shock protein 1 | 10223 | -0.9 | D | -0.6 | D | YES |
| Hspca | heat shock protein 1, alpha | 15187 | -0.8 | D | -0.5 | D | YES |
| Hspca | heat shock protein 1, alpha | 15746 | -0.9 | D | -0.6 | D | YES |
| Ide | insulin degrading enzyme | 32880 | -0.7 | D | -0.4 | D | YES |
| Ifi1 | interferon inducible protein 1 | 3220 | -1.5 | D | -0.3 | D | YES |
| Ifi205 | interferon activated gene 205 | 20358 | -1.4 | D | -0.9 | D | YES |
| Ifi205 | interferon activated gene 205 | 20475 | -1.2 | D | -1.6 | D | YES |
| Ifi205 | interferon activated gene 205 | 20476 | -1.4 | D | -0.7 | D | YES |
| Ifit1 | interferon-induced protein with tetratricopeptide repeats 1 | 18910 | -2 | D | -0.5 | D | YES |
| Ifd2 | induced in fatty liver dystrophy 2 | 10324 | 0.4 | I | -0.7 | D | NO |
| Impa1 | inositol (myo)-1(or 4)-monophosphatase 1 | 14900 | -0.4 | D | -0.4 | D | YES |
| Insig2 | insulin induced gene 2 | 2377 | -1.2 | D | -0.3 | D | YES |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | | | | | |
|---|---|---|---|---|---|---|---|
| Irf7 | interferon regulatory factor 7 | 1639 | −1.6 | D | −0.6 | D | YES |
| Ivns1abp | influenza virus NS1A binding protein | 9977 | −0.4 | D | −0.5 | D | YES |
| Jun | Jun oncogene | 1804 | −0.6 | D | −1.3 | D | YES |
| Kif5b | kinesin family member 5B | 2824 | −0.8 | D | −0.5 | D | YES |
| Klf3 | Kruppel-like factor 3 (basic) | 40423 | −0.4 | D | −0.4 | D | YES |
| Lamp2 | lysosomal membrane glycoprotein 2 | 738 | −0.5 | D | −0.5 | D | YES |
| Laptm4b | lysosomal-associated protein transmembrane 4B | 14935 | −0.7 | D | −1.1 | D | YES |
| Laptm4b | lysosomal-associated protein transmembrane 4B | 15537 | −0.3 | D | −0.3 | D | YES |
| Lasp1 | LIM and SH3 protein 1 | 15643 | −0.7 | D | −0.6 | D | YES |
| Lasp1 | LIM and SH3 protein 1 | 15644 | −0.9 | D | −0.6 | D | YES |
| Lasp1 | LIM and SH3 protein 1 | 15888 | −0.5 | D | −0.5 | D | YES |
| Lasp1 | LIM and SH3 protein 1 | 21597 | −0.9 | D | −0.9 | D | YES |
| Lcn2 | lipocalin 2 | 12006 | −1.8 | D | −0.7 | D | YES |
| Lgals1 | lectin, galactose binding, soluble 1 | 3968 | −1.7 | D | −0.5 | D | YES |
| Lgals1 | lectin, galactose binding, soluble 1 | 21588 | −1.6 | D | −0.6 | D | YES |
| LOC209387 | tripartite motif protein 30-like | 22024 | −1.9 | D | −0.4 | D | YES |
| LOC226691 | interferon-activatable protein | 41947 | −1.6 | D | −0.3 | D | YES |
| Luc7l2 | LUC7-like 2 (S. cerevisiae) | 14858 | −1.1 | D | −0.6 | D | YES |
| Ly6a | lymphocyte antigen 6 complex, locus A | 1580 | −1.6 | D | −0.8 | D | YES |
| Ly6d | lymphocyte antigen 6 complex, locus D | 1325 | −3.4 | D | −2.2 | D | YES |
| Ly6e | lymphocyte antigen 6 complex, locus E | 39351 | −1 | D | −0.2 | D | YES |
| Lypla1 | lysophospholipase 1 | 16420 | −0.6 | D | −0.4 | D | YES |
| Map3k5 | mitogen activated protein kinase kinase 5 | 5599 | 1.2 | I | 0.7 | I | YES |
| MGC25972 | similar to cytochrome P450, 4a10 | 8611 | −0.6 | D | −0.4 | D | YES |
| Mme | membrane metallo endopeptidase | 21792 | −1.1 | D | −0.7 | D | YES |
| Morf4l2 | mortality factor 4 like 2 | 22127 | −0.4 | D | −0.3 | D | YES |
| Mtap | methylthioadenosine phosphorylase | 19473 | −0.3 | D | −0.5 | D | YES |
| Mtmr6 | myotubularin related protein 6 | 22038 | −0.5 | D | −0.4 | D | YES |
| Ndufab1 | NADH dehydrogenase (ubiquinone) 1, alpha/beta subcomplex, 1 | 16170 | −0.2 | D | −0.2 | D | YES |
| Ndufs5 | NADH dehydrogenase (ubiquinone) Fe—S protein 5 | 890 | −0.5 | D | −0.2 | D | YES |
| Nr0b2 | nuclear receptor subfamily 0, group B, member 2 | 17981 | −0.8 | D | −0.3 | D | YES |
| Nr1d2 | nuclear receptor subfamily 1, group D, member 2 | 1353 | 0.5 | I | −0.3 | D | NO |
| Nrbf2 | nuclear receptor binding factor 2 | 16934 | −0.6 | D | −0.4 | D | YES |
| Nt5e | 5′ nucleotidase, ecto | 23035 | −1.5 | D | −0.6 | D | YES |
| Oas1g | 2′-5′ oligoadenylate synthetase 1G | 9034 | −1.2 | D | −1.2 | D | YES |
| Olig1 | oligodendrocyte transcription factor 1 | 544 | −0.8 | D | −0.5 | D | YES |
| Omd | osteomodulin | 3140 | −0.8 | D | −0.6 | D | YES |
| Oprs1 | opioid receptor, sigma 1 | 20083 | −0.5 | D | −0.3 | D | YES |
| Orm2 | orosomucoid 2 | 4697 | −1.2 | D | −0.6 | D | YES |
| Osbpl3 | oxysterol binding protein-like 3 | 22995 | −0.9 | D | −1.1 | D | YES |
| Osp94 | osmotic stress protein | 2648 | −0.8 | D | −0.3 | D | YES |
| Osp94 | osmotic stress protein | 17186 | −1.2 | D | −0.6 | D | YES |
| Paics | phosphoribosylaminoimidazole carboxylase, phosphoribosylaminoribosylaminoimidazole, succinocarboxamide synthetase | 14710 | −0.5 | D | −0.6 | D | YES |
| Pbx2 | pre B-cell leukemia transcription factor 2 | 17437 | 1.3 | I | 1.5 | I | YES |
| Pgd | phosphogluconate dehydrogenase | 14862 | −0.6 | D | −0.4 | D | YES |
| Pgd | phosphogluconate dehydrogenase | 15144 | −0.6 | D | −0.3 | D | YES |
| Pgd | phosphogluconate dehydrogenase | 15638 | −0.5 | D | −0.3 | D | YES |
| Phlda1 | pleckstrin homology-like domain, family A, member 1 | 3230 | 1.3 | I | 1.2 | I | YES |
| Plscr2 | phospholipid scramblase 2 | 17137 | −0.9 | D | −1.1 | D | YES |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | | | |
|---|---|---|---|---|---|
| Pnrc1 | proline-rich nuclear receptor coactivator 1 | 13710 | −0.7 | D | YES |
| Ppicap | peptidylprolyl isomerase C-associated protein | 16556 | −1.1 | D | YES |
| Ppp1cb | protein phosphatase 1, catalytic subunit, beta isoform | 13645 | −0.4 | D | YES |
| Prnp | prion protein | 525 | −0.4 | D | YES |
| Prnp | prion protein | 16409 | −0.7 | D | YES |
| Psmc4 | proteasome (prosome, macropain) 26S subunit, ATPase, 4 | 685 | −0.4 | D | YES |
| Ptp4a2 | protein tyrosine phosphatase 4a2 | 14326 | −0.7 | D | YES |
| Pvrl3 | poliovirus receptor-related 3 | 7590 | −0.4 | D | YES |
| Qk | quaking | 1468 | −0.9 | D | YES |
| Rae1lc | retinoic acid early transcript gamma | 4862 | −0.5 | D | YES |
| Ran | RAN, member RAS oncogene family | 14098 | −0.6 | D | YES |
| Rbms1 | RNA binding motif, single stranded interacting protein 1 | 3098 | 0.8 | I | YES |
| Rbpms | RNA binding protein gene with multiple splicing | 21777 | −0.8 | D | YES |
| Rdx | radixin | 574 | −0.4 | D | YES |
| Rfx4 | regulatory factor X, 4 (influences HLA class II expression) | 29047 | −0.7 | D | YES |
| Rgs5 | regulator of G-protein signaling 5 | 1861 | −1.3 | D | YES |
| Rgs5 | regulator of G-protein signaling 5 | 5200 | −1.5 | D | YES |
| Rtn4 | reticulon 4 | 5375 | −0.5 | D | YES |
| Rtn4 | reticulon 4 | 20776 | −0.6 | D | YES |
| S100a11 | S100 calcium binding protein A11 (calizzarin) | 22439 | −0.5 | D | YES |
| Saa1 | serum amyloid A 1 | 18915 | −1.9 | D | YES |
| Saa2 | serum amyloid A 2 | 3470 | −1.8 | D | YES |
| Saa2 | serum amyloid A 2 | 17502 | −1.9 | D | YES |
| Saa4 | serum amyloid A 4 | 3714 | −0.4 | D | YES |
| Sc5d | sterol-C5-desaturase (fungal ERG3, delta-5-desaturase) homolog (S. cerevisiae) | 27509 | −0.5 | D | YES |
| Scamp1 | secretory carrier membrane protein 1 | 11034 | 0.6 | I | NO |
| Sdc1 | syndecan 1 | 15098 | −0.6 | D | YES |
| Sdc1 | syndecan 1 | 16334 | −0.4 | D | YES |
| Sdfr1 | stromal cell derived factor receptor 1 | 216 | −0.5 | D | YES |
| Sec8 | SEC8 (S. cerevisiae) | 6944 | −0.7 | D | YES |
| 7-Sep | septin 7 | 15402 | −0.8 | D | YES |
| Serpina4-ps1 | serine (or cysteine) proteinase inhibitor, clade A, member 4, pseudogene 1 | 35241 | 3.6 | I | YES |
| Serpinb1a | serine (or cysteine) proteinase inhibitor, clade B, member 1a | 713 | −1.7 | D | YES |
| Serpinb1a | serine (or cysteine) proteinase inhibitor, clade B, member 1a | 16477 | −1.5 | D | YES |
| Sgk | serum/glucocorticoid regulated kinase | 436 | −0.7 | D | YES |
| Sgpp1 | sphingosine-1-phosphate phosphatase 1 | 5081 | −0.5 | D | YES |
| Sh3bgrl | SH3-binding domain glutamic acid-rich protein like | 12366 | −0.8 | D | YES |
| Sh3bgrl | SH3-binding domain glutamic acid-rich protein like | 14980 | −0.8 | D | YES |
| Slc25a10 | solute carrier family 25 (mitochondrial carrier; dicarboxylate transporter), member 10 | 1350 | −0.5 | D | YES |
| Slc25a5 | solute carrier family 25 (mitochondrial carrier; adenine nucleotide translocator), member 5 | 15757 | −0.5 | D | YES |
| Slco1a1 | solute carrier organic anion transporter family, member 1a1 | 4638 | 1 | I | YES |
| Snap23 | synaptosomal-associated protein 23 | 5156 | −0.9 | D | YES |
| Socs2 | suppressor of cytokine signaling 2 | 17285 | 2.8 | I | YES |
| Sorbs1 | sorbin and SH3 domain containing 1 | 14845 | −0.4 | D | YES |
| Spp1 | secreted phosphoprotein 1 | 17430 | −0.9 | D | YES |
| Srr | serine racemase | 4059 | −0.4 | D | YES |
| Stat1 | signal transducer and activator of transcription 1 | 18160 | −1.3 | D | YES |
| Stch | stress 70 protein chaperone, microsome-associated, human homolog | 27078 | −0.8 | D | YES |
| Surf4 | surfeit gene 4 | 14104 | −0.3 | D | YES |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | | | | | |
|---|---|---|---|---|---|---|---|
| Surf4 | surfeit gene 4 | 21721 | −0.4 | D | −0.4 | D | YES |
| Sycp3 | synaptonemal complex protein 3 | 14586 | −0.3 | D | −0.4 | D | YES |
| Sycp3 | synaptonemal complex protein 3 | 21760 | −1.3 | D | −1.1 | D | YES |
| Tcte11 | t-complex-associated-testis-expressed 1-like | 18055 | −0.6 | D | −0.4 | D | YES |
| Tcte11 | t-complex-associated-testis-expressed 1-like | 44706 | −0.8 | D | −0.6 | D | YES |
| Tfpi2 | tissue factor pathway inhibitor 2 | 2942 | −0.8 | D | −0.3 | D | YES |
| Tgfb1i4 | transforming growth factor beta 1 induced transcript 4 | 10001 | −1 | D | −0.2 | D | YES |
| Tgoln1 | trans-golgi network protein | 7566 | −0.6 | D | −0.4 | D | YES |
| Tgtp | T-cell specific GTPase | 17185 | −1.2 | I | 0.9 | D | NO |
| Thrsp | thyroid hormone responsive SPOT14 homolog (*Rattus*) | 7232 | −0.7 | D | −0.4 | D | YES |
| Tkt | transketolase | 15963 | −0.2 | D | −0.2 | D | YES |
| Tmlhe | trimethyllysine hydroxylase, epsilon | 4984 | −0.5 | D | −0.6 | D | YES |
| Tpm2 | tropomyosin 2, beta | 4133 | −0.6 | D | −0.7 | D | YES |
| Trim2 | tripartite motif protein 2 | 16727 | −1.7 | D | −0.4 | D | YES |
| Ttc13 | tetratricopeptide repeat domain 13 | 15641 | −0.6 | D | −0.3 | D | YES |
| Tuba6 | tubulin, alpha 6 | 16408 | −0.6 | D | −0.3 | D | YES |
| Tubb2 | tubulin, beta 2 | 11606 | −2.7 | D | −1 | D | YES |
| Txnl2 | thioredoxin-like 2 | 21924 | −0.6 | D | −0.3 | D | YES |
| Ubce8 | ubiquitin-conjugating enzyme 8 | 1567 | −0.5 | D | −0.6 | D | YES |
| Ube1c | ubiquitin-activating enzyme E1C | 1597 | −0.6 | D | −0.4 | D | YES |
| Ube1c | ubiquitin-activating enzyme E1C | 14339 | −0.9 | D | −0.7 | D | YES |
| Ube1b | ubiquitin-like 1 (sentrin) activating enzyme E1B | 15097 | −0.6 | D | −0.5 | D | YES |
| Ucp2 | uncoupling protein 2, mitochondrial | 16364 | −1.7 | D | −0.5 | D | YES |
| Ugdh | UDP-glucose dehydrogenase | 703 | −0.5 | D | −0.3 | D | YES |
| Usp18 | ubiquitin specific protease 18 | 2586 | −1.8 | D | −0.8 | D | YES |
| Vldlr | very low density lipoprotein receptor | 14041 | −0.7 | D | −0.5 | D | YES |
| Vnn1 | vanin 1 | 2881 | −1.4 | D | −0.8 | D | YES |
| Vnn1 | vanin 1 | 38738 | −1.4 | D | −0.7 | D | YES |
| Wdfy3 | WD repeat and FYVE domain containing 3 | 23015 | −0.7 | D | −0.4 | D | YES |
| Ywhaz | tyrosine 3-monooxygenase/tryptophan 5-monooxygenase activation protein, zeta polypeptide | 14966 | −0.6 | D | −0.3 | D | YES |
| Zfp207 | zinc finger protein 207 | 15684 | −1.1 | D | −0.8 | D | YES |
| — | *Mus musculus* similar to olfactomedin 3 (LOC381467), mRNA | 10157 | −0.9 | D | −0.8 | D | YES |
| — | *Mus musculus* transcribed sequence with strong similarity to protein sp: P07900 (*H. sapiens*) HS9A_HUMAN Heat shock protein HSP 90-alpha (HSP 86) | 10904 | −1.1 | D | −0.6 | D | YES |
| — | *Mus musculus* similar to NADH dehydrogenase (LOC230075), mRNA | 12191 | −0.5 | D | −0.3 | D | YES |
| — | *Mus musculus* transcribed sequence with strong similarity to protein sp: P00722 (*E. coli*) BGAL_ECOLI Beta-galactosidase (Lactase) | 13872 | −0.6 | D | −0.3 | D | YES |
| — | *Mus musculus* transcribed sequence with strong similarity to protein pir: S68215 (*H. sapiens*) S68215 Mas 20 protein - human | 14271 | −0.6 | D | −0.7 | D | YES |
| — | *Mus musculus* transcribed sequence with weak similarity to protein sp: Q9Y3K8 (*H. sapiens*) GNGL_HUMAN Guanine nucleotide-binding protein G(I)/G(S)/G(O) gamma-5 like subunit | 14469 | −0.4 | D | −0.5 | D | YES |
| — | *Mus musculus* transcribed sequences | 14951 | −0.5 | D | −0.3 | D | YES |
| — | *Mus musculus* transcribed sequences | 15172 | −1.3 | D | −0.6 | D | YES |
| — | *Mus musculus* transcribed sequences | 15233 | −0.4 | D | −0.4 | D | YES |
| — | *Mus musculus* transcribed sequences | 15283 | −0.8 | D | −0.8 | D | YES |
| — | *Mus musculus* transcribed sequences | 15536 | −0.6 | D | −0.7 | D | YES |
| — | — | 15591 | −0.5 | D | −0.4 | D | YES |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymetrix Mouse Genome 430 2.0 Array

| Gene ID | Description | # | CR | Dir | OAA | Dir | Common |
|---|---|---|---|---|---|---|---|
| — | Mus musculus transcribed sequence with weak similarity to protein sp: P32456 (H. sapiens) GBP2_HUMAN Interferon-induced guanylate-binding protein 2 (Guanine nucleotide-binding protein 2) | 15668 | -2.6 | D | -0.9 | D | YES |
| — | Mus musculus similar to cytochrome P450 2B4 - rat (fragments) (LOC232993), mRNA | 15798 | -0.5 | D | -0.6 | D | YES |
| | | 17655 | -3.6 | D | -4.2 | D | YES |
| — | Mus musculus transcribed sequences | 18738 | -1.9 | D | -1.2 | D | YES |
| — | Mus musculus similar to glucosamine-6-phosphate deaminase (LOC381691), mRNA | 21421 | -1.2 | D | -0.5 | D | YES |
| — | Mus musculus similar to Cytochrome c, somatic (LOC384146), mRNA | 21459 | -0.8 | D | -0.6 | D | YES |
| — | Mus musculus transcribed sequences | 21852 | -0.5 | D | -0.3 | D | YES |
| | | 22028 | -0.4 | D | -0.4 | D | YES |
| | | 22122 | -0.4 | D | -0.4 | D | YES |
| — | Mus musculus adult male liver tumor cDNA, RIKEN full-length enriched library, clone: C730049O14 product:unknown EST, full insert sequence | 27836 | -0.7 | D | -0.3 | D | YES |
| — | Mus musculus transcribed sequences | 30047 | -0.4 | D | -0.6 | D | YES |
| | | 31861 | -0.5 | D | -0.6 | D | YES |
| — | Mus musculus transcribed sequences | 31941 | -0.7 | D | -0.5 | D | YES |
| | | 38789 | -0.6 | D | -0.5 | D | YES |
| — | Mus musculus transcribed sequences | 38815 | -2.9 | D | -0.7 | D | YES |
| — | Mus musculus adult male corpora quadrigemina cDNA, RIKEN full-length enriched library, clone: B230114P17 product:unknown EST, full insert sequence | 41400 | -1 | D | -0.8 | D | YES |
| — | Mus musculus similar to cadherin 19, type 2 preproprotein (LOC227485), mRNA | 42276 | -1.4 | D | -0.8 | D | YES |
| — | Mus musculus transcribed sequences | 43216 | -0.7 | D | -0.5 | D | YES |
| — | Mus musculus transcribed sequences | 45080 | -1.8 | D | -0.7 | D | YES |
| | | 43280 | -2.1 | D | -2.1 | D | YES |
| 0610012D09Rik | RIKEN cDNA 0610012D09 gene | 15468 | -0.5 | D | -0.5 | D | YES |
| 0610012H03Rik | RIKEN cDNA 0610012H03 gene | 39151 | -0.4 | D | -0.5 | D | YES |
| 0610016O18Rik | RIKEN cDNA 0610016O18 gene | 39221 | -0.6 | D | -0.6 | D | YES |
| 0610033L19Rik | RIKEN cDNA 0610033L19 gene | 10852 | -0.5 | D | -0.6 | D | YES |
| 0610039N19Rik | RIKEN cDNA 0610039N19 gene | 8975 | -0.5 | D | -0.7 | D | YES |
| 1110028A07Rik | RIKEN cDNA 1110028A07 gene | 19615 | -0.6 | D | -0.2 | D | YES |
| 1110067D22Rik | RIKEN cDNA 1110067D22 gene | 19440 | -1.8 | D | -0.6 | D | YES |
| 1200015F23Rik | RIKEN cDNA 1200015F23 gene | 12422 | -0.4 | D | -0.4 | D | YES |
| 1300014I06Rik | RIKEN cDNA 1300014I06 gene | 23234 | -0.2 | D | -0.3 | D | YES |
| 1600032L17Rik | RIKEN cDNA 1600032L17 gene | 23279 | -0.8 | D | -1.7 | D | YES |
| 1700124F02Rik | RIKEN cDNA 1700124F02 gene | 19675 | 0.6 | I | -0.3 | D | YES |
| 1810011O10Rik | RIKEN cDNA 1810011O10 gene | 19542 | -0.7 | D | -0.4 | D | YES |
| 1810023F06Rik | RIKEN cDNA 1810023F06 gene | 9379 | -1.5 | D | -0.6 | D | YES |
| 1810029G24Rik | RIKEN cDNA 1810029G24 gene | 22643 | -0.5 | D | -0.3 | D | YES |
| 1810044O22Rik | RIKEN cDNA 1810044O22 gene | 17020 | -0.6 | D | -0.3 | D | YES |
| 2010004N24Rik | RIKEN cDNA 2010004N24 gene | 12995 | -0.6 | D | -0.7 | D | YES |
| 2010306G19Rik | RIKEN cDNA 2010306G19 gene | 13304 | -0.8 | D | -0.3 | D | YES |
| 2310075C12Rik | RIKEN cDNA 2310075C12 gene | 16799 | -0.6 | D | -0.4 | D | YES |
| 2310076L09Rik | RIKEN cDNA 2310076L09 gene | 9196 | -0.4 | D | -0.6 | D | YES |
| 2310076L09Rik | RIKEN cDNA 2310076L09 gene | 32934 | -0.4 | D | -0.4 | D | YES |
| 2400006A19Rik | RIKEN cDNA 2400006A19 gene | 7955 | -0.5 | D | -0.3 | D | YES |
| 2410003B16Rik | RIKEN cDNA 2410003B16 gene | 27074 | -1.2 | D | -0.4 | D | YES |
| 2410013I23Rik | RIKEN cDNA 2410013I23 gene | 8383 | -0.6 | D | -0.5 | D | YES |
| 2510004L01Rik | RIKEN cDNA 2510004L01 gene | 5268 | -1.8 | D | -0.9 | D | YES |
| 2510004L01Rik | RIKEN cDNA 2510004L01 gene | 14650 | -2.1 | D | -0.6 | D | YES |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | | | |
|---|---|---|---|---|---|
| 2510006C20Rik | RIKEN cDNA 2510006C20 gene | 3469 | −0.5 | D | D | YES |
| 2600017P15Rik | RIKEN cDNA 2600017P15 gene | 12858 | −0.4 | D | D | YES |
| 2610030H06Rik | RIKEN cDNA 2610030H06 gene | 27347 | −0.6 | D | D | YES |
| 2610207I16Rik | RIKEN cDNA 2610207I16 gene | 11115 | −0.7 | D | D | YES |
| 2610318G18Rik | RIKEN cDNA 2610318G18 gene | 9041 | −0.8 | D | D | YES |
| 2900026G05Rik | RIKEN cDNA 2900026G05 gene | 15394 | −0.6 | D | D | YES |
| 3300001H21Rik | RIKEN cDNA 3300001H21 gene | 13914 | −0.4 | D | D | YES |
| 3930402F23Rik | RIKEN cDNA 3930402F23 gene | 2566 | −1.3 | D | D | YES |
| 4631422C05Rik | RIKEN cDNA 4631422C05 gene | 15552 | −0.4 | D | D | YES |
| 4733401N12Rik | RIKEN cDNA 4733401N12 gene | 22855 | −1 | D | D | YES |
| 4834411K15Rik | RIKEN cDNA 4834411K15 gene | 21763 | −0.9 | D | D | YES |
| 4833439L19Rik | RIKEN cDNA 4833439L19 gene | 16276 | −0.4 | D | D | YES |
| 4930469P12Rik | RIKEN cDNA 4930469P12 gene | 3391 | −0.2 | D | D | YES |
| 4931406C07Rik | RIKEN cDNA 4931406C07 gene | 21195 | −0.4 | D | D | YES |
| 4933433D23Rik | RIKEN cDNA 4933433D23 gene | 5094 | −0.5 | D | D | YES |
| 5033421K01Rik | RIKEN cDNA 5033421K01 gene | 10711 | 1.6 | I | I | YES |
| 5730494M16Rik | RIKEN cDNA 5730494M16 gene | 44727 | −1.3 | D | D | YES |
| 5730494N06Rik | RIKEN cDNA 5730494N06 gene | 20857 | −2.2 | D | D | YES |
| 5830413E08Rik | RIKEN cDNA 5830413E08 gene | 12475 | −0.3 | D | D | YES |
| 6030440G05Rik | RIKEN cDNA 6030440G05 gene | 15466 | −1.2 | D | D | YES |
| 6330587F24Rik | RIKEN cDNA 6330587F24 gene | 41583 | −0.7 | D | D | YES |
| 6430628I05Rik | RIKEN cDNA 6430628I05 gene | 8245 | −0.8 | D | D | YES |
| 6430628I05Rik | RIKEN cDNA 6430628I05 gene | 15190 | −0.8 | D | D | YES |
| 6530411B15Rik | RIKEN cDNA 6530411B15 gene | 8392 | −0.5 | D | D | YES |
| 9030624L02Rik | RIKEN cDNA 9030624L02 gene | 11396 | −0.7 | D | D | YES |
| 9130009C22Rik | RIKEN cDNA 9130009C22 gene | 10535 | −0.6 | D | D | YES |
| 9130019P20Rik | RIKEN cDNA 9130019P20 gene | 39136 | 2 | I | I | YES |
| 9630015D15Rik | RIKEN cDNA 9630015D15 gene | 27052 | −0.6 | D | D | YES |
| A430056A10Rik | RIKEN cDNA A430056A10 gene | 7814 | −2.6 | D | D | YES |
| A630025O09Rik | RIKEN cDNA A630025O09 gene | 30037 | −1 | D | D | YES |
| A930009M04Rik | RIKEN cDNA A930009M04 gene | 15355 | −0.8 | D | D | YES |
| AW539457 | expressed sequence AW539457 | 26927 | −1.8 | D | D | YES |
| BC005632 | cDNA sequence BC005632 | 148 | −0.3 | D | D | YES |
| BC023754 | cDNA sequence BC023754 | 11102 | 0.8 | I | I | YES |
| BC035295 | cDNA sequence BC035295 | 27518 | 1.1 | I | I | YES |
| Mice Fed Oxaloacetate with Genes Moving in Same Direction as Calorie Restricted Mice | | | | | | 356 |
| Mice Fed Oxaloacetate with Genes Moving in Opposite Direction as Calorie Restricted Mice | | | | | | 7 |
| Percentage of Mice Fed Oxaloacetate with Genes Moving in Same Direction as Calorie Restricted Mice | | | | | | 98.1% |

| Gene Ontology Biological Process | Gene Ontology Cellular Component | Gene Ontology Molecular Function | Pathway | InterPro |
|---|---|---|---|---|
| 8152 // metabolism // inferred from sequence or structural similarity | — | 3824 // catalytic activity // inferred from sequence or structural similarity /// 30729 // acetoacetate-CoA ligase activity; 1.03e−132 // extended:Unknown | 6.2.1.16; acetoacetate-CoA ligase | IPR000873 // AMP-dependent synthetase and ligase /// IPR005914 // Acetoacetyl-CoA synthase |
| 6810 // transport // inferred from electronic annotation | 5887 // integral to plasma membrane /// 16020 inferred from electronic annotation /// 4009 // | 166 // nucleotide binding // inferred from sequence or structural similarity /// 4009 // | | IPR003439 // ABC transporter /// IPR006162 // Phosphopantetheine |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | attachment site /// IPR003593 // AAA ATPase |
|---|---|---|---|
| 6725 // aromatic compound metabolism // inferred from sequence or structural similarity /// 6805 // xenobiotic metabolism /// 9636 // response to toxin // inferred from electronic annotation | // membrane // inferred from sequence or structural similarity /// 16021 // integral to membrane // traceable author statement | ATP-binding cassette (ABC) transporter activity // inferred from electronic annotation /// 5524 // ATP binding // inferred from electronic annotation | |
| | 16021 // integral to membrane // traceable author statement | 3824 // catalytic activity // inferred from sequence or structural similarity /// 16787 // hydrolase activity // inferred from electronic annotation | IPR000073 // Alpha/beta hydrolase fold /// IPR003089 // Alpha/beta hydrolase /// IPR000639 // Epoxide hydrolase /// IPR000379 // Esterase/lipase/thioesterase |
| 6631 // fatty acid metabolism // traceable author statement | 5777 // peroxisome // traceable author statement | 3985 // acetyl-CoA C-acetyltransferase activity // traceable author statement /// 3988 // acetyl-CoA C-acyltransferase activity // inferred from sequence or structural similarity /// 8415 // acyltransferase activity // inferred from sequence or structural similarity /// 16740 // transferase activity // inferred from sequence or structural similarity | Fatty acid biosynthesis (path 2) /// Fatty acid metabolism /// Bile acid biosynthesis /// Valine, leucine and isoleucine degradation /// Benzoate degradation via hydroxylation |
| | | | IPR002155 // Thiolase |
| 6470 // protein amino acid dephosphorylation // inferred from sequence or structural similarity | — | 3993 // acid phosphatase activity // inferred from electronic annotation /// 4725 // protein-tyrosine-phosphatase activity // inferred from sequence or structural similarity /// 4726 // non-membrane spanning protein tyrosine phosphatase activity // inferred from sequence or structural similarity /// 4727 // prenylated protein tyrosine phosphatase activity // inferred from sequence or structural similarity /// 16787 // hydrolase activity // inferred from electronic annotation | IPR000106 // Low molecular weight phosphotyrosine protein phosphatase /// IPR002115 // Mammalian LMW phosphotyrosine protein phosphatase |
| 7010 // cytoskeleton organization and biogenesis // inferred from electronic annotation | 5856 // cytoskeleton // inferred from electronic annotation | 5198 // structural molecule activity // inferred from electronic annotation /// 5200 // structural constituent of cytoskeleton // inferred from electronic annotation | Gene_Trap_Resource_2-04-02_Named_Genes /// IPR004000 // Actin/actin-like /// IPR004001 // Actin |
| 7010 // cytoskeleton organization and biogenesis // inferred from electronic annotation | 5856 // cytoskeleton // inferred from electronic annotation | 5200 // structural constituent of cytoskeleton // inferred from electronic annotation | IPR004000 // Actin/actin-like /// IPR004001 // Actin |
| 6508 // proteolysis and peptidolysis // inferred from electronic annotation /// 6957 // complement activation, alternative pathway // inferred from electronic annotation | 5615 // extracellular space // traceable author statement | 3817 // complement factor D activity // inferred from electronic annotation /// 4252 // serine-type endopeptidase activity // inferred from electronic annotation /// 4263 // chymotrypsin activity // inferred from electronic annotation /// 4295 // trypsin activity // inferred from electronic annotation /// 16787 // hydrolase activity // inferred from electronic annotation | IPR001254 // Peptidase S1, chymotrypsin /// IPR001314 // Peptidase S1A, chymotrypsin /// IPR009003 // Peptidase, trypsin-like serine and cysteine proteases |
| 6730 // one-carbon compound metabolism // inferred from sequence or structural similarity | — | 4013 // adenosylhomocysteinase activity // inferred from sequence or structural similarity /// 16787 // hydrolase activity // inferred from electronic annotation | IPR000043 // S-adenosyl-L-homocysteine hydrolase |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| Col 1 | Col 2 | Col 3 | Col 4 |
|---|---|---|---|
| — | inferred from sequence or structural similarity | — | IPR002213 // UDP-glucoronosyl/UDP-glucosyl transferase |
| — | — | — | IPR002213 // UDP-glucoronosyl/UDP-glucosyl transferase |
| — | — | — | IPR001395 // Aldo/keto reductase |
| — | 47042 // 1.1.1.50; 3-alpha-hydroxysteroid dehydrogenase (B-specific) activity; 8.56e-107 // extended: Unknown /// 47115 // 1.3.1.20; trans-1,2-dihydrobenzene-1,2-diol dehydrogenase activity; 4.2e-105 // extended: Unknown | — | — |
| 8152 // metabolism // inferred from electronic annotation | 4029 // aldehyde dehydrogenase (NAD) activity // inferred from electronic annotation /// 16491 // oxidoreductase activity // inferred from electronic annotation /// 4030 // 1.2.1.5; aldehyde dehydrogenase [NAD(P)+] activity; 1.39e-120 // extended: inferred from electronic annotation | 5783 // endoplasmic reticulum // inferred from electronic annotation /// 5792 // microsome // inferred from electronic annotation /// 16021 // integral to membrane // traceable author statement | IPR002086 // Aldehyde dehydrogenase |
| 7596 // blood coagulation // inferred from electronic annotation | 5509 // calcium ion binding // inferred from electronic annotation /// 5544 // calcium-dependent phospholipid binding // inferred from electronic annotation | — | IPR001464 // Annexin /// IPR002392 // Annexin, type V |
| 6118 // electron transport // inferred from sequence or structural similarity | — | — | IPR002937 // Amine oxidase /// IPR001327 // FAD-dependent pyridine nucleotide-disulphide oxidoreductase /// IPR000759 // Adrenodoxin reductase /// IPR003042 // Aromatic-ring hydroxylase /// IPR000205 // NAD-binding site /// IPR007526 // SWIRM /// IPR002888 // [2Fe—2S]-binding /// IPR001041 // Ferredoxin /// IPR002346 // Molybdopterin dehydrogenase, FAD-binding /// IPR000674 // Aldehyde oxidase and xanthine dehydrogenase, a/b hammerhead /// IPR008274 // Aldehyde oxidase and xanthine dehydrogenase, molybdopterin binding /// IPR005107 // CO dehydrogenase flavoprotein C-terminal domain /// IPR006058 // 2Fe—2S ferredoxin, iron-sulfur binding site /// IPR000572 // Oxidoreductase, molybdopterin binding |
| 6118 // electron transport // inferred from electronic annotation | 4031 // aldehyde oxidase activity // inferred from electronic annotation /// 5489 // electron transporter activity // inferred from electronic annotation /// 16491 // oxidoreductase activity // inferred from electronic annotation /// 30151 // molybdenum ion binding // inferred from electronic annotation /// 4854 // 1.1.1.204; xanthine dehydrogenase activity; 1e-300 // extended: inferred from electronic annotation /// 4855 // 1.1.3.22; xanthine oxidase activity; 1e-300 // extended: inferred from electronic annotation | — | — |
| 6810 // transport // inferred from electronic annotation /// 6886 // intracellular protein transport // traceable author statement /// 15031 // protein transport // inferred from electronic annotation | 8565 // protein transporter activity // inferred from electronic annotation | 5794 // Golgi apparatus // inferred from sequence or structural similarity /// 5802 // Golgi trans face // traceable author statement /// 30125 // clathrin vesicle coat // | IPR000804 // Clathrin adaptor complex, small chain /// IPR008733 // Peroxisomal biogenesis factor 11 |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| electronic annotation /// 16192 // vesicle-mediated transport // traceable author statement | inferred from sequence or structural similarity /// 30131 // clathrin adaptor complex // inferred from sequence or structural similarity | | |
| 6810 // transport // inferred from electronic annotation /// 6886 // intracellular protein transport // traceable author statement /// 15031 // protein transport // inferred from electronic annotation /// 16192 // vesicle-mediated transport // traceable author statement | 5794 // Golgi apparatus // inferred from sequence or structural similarity /// 5802 // Golgi trans face // traceable author statement /// 30125 // clathrin vesicle coat // inferred from sequence or structural similarity /// 30131 // clathrin adaptor complex // inferred from sequence or structural similarity | 8565 // protein transporter activity // inferred from electronic annotation | IPR000804 // Clathrin adaptor complex, small chain /// IPR008733 // Peroxisomal biogenesis factor 11 |
| 6869 // lipid transport // inferred from electronic annotation /// 30300 // regulation of cholesterol absorption // inferred from mutant phenotype | 5615 // extracellular space // traceable author statement | 5319 // lipid transporter activity // inferred from electronic annotation /// 8289 // lipid binding // inferred from electronic annotation | IPR000074 // Apolipoprotein A1/A4/E /// IPR009074 // Apolipoprotein A/E/C3 |
| 6869 // lipid transport // inferred from electronic annotation /// 30300 // regulation of cholesterol absorption // inferred from mutant phenotype | 5615 // extracellular space // traceable author statement | 5319 // lipid transporter activity // inferred from electronic annotation /// 8289 // lipid binding // inferred from electronic annotation | IPR000074 // Apolipoprotein A1/A4/E /// IPR009074 // Apolipoprotein A/E/C3 |
| — | — | — | IPR002110 // Ankyrin /// IPR001496 // SOCS protein, C-terminal |
| — | — | — | IPR002110 // Ankyrin /// IPR001496 // SOCS protein, C-terminal |
| 6754 // ATP biosynthesis // inferred from sequence or structural similarity /// 15992 // proton transport // inferred from sequence or structural similarity | — | 5524 // ATP binding // inferred from sequence or structural similarity /// 8553 // hydrogen-exporting ATPase activity, phosphorylative mechanism // inferred from sequence or structural similarity /// 15078 // hydrogen ion transporter activity // inferred from sequence or structural similarity /// 16787 // hydrolase activity // inferred from sequence or structural similarity | IPR004908 // V-ATPase subunit H /// IPR008938 // ARM repeat fold |
| 6355 // regulation of transcription, DNA-dependent // inferred from sequence or structural similarity | 5615 // extracellular space // traceable author statement /// 5622 // intracellular // inferred from sequence or structural similarity | 3700 // transcription factor activity // inferred from sequence or structural similarity /// 4437 // inositol/phosphatidylinositol phosphatase activity // inferred from sequence or structural similarity /// 8441 // 3'(2'),5'-bisphosphate nucleotidase activity // inferred from direct assay | IPR000760 // Inositol monophosphatase /// IPR000005 // Helix-turn-helix, AraC type |
| — | 16021 // integral to membrane // traceable author statement | 4416 // 3.1.2.6; hydroxyacylglutathione hydrolase activity; 1.03e-76 // extended: inferred from direct assay | IPR001279 // Beta-lactamase-like |
| 6355 // regulation of transcription, DNA-dependent // inferred from electronic annotation | 5634 // nucleus // inferred from electronic annotation /// 5667 // transcription factor complex // inferred from electronic annotation | 3700 // transcription factor activity // inferred from electronic annotation | Gene_Trap_Resource_2-04-02_Named_Genes |
| | | | IPR002715 // Nascent polypeptide-associated complex NAC /// IPR006311 // Twin-arginine |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | |
|---|---|---|
| 8151 // cell growth and/or maintenance // inferred from sequence or structural similarity /// 8283 // cell proliferation // inferred from sequence or structural similarity /// 8285 // negative regulation of cell proliferation // inferred from sequence or structural similarity | — | translocation pathway signal IPR002087 // Anti-proliferative protein annotation |
| — | — | IPR002087 // Anti-proliferative protein IPR004000 // Actin/actin-like /// IPR001611 // Leucine-rich repeat /// IPR003591 // Leucine-rich repeat, typical subtype |
| — | — | IPR006018 // Caldesmon and lymphocyte specific protein /// IPR006017 // Caldesmon /// IPR000533 // Tropomyosin |
| 7049 // cell cycle // inferred from direct assay /// 7186 // G-protein coupled receptor protein signaling pathway // inferred from sequence or structural similarity | 5737 // cytoplasm // inferred from sequence or structural similarity /// 5886 // plasma membrane // inferred from sequence or structural similarity | 5509 // calcium ion binding // traceable author statement /// 5515 // protein binding // inferred from sequence or structural similarity | G13_Signaling_Pathway /// G_Protein_Signaling | IPR002048 // Calcium-binding EF-hand /// IPR001125 // Recoverin |
| 6730 // one-carbon compound metabolism // inferred from electronic annotation | 5615 // extracellular space // traceable author statement /// 16021 // integral to membrane // traceable author statement | 4089 // carbonate dehydratase activity // inferred from electronic annotation /// 8270 // zinc ion binding // inferred from electronic annotation /// 16829 // lyase activity // inferred from electronic annotation | — | IPR001148 // Carbonic anhydrase, eukaryotic |
| 6333 // chromatin assembly/disassembly // inferred from sequence or structural similarity | 785 // chromatin // inferred from sequence or structural similarity /// 5634 // nucleus // inferred from electronic annotation /// 5654 // nucleoplasm // inferred from sequence or structural similarity /// 5720 // nuclear heterochromatin // inferred from sequence or structural similarity /// 5721 // centric heterochromatin // inferred from direct assay | 3682 // chromatin binding // inferred from sequence or structural similarity /// 5515 // protein binding // inferred from physical interaction | Gene_Trap_Resource_2-04-02_Named_Genes | IPR000953 // Chromo /// IPR008251 // Chromo shadow |
| 74 // regulation of cell cycle // inferred from electronic annotation /// 910 // cytokinesis // inferred from electronic annotation /// 7049 // cell cycle // inferred from electronic annotation /// 7067 // mitosis // inferred from electronic annotation | 5634 // nucleus // inferred from electronic annotation | 16538 // cyclin-dependent protein kinase regulator activity // inferred from electronic annotation | — | IPR006671 // Cyclin, N-terminal domain /// IPR006670 // Cyclin |
| 6457 // protein folding // inferred from electronic annotation | — | 3754 // chaperone activity // inferred from electronic annotation /// 5524 // ATP binding // inferred from electronic annotation | Gene_Trap_Resource_2-04-02_Named_Genes | IPR002423 // Chaperonin Cpn60/TCP-1 /// IPR001844 // Chaperonin Cpn60 /// IPR002194 // Chaperonin TCP-1 /// IPR008950 // GroEL-like chaperone, ATPase |
| — | 5886 // plasma membrane // inferred from electronic annotation /// 16021 // integral to membrane // traceable author statement | — | — | IPR000301 // CD9/CD37/CD63 antigen /// IPR000830 // Peripherin/rom-1 /// IPR008952 // Tetraspanin |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| — | 5615 // extracellular space // traceable author statement /// 16020 // membrane // inferred from sequence or structural similarity /// 16021 // integral to membrane // traceable author statement | 4872 // receptor activity // inferred from electronic annotation /// 5044 // scavenger receptor activity // inferred from sequence or structural similarity | IPR001190 // Speract/scavenger receptor |
| 6810 // transport // inferred from electronic annotation /// 7155 // cell adhesion // inferred from electronic annotation | 5764 // lysosome // inferred from electronic annotation /// 5886 // plasma membrane // inferred from electronic annotation /// 16020 // membrane // inferred from electronic annotation /// 16021 // integral to membrane // traceable author statement | 4872 // receptor activity // inferred from electronic annotation /// 5194 // cell adhesion molecule activity // inferred from sequence or structural similarity | IPR002159 // CD36 antigen /// IPR005428 // Adhesion molecule CD36 |
| 6810 // transport // inferred from electronic annotation /// 7155 // cell adhesion // inferred from electronic annotation | 5764 // lysosome // inferred from electronic annotation /// 5886 // plasma membrane // inferred from electronic annotation /// 16020 // membrane // inferred from electronic annotation /// 16021 // integral to membrane // traceable author statement | 4872 // receptor activity // inferred from electronic annotation /// 5194 // cell adhesion molecule activity // inferred from sequence or structural similarity | IPR002159 // CD36 antigen /// IPR005428 // Adhesion molecule CD36 |
| 6810 // transport // inferred from electronic annotation /// 7155 // cell adhesion // inferred from electronic annotation | 5764 // lysosome // inferred from electronic annotation /// 5886 // plasma membrane // inferred from electronic annotation /// 16020 // membrane // inferred from electronic annotation /// 16021 // integral to membrane // traceable author statement | 4872 // receptor activity // inferred from electronic annotation /// 5194 // cell adhesion molecule activity // inferred from sequence or structural similarity | IPR002159 // CD36 antigen /// IPR005428 // Adhesion molecule CD36 |
| — | 5615 // extracellular space // traceable author statement /// 5886 // plasma membrane // inferred from electronic annotation | Gene_Trap_Resource_2-04-02_Named_Genes | IPR003632 // Cell-surface glycoprotein Ly-6/CD59 /// IPR001526 // CD59 antigen |
| — | 5615 // extracellular space // traceable author statement /// 5886 // plasma membrane // inferred from electronic annotation | Gene_Trap_Resource_2-04-02_Named_Genes | IPR003632 // Cell-surface glycoprotein Ly-6/CD59 /// IPR001526 // CD59 antigen |
| 910 // cytokinesis // inferred from electronic annotation /// 7015 // actin filament organization // inferred from sequence or structural similarity /// 7264 // small GTPase mediated signal transduction // inferred from sequence or structural similarity /// 7266 // Rho protein signal transduction // traceable author statement | 30175 // filopodium // inferred from sequence or structural similarity | 3924 // GTPase activity // traceable author statement /// 3925 // small monomeric GTPase activity // inferred from sequence or structural similarity /// 3931 // Rho small monomeric GTPase activity // inferred from sequence or structural similarity /// 5515 // protein binding // inferred from physical interaction /// 5525 // GTP binding // inferred from electronic annotation | G13_Signaling_Pathway /// Gene_Trap_Resource_2-04-02_Named_Genes | IPR001806 // Ras GTPase superfamily /// IPR003578 // Ras small GTPase, Rho type /// IPR005225 // Small GTP-binding protein domain /// IPR003577 // Ras small GTPase, Ras type /// IPR003579 // Ras small GTPase, Rab type |
| — | 5615 // extracellular space // traceable author statement /// 5783 // endoplasmic reticulum // inferred from sequence or structural similarity | 3824 // catalytic activity // inferred from sequence or structural similarity /// 4091 // carboxylesterase activity // inferred from sequence or structural similarity /// 4759 // serine esterase activity // inferred from sequence or structural similarity /// 16787 // hydrolase activity // inferred from electronic annotation /// 16789 // carboxylic ester hydrolase activity // inferred from sequence or structural similarity | IPR002018 // Carboxylesterase, type B /// IPR000379 // Esterase/lipase/thioesterase |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | 5615 // protein binding // inferred from sequence or structural similarity | | IPR000408 // Regulator of chromosome condensation, RCC1 /// IPR000210 // BTB/POZ domain /// IPR009091 // Regulator of chromosome condensation/beta-lactamase-inhibitor protein // |
|---|---|---|---|
| 8654 // CDP-OH_P_transf; phospholipid biosynthesis; 4.2e-17 // extended: inferred from electronic annotation | | | IPR000462 // CDP-alcohol phosphatidyltransferase /// IPR003016 // 2-oxo acid dehydrogenase, lipoyl-binding site |
| | | | IPR000462 // CDP-alcohol phosphatidyltransferase /// IPR003016 // 2-oxo acid dehydrogenase, lipoyl-binding site |
| 6935 // chemotaxis // inferred from electronic annotation | 16020 // membrane // inferred from electronic annotation /// 16021 // integral to membrane // inferred from electronic annotation | 5125 // cytokine activity // inferred from electronic annotation | IPR008253 // Marvel |
| 7162 // negative regulation of cell adhesion // inferred from sequence or structural similarity | 5615 // NOT extracellular space // inferred from sequence or structural similarity /// 5783 // endoplasmic reticulum // inferred from sequence or structural similarity /// 5794 // Golgi apparatus // inferred from sequence or structural similarity /// 16021 // integral to membrane // traceable author statement | 8080 // N-acetyltransferase activity // inferred from sequence or structural similarity /// 16740 // transferase activity // inferred from electronic annotation | IPR000182 // GCN5-related N-acetyltransferase |
| 6355 // regulation of transcription, DNA-dependent // inferred from electronic annotation /// 6695 // cholesterol biosynthesis // inferred from sequence or structural similarity /// 8284 // positive regulation of cell proliferation // inferred from direct assay /// 45944 // positive regulation of transcription from Pol II promoter // inferred from direct assay /// 6939 // smooth muscle contraction // inferred from sequence or structural similarity | 5634 // nucleus // inferred from direct assay /// 5783 // endoplasmic reticulum // inferred from direct assay /// 5829 // cytosol // inferred from direct assay | 3676 // nucleic acid binding // inferred from electronic annotation /// 3677 // DNA binding // inferred from electronic annotation /// 3700 // transcription factor activity // inferred from sequence or structural similarity | IPR001878 // Zn-finger, CCHC type |
| | | 3779 // actin binding // inferred from sequence or structural similarity /// 5516 // calmodulin binding // inferred from sequence or structural similarity | IPR000557 // Calponin repeat /// IPR003096 // SM22/calponin /// IPR001997 // Calponin /// IPR003247 // Calponin-like actin-binding subtype /// IPR001715 // Calponin-like actin-binding |
| 7155 // cell adhesion // inferred from electronic annotation | 5578 // extracellular matrix // inferred from electronic annotation /// 5581 // collagen // inferred from electronic annotation | 5201 // extracellular matrix structural constituent // inferred from electronic annotation /// 30020 // extracellular matrix structural constituent conferring tensile strength // inferred from electronic annotation | Inflammatory_Response_Pathway IPR008161 // Collagen helix repeat /// IPR000885 // Fibrillar collagen, C-terminal /// IPR008160 // Collagen triple helix repeat /// IPR001007 // von Willebrand factor, type C /// IPR002181 // Fibrinogen, beta/gamma chain, C-terminal globular |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| Column 1 | Column 2 | Column 3 | Column 4 |
|---|---|---|---|
| 7423 // sensory organ development // inferred from electronic annotation | 5737 // cytoplasm // inferred from electronic annotation | 3960 // NADPH:quinone reductase activity // inferred from electronic annotation /// 4024 // alcohol dehydrogenase activity, zinc-dependent // inferred from electronic annotation /// 5212 // structural constituent of eye lens // inferred from electronic annotation /// 8270 // zinc ion binding // inferred from electronic annotation /// 16491 // oxidoreductase activity // inferred from electronic annotation | — | IPR002085 // Zinc-containing alcohol dehydrogenase superfamily /// IPR002364 // Quinone oxidoreductase/zeta-crystallin |
| 6376 // mRNA splice site selection // inferred from direct assay | 5634 // nucleus // inferred from sequence or structural similarity | 8248 // pre-mRNA splicing factor activity // inferred from direct assay /// 3676 // rrm; nucleic acid binding; 2.3e−09 // extended: inferred from electronic annotation | — | IPR000504 // RNA-binding region RNP-1 (RNA recognition motif) /// IPR002343 // Paraneoplastic encephalomyelitis antigen |
| — | 5615 // extracellular space // traceable author statement /// 16021 // integral to membrane // traceable author statement | 4872 // receptor activity // inferred from electronic annotation | — | IPR007110 // Immunoglobulin-like /// IPR003598 // Immunoglobulin C-2 type /// IPR003599 // Immunoglobulin subtype /// IPR003596 // Immunoglobulin V-type |
| 6118 // electron transport // inferred from electronic annotation /// 6700 // C21-steroid hormone biosynthesis // inferred from electronic annotation | 5615 // extracellular space // traceable author statement /// 16020 // membrane // inferred from electronic annotation | 4497 // monooxygenase activity // inferred from electronic annotation /// 4508 // steroid 17-alpha-monooxygenase activity // inferred from electronic annotation /// 16491 // oxidoreductase activity // inferred from electronic annotation | Glucocorticoid_Mineralo corticoid_Metabolism /// Steroid_Biosynthesis | IPR001128 // Cytochrome P450 /// IPR002401 // E-class P450, group I |
| 6118 // electron transport // inferred from electronic annotation | 5783 // endoplasmic reticulum // inferred from electronic annotation /// 5792 // microsome // inferred from electronic annotation /// 16020 // membrane // inferred from electronic annotation | 4497 // monooxygenase activity // inferred from electronic annotation /// 16491 // oxidoreductase activity // inferred from electronic annotation /// 16712 // oxidoreductase activity, acting on paired donors, with incorporation or reduction of molecular oxygen, reduced flavin or flavoprotein as one donor, and incorporation of one atom of oxygen // inferred from electronic annotation | — | IPR001128 // Cytochrome P450 /// IPR002401 // E-class P450, group I /// IPR008068 // E-class P450, CYP2B |
| 6118 // electron transport // inferred from electronic annotation | 5783 // endoplasmic reticulum // inferred from electronic annotation /// 5792 // microsome // inferred from electronic annotation /// 16020 // membrane // inferred from electronic annotation | 4497 // monooxygenase activity // inferred from electronic annotation /// 16491 // oxidoreductase activity // inferred from electronic annotation /// 16712 // oxidoreductase activity, acting on paired donors, with incorporation or reduction of molecular oxygen, reduced flavin or flavoprotein as one donor, and incorporation of one atom of oxygen // inferred from electronic annotation | — | IPR001128 // Cytochrome P450 /// IPR002401 // E-class P450, group I /// IPR008068 // E-class P450, CYP2B |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| 6118 // electron transport // inferred from electronic annotation | 5783 // endoplasmic reticulum // inferred from electronic annotation /// 5792 // microsome // inferred from electronic annotation /// 16020 // membrane // inferred from electronic annotation | 4497 // monooxygenase activity // inferred from electronic annotation /// 16491 // oxidoreductase activity // inferred from electronic annotation /// 16712 // oxidoreductase activity, acting on paired donors, with incorporation or reduction of molecular oxygen, reduced flavin or flavoprotein as one donor, and incorporation of one atom of oxygen // inferred from electronic annotation | — | IPR001128 // Cytochrome P450 /// IPR002401 // E-class P450, group I /// IPR008068 // E-class P450, CYP2B |
| 6118 // electron transport // inferred from electronic annotation | 5783 // endoplasmic reticulum // inferred from electronic annotation /// 5792 // microsome // inferred from electronic annotation /// 16020 // membrane // inferred from electronic annotation | 4497 // monooxygenase activity // inferred from electronic annotation /// 16491 // oxidoreductase activity // inferred from electronic annotation /// 16712 // oxidoreductase activity, acting on paired donors, with incorporation or reduction of molecular oxygen, reduced flavin or flavoprotein as one donor, and incorporation of one atom of oxygen // inferred from electronic annotation | — | IPR001128 // Cytochrome P450 /// IPR002401 // E-class P450, group I /// IPR008068 // E-class P450, CYP2B |
| 6118 // electron transport // inferred from electronic annotation | 5783 // endoplasmic reticulum // inferred from electronic annotation /// 5792 // microsome // inferred from electronic annotation /// 16020 // membrane // inferred from electronic annotation | 4497 // monooxygenase activity // inferred from electronic annotation /// 16491 // oxidoreductase activity // inferred from electronic annotation | — | IPR001128 // Cytochrome P450 /// IPR002401 // E-class P450, group I |
| 6118 // electron transport // inferred from electronic annotation | 5615 // extracellular space // traceable author statement /// 5783 // endoplasmic reticulum // inferred from electronic annotation /// 5792 // microsome // inferred from electronic annotation /// 16020 // membrane // inferred from electronic annotation | 4497 // monooxygenase activity // inferred from electronic annotation /// 16491 // oxidoreductase activity // inferred from electronic annotation /// 16712 // oxidoreductase activity, acting on paired donors, with incorporation or reduction of molecular oxygen, reduced flavin or flavoprotein as one donor, and incorporation of one atom of oxygen // inferred from electronic annotation | — | IPR001128 // Cytochrome P450 /// IPR002401 // E-class P450, group I /// IPR008071 // E-class P450, CYP2J |
| 6118 // electron transport // inferred from electronic annotation | 5615 // extracellular space // traceable author statement /// 5783 // endoplasmic reticulum // inferred from electronic annotation /// 5792 // microsome // inferred from electronic annotation /// 16020 // membrane // inferred from electronic annotation | 4497 // monooxygenase activity // inferred from electronic annotation /// 16491 // oxidoreductase activity // inferred from electronic annotation /// 16712 // oxidoreductase activity, acting on paired donors, with incorporation or reduction of molecular oxygen, reduced flavin or flavoprotein as one donor, and incorporation of one atom of oxygen // inferred from electronic annotation | — | IPR001128 // Cytochrome P450 /// IPR002401 // E-class P450, group I /// IPR008071 // E-class P450, CYP2J |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| — | 5783 // endoplasmic reticulum // inferred from sequence or structural similarity /// 16021 // integral to membrane // traceable author statement | 4497 // monooxygenase activity // inferred from electronic annotation /// 16491 // oxidoreductase activity // inferred from electronic annotation /// 18685 // alkane 1-monooxygenase activity // inferred from sequence or structural similarity | IPR001128 // Cytochrome P450 /// IPR002401 // E-class P450, group I /// IPR002402 // E-class P450, group II |
| 6118 // electron transport // inferred from electronic annotation /// 8203 // cholesterol metabolism // inferred from electronic annotation | 5783 // endoplasmic reticulum // inferred from electronic annotation /// 5792 // microsome // inferred from electronic annotation /// 16020 // membrane // inferred from electronic annotation /// 16021 // integral to membrane // traceable author statement | 4497 // monooxygenase activity // inferred from electronic annotation /// 8123 // cholesterol 7-alpha-monooxygenase activity // inferred from electronic annotation /// 16491 // oxidoreductase activity // inferred from electronic annotation | IPR001128 // Cytochrome P450 /// IPR002403 // E-class P450, group IV |
| 6412 // protein biosynthesis // inferred from sequence or structural similarity | 5840 // ribosome // inferred from sequence or structural similarity | 3735 // structural constituent of ribosome // inferred from sequence or structural similarity | — IPR004038 // Ribosomal protein L7Ae/L30e/S12e/Gadd45 /// IPR004037 // Ribosomal protein L7AE /// IPR002415 // High mobility group-like nuclear protein |
| 6118 // electron transport // inferred from sequence or structural similarity | — | 5489 // electron transporter activity // inferred from sequence or structural similarity | IPR010357 // Eukaryotic protein of unknown function DUF953 /// IPR006662 // Thioredoxin type domain /// IPR006663 // Thioredoxin domain 2 /// IPR007484 // Peptidase M28 |
| 7165 // signal transduction // inferred from sequence or structural similarity | 5615 // extracellular space // traceable author statement /// 5739 // mitochondrion // inferred from sequence or structural similarity | 4673 // protein-histidine kinase activity // inferred from sequence or structural similarity /// 5524 // ATP binding // inferred from sequence or structural similarity /// 16301 // kinase activity // inferred from sequence or structural similarity /// 16740 // transferase activity // inferred from sequence or structural similarity | IPR003594 // ATP-binding region, ATPase-like /// IPR005467 // Histidine kinase |
| — | 5615 // extracellular space // traceable author statement /// 16021 // integral to membrane // traceable author statement | 4740 // [pyruvate dehydrogenase (lipoamide)] kinase activity // inferred from sequence or structural similarity | — |
| — | — | 5215 // sugar_tr; transporter activity; 3.3e–06 // extended: inferred from electronic annotation | IPR005828 // General substrate transporter /// IPR007114 // Major facilitator superfamily /// IPR000413 // Integrins alpha chain |
| 6520 // amino acid metabolism // inferred from electronic annotation /// 42423 // catecholamine biosynthesis // inferred from electronic annotation | — | 4058 // aromatic-L-amino-acid decarboxylase activity // inferred from electronic annotation /// 16829 // lyase activity // inferred from electronic annotation /// 16831 // carboxy-lyase activity // inferred from electronic annotation | Gene_Trap_Resource_2-04-02_IMAGE_and_RIKEN_cDNAs Catecholamine_Biosynthesis IPR002129 // Pyridoxal-dependent decarboxylase |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | |
|---|---|---|
| — | 5622 // intracellular // inferred from sequence or structural similarity | 3677 // DNA binding // inferred from sequence or structural similarity |
| — | 5622 // intracellular // inferred from sequence or structural similarity | 3677 // DNA binding // inferred from sequence or structural similarity |
| — | — | 8415 // acyltransferase activity // inferred from electronic annotation /// 16740 // transferase activity // inferred from electronic annotation | IPR007130 // Diacylglycerol acyltransferase /// IPR006662 // Thioredoxin type domain |
| — | 5615 // extracellular space // traceable author statement /// 16021 // integral to membrane // inferred from electronic annotation | 4800 // thyroxine 5'-deiodinase activity // inferred from electronic annotation /// 16491 // oxidoreductase activity // inferred from electronic annotation /// 16787 // hydrolase activity // inferred from electronic annotation | IPR000643 // Iodothyronine deiodinase /// IPR008261 // Iodothyronine deiodinase, active site |
| — | 5856 // cytoskeleton // inferred from electronic annotation /// 45202 // synapse // inferred from direct assay | 3779 // actin binding // inferred from electronic annotation /// 5198 // structural molecule activity // inferred from electronic annotation /// 5509 // calcium ion binding // inferred from electronic annotation /// 8270 // zinc ion binding // inferred from electronic annotation | IPR001715 // Calponin-like actin-binding /// IPR001202 // WW/Rsp5/WWP domain /// IPR002017 // Spectrin repeat /// IPR000433 // Zn-finger, ZZ type /// IPR001589 // Actin-binding, actinin-type |
| 6508 // proteolysis and peptidolysis // inferred from electronic annotation | 16020 // membrane // inferred from electronic annotation /// 16021 // integral to membrane // traceable author statement /// 46581 // intercellular canaliculus // inferred from direct assay | 3824 // catalytic activity // inferred from electronic annotation /// 4177 // aminopeptidase activity // inferred from electronic annotation /// 4252 // serine-type endopeptidase activity // inferred from electronic annotation /// 4274 // dipeptidyl-peptidase IV activity // inferred from electronic annotation /// 4287 // prolyl oligopeptidase activity // inferred from electronic annotation /// 8236 // serine-type peptidase activity // inferred from electronic annotation /// 16787 // hydrolase activity // inferred from electronic annotation | IPR001375 // Peptidase S9, prolyl oligopeptidase active site region /// IPR002469 // Peptidase S9B, dipeptidylpeptidase IV N-terminal /// IPR002471 // Peptidase S9, serine active site /// IPR000379 // Esterase/lipase/thioesterase |
| 6470 // protein amino acid dephosphorylation // inferred from electronic annotation /// 7049 // cell cycle // inferred from electronic annotation | — | 4721 // phosphoprotein phosphatase activity // inferred from electronic annotation /// 4725 // protein-tyrosine-phosphatase activity // inferred from electronic annotation /// 8138 // protein tyrosine/serine/threonine phosphatase activity // inferred from electronic annotation /// 16787 // hydrolase activity // inferred from electronic annotation /// 17017 // MAP kinase phosphatase activity // inferred from electronic annotation | IPR001763 // Rhodanese-like /// IPR000340 // Dual specificity protein phosphatase /// IPR008343 // MAP kinase phosphatase /// IPR000387 // Tyrosine specific protein phosphatase and dual specificity protein phosphatase |
| — | 16021 // integral to membrane // traceable author statement | 5198 // structural molecule activity // inferred from sequence or structural similarity | IPR002049 // Laminin-type EGF-like domain /// IPR006209 // EGF-like domain /// IPR006210 // Type I EGF /// IPR009030 // Growth factor, receptor |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | |
|---|---|---|
| 74 // regulation of cell cycle // inferred from electronic annotation /// 902 // cellular morphogenesis // inferred from sequence or structural similarity /// 6468 // protein amino acid phosphorylation // inferred from electronic annotation /// 7165 // signal transduction // inferred from direct assay /// 7169 // transmembrane receptor protein tyrosine kinase signaling pathway // inferred from electronic annotation /// 7173 // EGF receptor signaling pathway // inferred from sequence or structural similarity /// 8151 // cell growth and/or maintenance // inferred from electronic annotation /// 8283 // cell proliferation // inferred from sequence or structural similarity /// 50730 // regulation of peptidyl-tyrosine phosphorylation // inferred from mutant phenotype | 5615 // extracellular space // traceable author statement /// 5622 // intracellular // inferred from direct assay /// 5768 // endosome // inferred from sequence or structural similarity /// 5856 // cytoskeleton // inferred from sequence or structural similarity /// 5886 // plasma membrane // inferred from sequence or structural similarity /// 5887 // integral to plasma membrane // inferred from sequence or structural similarity /// 16020 // membrane // inferred from electronic annotation /// 16021 // integral to membrane // traceable author statement /// 30139 // endocytic vesicle // inferred from direct assay | 4672 // protein kinase activity // inferred from electronic annotation /// 4674 // protein serine/threonine kinase activity // inferred from sequence or structural similarity /// 4713 // protein-tyrosine kinase activity // inferred from electronic annotation /// 4714 // transmembrane receptor protein tyrosine kinase activity // inferred from electronic annotation /// 4871 // signal transducer activity // inferred from direct assay /// 4872 // receptor activity // inferred from electronic annotation /// 5006 // epidermal growth factor receptor activity // inferred from electronic annotation /// 5515 // protein binding // inferred from physical interaction /// 5524 // ATP binding // inferred from electronic annotation /// 16301 // kinase activity // inferred from electronic annotation /// 16740 // transferase activity // inferred from electronic annotation | IPR000719 // Protein kinase /// IPR006211 // Furin-like cysteine rich region /// IPR000494 // Epidermal growth-factor receptor (EGFR), L domain /// IPR001245 // Tyrosine protein kinase /// IPR001450 // 4Fe—4S ferredoxin, iron-sulfur binding domain /// IPR008266 // Tyrosine protein kinase, active site /// IPR000345 // Cytochrome c heme-binding site /// IPR006212 // Furin-like repeat /// IPR009030 // Growth factor, receptor |
| 6355 // regulation of transcription, DNA-dependent // inferred from mutant phenotype /// 46652 // thymocyte differentiation // inferred from mutant phenotype | 5634 // nucleus // inferred from mutant phenotype | 3676 // nucleic acid binding // inferred from electronic annotation /// 3677 // DNA binding // inferred from electronic annotation /// 3700 // transcription factor activity // inferred from mutant phenotype | Ovarian_Infertility_Genes | IPR007087 // Zn-finger, C2H2 type |
| 30497 // fatty acid elongation // inferred from direct assay | 16021 // integral to membrane // traceable author statement /// 30176 // integral to endoplasmic reticulum membrane // inferred from electronic annotation | — | IPR010844 // Occludin and RNA polymerase II elongation factor ELL IPR002076 // GNS1/SUR4 membrane protein |
| 30497 // fatty acid elongation // inferred from direct assay | 16021 // integral to membrane // traceable author statement /// 30176 // integral to endoplasmic reticulum membrane // inferred from electronic annotation | 16747 // transferase activity, transferring groups other than amino-acyl groups // inferred from direct assay | IPR002076 // GNS1/SUR4 membrane protein |
| — | 5615 // extracellular space // traceable author statement /// 5783 // endoplasmic reticulum // inferred from electronic annotation /// 5886 // plasma membrane // inferred from electronic annotation /// 16021 // integral to membrane // inferred from electronic annotation | 16747 // transferase activity, transferring groups other than amino-acyl groups // inferred from direct assay | IPR000407 // Nucleoside phosphatase GDA1/CD39 |
| — | 5615 // extracellular space // traceable author statement /// 5783 // endoplasmic reticulum // inferred from electronic annotation /// 5886 // plasma membrane // inferred from electronic annotation /// 16021 // integral to membrane // inferred from electronic annotation | 287 // magnesium ion binding // inferred from electronic annotation /// 16787 // hydrolase activity // inferred from electronic annotation | IPR000407 // Nucleoside phosphatase GDA1/CD39 |
| — | 5615 // extracellular space // traceable author statement /// 5783 // endoplasmic reticulum // inferred from electronic annotation /// 5886 // plasma membrane // inferred from electronic annotation /// 16021 // integral to membrane // inferred from electronic annotation | 287 // magnesium ion binding // inferred from electronic annotation /// 16787 // hydrolase activity // inferred from electronic annotation | IPR000407 // Nucleoside phosphatase GDA1/CD39 |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| 6508 // proteolysis and peptidolysis // inferred from sequence or structural similarity /// 6805 // xenobiotic metabolism // inferred from electronic annotation /// 9636 // response to toxin // inferred from electronic annotation | 5615 // extracellular space // traceable author statement /// 5783 // endoplasmic reticulum // inferred from electronic annotation /// 5792 // microsome // inferred from electronic annotation /// 16021 // integral to membrane // inferred from electronic annotation | 3824 // catalytic activity // inferred from electronic annotation /// 4177 // aminopeptidase activity // inferred from sequence or structural similarity /// 4301 // epoxide hydrolase activity // inferred from electronic annotation /// 16787 // hydrolase activity // inferred from electronic annotation | | IPR000073 // Alpha/beta hydrolase fold /// IPR010497 // Epoxide hydrolase, N-terminal /// IPR000639 // Epoxide hydrolase /// IPR000379 // Esterase/lipase/thioesterase |
| 6810 // transport // inferred from electronic annotation | — | 5215 // transporter activity // inferred from electronic annotation /// 5488 // binding // inferred from electronic annotation /// 8289 // lipid binding // inferred from electronic annotation | | IPR000566 // Lipocalin-related protein and Bos/Can/Equ allergen /// IPR000463 // Cytosolic fatty-acid binding protein |
| 6810 // transport // inferred from electronic annotation | — | 5215 // transporter activity // inferred from electronic annotation /// 5488 // binding // inferred from electronic annotation /// 8289 // lipid binding // inferred from electronic annotation | | IPR000566 // Lipocalin-related protein and Bos/Can/Equ allergen /// IPR000463 // Cytosolic fatty-acid binding protein |
| 6810 // transport // inferred from electronic annotation | — | 5215 // transporter activity // inferred from electronic annotation /// 5488 // binding // inferred from electronic annotation /// 8289 // lipid binding // inferred from electronic annotation | | IPR000566 // Lipocalin-related protein and Bos/Can/Equ allergen /// IPR000463 // Cytosolic fatty-acid binding protein |
| 6810 // transport // inferred from electronic annotation | — | 5215 // transporter activity // inferred from electronic annotation /// 5488 // binding // inferred from electronic annotation /// 8289 // lipid binding // inferred from electronic annotation | | IPR000566 // Lipocalin-related protein and Bos/Can/Equ allergen /// IPR000463 // Cytosolic fatty-acid binding protein |
| 6633 // fatty acid biosynthesis // inferred from electronic annotation /// 9058 // biosynthesis // inferred from electronic annotation | — | 3824 // catalytic activity // inferred from electronic annotation /// 4024 // alcohol dehydrogenase activity, zinc-dependent // inferred from electronic annotation /// 4312 // fatty-acid synthase activity // inferred from electronic annotation /// 8270 // zinc ion binding // inferred from electronic annotation /// 8415 // acyltransferase activity // inferred from electronic annotation /// 16491 // oxidoreductase activity // inferred from electronic annotation /// 16740 // transferase activity // inferred from electronic annotation /// 16787 // hydrolase activity // inferred from electronic annotation /// 16788 // hydrolase activity, acting on ester bonds // inferred from electronic annotation /// 16829 // lyase activity // inferred from electronic annotation /// 4315 // 2.3.1.41; 3-oxoacyl-[acyl-carrier protein] synthase activity; 1e−300 // extended: inferred from electronic | Fatty_Acid_Synthesis | IPR002085 // Zinc-containing alcohol dehydrogenase superfamily /// IPR006163 // Phosphopantetheine-binding domain /// IPR001031 // Thioesterase /// IPR006162 // Phosphopantetheine attachment site /// IPR000794 // Beta-ketoacyl synthase /// IPR009081 // Acyl carrier protein-like /// IPR001227 // Acyl transferase domain /// IPR000051 // SAM (and some other nucleotide) binding motif |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| — | annotation /// 4316 // 1.1.1.100; 3-oxoacyl-[acyl-carrier protein] reductase activity; 1e−300 // extended: Unknown /// 4319 // 1.3.1.10; enoyl-[acyl-carrier protein] reductase (NADPH, B-specific) activity; 1e−300 // extended: inferred from electronic annotation /// 16297 // 3.1.2.14; acyl-[acyl-carrier protein] hydrolase activity; 1e−300 // extended: inferred from physical interaction 3676 // rrm; nucleic acid binding; 1.5e−05 // extended: inferred from electronic annotation | — | IPR000504 // RNA-binding region RNP-1 (RNA recognition motif) /// IPR006536 // HnRNP-L/PTB/hephaestus splicing factor /// IPR001810 // Cyclin-like F-box /// IPR007397 // F-box associated region /// IPR008945 // Skp1-Skp2 dimerisation |
| 7257 // activation of JUNK // inferred from sequence or structural similarity /// 30032 // lamellipodium biogenesis // inferred from direct assay /// 30035 // microspike biogenesis // inferred from direct assay | 30027 // lamellipodium // inferred from direct assay /// 30175 // filopodium // inferred from direct assay | 3779 // actin binding // inferred from sequence or structural similarity | IPR000219 // DH domain /// IPR001849 // Pleckstrin-like /// IPR000306 // Zn-finger, FYVE type /// IPR007087 // Zn-finger, C2H2 type |
| 6457 // protein folding // inferred from electronic annotation /// 6810 // transport // inferred from sequence or structural similarity | 16020 // membrane // inferred from sequence or structural similarity | 3755 // peptidyl-prolyl cis-trans isomerase activity // inferred from electronic annotation /// 4009 // ATP-binding cassette (ABC) transporter activity // inferred from sequence or structural similarity /// 5524 // ATP binding // inferred from sequence or structural similarity /// 5528 // FK506 binding // inferred from sequence or structural similarity /// 16853 // isomerase activity // inferred from electronic annotation | IPR001179 // Peptidylprolyl isomerase, FKBP-type /// IPR003439 // ABC transporter |
| 6118 // electron transport // inferred from electronic annotation | 5792 // microsome // inferred from electronic annotation /// 16021 // integral to membrane // traceable author statement | 4497 // monooxygenase activity // inferred from electronic annotation /// 4499 // dimethylaniline monooxygenase (N-oxide-forming) activity // inferred from electronic annotation /// 15036 // disulfide oxidoreductase activity // inferred from electronic annotation /// 16491 // oxidoreductase activity // inferred from electronic annotation | IPR000960 // Flavin-containing monooxygenase FMO /// IPR001327 // FAD-dependent pyridine nucleotide-disulphide oxidoreductase /// IPR000759 // Adrenodoxin reductase /// IPR002257 // Flavin-containing monooxygenase (FMO) 5 /// IPR009057 // Homeodomain-like |
| 6355 // regulation of transcription, DNA-dependent // inferred from electronic annotation | 5634 // nucleus // inferred from electronic annotation /// 5667 // transcription factor complex // inferred from electronic annotation | 3677 // DNA binding // inferred from electronic annotation /// 3700 // transcription factor activity // inferred from electronic annotation | IPR001766 // Fork head transcription factor /// IPR009058 // Winged helix DNA-binding |

— TGF_Beta_Signaling_Pathway

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| Col1 | Col2 | Col3 | Col4 |
|---|---|---|---|
| 1678 // cell glucose homeostasis // inferred from mutant phenotype /// 6355 // regulation of transcription, DNA-dependent // inferred from mutant phenotype /// 9267 // cellular response to starvation // inferred from mutant phenotype | 5634 // nucleus // inferred from electronic annotation /// 5667 // transcription factor complex // inferred from electronic annotation | 3677 // DNA binding // inferred from electronic annotation /// 3700 // transcription factor activity // inferred from electronic annotation /// 30528 // transcription regulator activity // inferred from mutant phenotype | IPR001766 // Fork head transcription factor /// IPR009058 // Winged helix DNA-binding |
| 6355 // regulation of transcription, DNA-dependent // inferred from electronic annotation | 5634 // nucleus // inferred from electronic annotation /// 5667 // transcription factor complex // inferred from electronic annotation | 3677 // DNA binding // inferred from electronic annotation /// 3700 // transcription factor activity // inferred from electronic annotation | IPR001766 // Fork head transcription factor /// IPR009058 // Winged helix DNA-binding |
| 6355 // regulation of transcription, DNA-dependent // inferred from electronic annotation | 5634 // nucleus // inferred from electronic annotation /// 5667 // transcription factor complex // inferred from electronic annotation | 3677 // DNA binding // inferred from electronic annotation /// 3700 // transcription factor activity // inferred from electronic annotation | IPR001766 // Fork head transcription factor /// IPR009058 // Winged helix DNA-binding |
| 6915 // apoptosis // inferred from electronic annotation /// 6917 // induction of apoptosis // inferred from sequence or structural similarity | 5622 // intracellular // inferred from electronic annotation /// 5829 // cytosol // inferred from sequence or structural similarity | 16506 // apoptosis activator activity // inferred from sequence or structural similarity /// 16329 // CIDE-N; apoptosis regulator activity; 1.2e–50 // extended: inferred from sequence similarity | IPR003508 // Caspase-activated nuclease CIDE-N |
| 7049 // cell cycle // inferred from electronic annotation | 16021 // integral to membrane // traceable author statement | — | — |
| 6915 // apoptosis // inferred from electronic annotation /// 7049 // cell cycle // inferred from electronic annotation /// 7050 // cell cycle arrest // inferred from electronic annotation | 5856 // cytoskeleton // inferred from electronic annotation | — | IPR001715 // Calponin-like actin-binding /// IPR003108 // Growth-arrest-specific protein 2 |
| 5975 // carbohydrate metabolism // inferred from sequence or structural similarity /// 5977 // glycogen metabolism // inferred from sequence or structural similarity /// 5978 // glycogen biosynthesis // inferred from sequence or structural similarity /// 6091 // energy pathways // inferred from sequence or structural similarity | — | 3844 // 1,4-alpha-glucan branching enzyme activity // inferred from sequence or structural similarity /// 4553 // hydrolase activity, hydrolyzing O-glycosyl compounds // inferred from sequence or structural similarity /// 4556 // alpha-amylase activity // inferred from sequence or structural similarity /// 16740 // transferase activity // inferred from sequence or structural similarity /// 16757 // transferase activity, transferring glycosyl groups // inferred from sequence or structural similarity | IPR004193 // Glycoside hydrolase, family 13, N-terminal /// IPR006047 // Alpha amylase, catalytic domain |
| — | 5615 // extracellular space // traceable author statement | 5125 // cytokine activity // inferred from electronic annotation /// 8083 // growth factor activity // inferred from electronic annotation | IPR001839 // Transforming growth factor beta |
| — | — | — | Gene_Trap_Resource_2-04-02_IMAGE_and_RIKEN_cDNAs |
| — | 16021 // integral to membrane // traceable author statement | 3676 // nucleic acid binding // inferred from sequence or structural similarity /// 8488 // gamma-glutamyl carboxylase activity | IPR002014 // VHS /// IPR008153 // Gamma-adaptin, C-terminal /// IPR008152 // Alpha/gamma adaptin, C-terminal /// IPR004152 // GAT domain /// IPR008942 // ENTH/VHS /// IPR007782 // Vitamin K-dependent gamma-carboxylase /// IPR000504 // RNA-binding region RNP-1 (RNA |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | |
|---|---|---|
| | inferred from sequence or structural similarity /// 16874 // ligase activity // inferred from sequence or structural similarity /// 4478 // 2.5.1.6; methionine adenosyltransferase activity; 8.96e−180 // extended: Unknown /// 4478 // S-AdoMet_synt; methionine adenosyltransferase activity; 9.1e−66 // extended: Unknown | recognition motif) /// IPR001870 // B302, (SPRY)-like |
| 6631 // fatty acid metabolism // inferred from mutant phenotype /// 8152 // metabolism // inferred from electronic annotation /// 8654 // phospholipid biosynthesis // inferred from electronic annotation /// 40018 // positive regulation of body size // inferred from mutant phenotype | 5739 // mitochondrion // inferred from direct assay /// 16021 // integral to membrane // inferred from electronic annotation | 4366 // glycerol-3-phosphate O-acyltransferase activity // inferred from direct assay /// 8415 // acyltransferase activity // inferred from electronic annotation /// 16740 // transferase activity // inferred from electronic annotation | IPR002123 // Phospholipid/glycerol acyltransferase |
| 6631 // fatty acid metabolism // inferred from mutant phenotype /// 8152 // metabolism // inferred from electronic annotation /// 8654 // phospholipid biosynthesis // inferred from electronic annotation /// 40018 // positive regulation of body size // inferred from mutant phenotype | 5739 // mitochondrion // inferred from direct assay /// 16021 // integral to membrane // inferred from electronic annotation | 4366 // glycerol-3-phosphate O-acyltransferase activity // inferred from direct assay /// 8415 // acyltransferase activity // inferred from electronic annotation /// 16740 // transferase activity // inferred from electronic annotation | IPR002123 // Phospholipid/glycerol acyltransferase |
| 5975 // carbohydrate metabolism /// 6072 // glycerol-3-phosphate metabolism // inferred from mutant phenotype /// 6094 // gluconeogenesis // inferred from mutant phenotype | 9331 // glycerol-3-phosphate dehydrogenase complex // Unknown | 4367 // glycerol-3-phosphate dehydrogenase (NAD+) activity // inferred from electronic annotation /// 16491 // oxidoreductase activity // inferred from electronic annotation /// 16614 // oxidoreductase activity, acting on CH—OH group of donors // inferred from electronic annotation | IPR006109 // NAD-dependent glycerol-3-phosphate dehydrogenase domain /// IPR006168 // NAD-dependent glycerol-3-phosphate dehydrogenase /// IPR008927 // 6-phosphogluconate dehydrogenase, C-terminal-like |
| — | — | 3676 // nucleic acid binding // inferred from sequence or structural similarity | IPR000504 // RNA-binding region RNP-1 (RNA recognition motif) |
| — | — | 4364 // glutathione transferase activity // inferred from electronic annotation /// 16740 // transferase activity // inferred from electronic annotation | IPR004046 // Glutathione S-transferase, C-terminal /// IPR004045 // Glutathione S-transferase, N-terminal /// IPR003080 // Glutathione S-transferase, alpha class |
| — | — | 4364 // glutathione transferase activity // inferred from electronic annotation /// 16740 // transferase activity // inferred from electronic annotation | IPR004046 // Glutathione S-transferase, C-terminal /// IPR004045 // Glutathione S-transferase, N-terminal /// IPR003080 // Glutathione S-transferase, alpha class |
| 8152 // metabolism // inferred from electronic annotation | — | 4364 // glutathione transferase activity // inferred from electronic annotation /// 16740 // transferase activity // inferred from electronic annotation | IPR004046 // Glutathione S-transferase, C-terminal /// IPR004045 // Glutathione S-transferase, N-terminal /// IPR003081 // Glutathione S-transferase, Mu class |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| Column 1 | Column 2 | Column 3 | Column 4 |
|---|---|---|---|
| 8152 // metabolism // inferred from electronic annotation | — | 4364 // glutathione transferase activity // inferred from electronic annotation /// 16740 // transferase activity // inferred from electronic annotation | IPR004046 // Glutathione S-transferase, C-terminal /// IPR004045 // Glutathione S-transferase, N-terminal /// IPR003081 // Glutathione S-transferase, Mu class |
| 5978 // glycogen biosynthesis // inferred from sequence or structural similarity | — | 3824 // catalytic activity // inferred from sequence or structural similarity /// 4373 // glycogen (starch) synthase activity // inferred from sequence or structural similarity /// 16740 // transferase activity // inferred from sequence or structural similarity /// 16757 // transferase activity, transferring glycosyl groups // inferred from sequence or structural similarity | IPR008631 // Glycogen synthase |
| 6334 // nucleosome assembly // inferred from sequence or structural similarity /// 7001 // chromosome organization and biogenesis (sensu Eukarya) // inferred from sequence or structural similarity 8152 // metabolism // inferred from electronic annotation | 786 // nucleosome // inferred from sequence or structural similarity /// 5634 // nucleus // inferred from direct assay /// 5694 // chromosome // inferred from sequence or structural similarity | 3677 // DNA binding // inferred from sequence or structural similarity | — |
| 6118 // electron transport // inferred from electronic annotation /// 6605 // protein targeting // inferred from sequence or structural similarity | 5777 // peroxisome // inferred from electronic annotation | 16491 // oxidoreductase activity // inferred from electronic annotation | IPR002198 // Short-chain dehydrogenase/reductase SDR /// IPR002347 // Glucose/ribitol dehydrogenase |
| — | — | 16491 // oxidoreductase activity // inferred from electronic annotation /// 3973 // 1.1.3.15; (S)-2-hydroxy-acid oxidase activity; 4.5e-95 // extended: Unknown | IPR000262 // FMN-dependent alpha-hydroxy acid dehydrogenase /// IPR008259 // FMN-dependent alpha-hydroxy acid dehydrogenase, active site /// IPR003009 // FMN/related compound-binding core |
| 1505 // regulation of neurotransmitter levels // traceable author statement | — | 8168 // methyltransferase activity // inferred from sequence or structural similarity /// 8170 // N-methyltransferase activity // inferred from direct assay /// 16740 // transferase activity // inferred from sequence or structural similarity /// 46539 // 2.1.1.8; histamine N-methyltransferase activity; 3.8e-134 // extended: Unknown | — |
| 6355 // regulation of transcription, DNA-dependent // inferred from sequence or structural similarity /// 6397 // mRNA processing // inferred from sequence or structural similarity | 5634 // nucleus // inferred from direct assay /// 19013 // viral nucleocapsid // inferred from electronic annotation /// 30529 // ribonucleoprotein complex // inferred from electronic annotation | 3676 // nucleic acid binding // inferred from sequence or structural similarity /// 3677 // DNA binding // inferred from sequence or structural similarity /// 3723 // RNA binding // inferred from sequence or structural similarity | IPR000504 // RNA-binding region RNP-1 (RNA recognition motif) /// IPR006535 // HnRNP R and Q splicing factor |
| 6693 // prostaglandin metabolism // inferred from sequence or structural similarity /// 8152 // metabolism // inferred from sequence or structural similarity | — | 3824 // catalytic activity // inferred from sequence or structural similarity /// 4667 // prostaglandin-D synthase activity // inferred from sequence or structural similarity /// 5489 // electron transporter activity // inferred from sequence or structural similarity /// 16404 // 15- | IPR002198 // Short-chain dehydrogenase/reductase SDR /// IPR002347 // Glucose/ribitol dehydrogenase |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| 6605 // protein targeting // inferred from sequence or structural similarity /// 6631 // fatty acid metabolism // inferred from electronic annotation /// 8152 // metabolism // inferred from electronic annotation | 5777 // peroxisome // inferred from electronic annotation | hydroxyprostaglandin dehydrogenase (NAD+) activity // inferred from sequence or structural similarity /// 16491 // oxidoreductase activity // inferred from electronic annotation /// 3824 // catalytic activity // inferred from electronic annotation /// 4303 // estradiol 17-beta-dehydrogenase activity // inferred from electronic annotation /// 5498 // sterol carrier activity // inferred from electronic annotation /// 16491 // oxidoreductase activity // inferred from electronic annotation /// 16829 // lyase activity // inferred from electronic annotation /// 16853 // isomerase activity // inferred from electronic annotation | Steroid_Biosynthesis | IPR002198 // Short-chain dehydrogenase/reductase SDR /// IPR002539 // MaoC-like dehydratase /// IPR003033 // Sterol-binding /// IPR002347 // Glucose/ribitol dehydrogenase |
| 9408 // response to heat // inferred from electronic annotation | — | 3773 // heat shock protein activity // inferred from electronic annotation /// 5524 // ATP binding // inferred from electronic annotation | — | IPR001023 // Heat shock protein Hsp70 |
| 9408 // response to heat // inferred from electronic annotation | 5634 // nucleus // inferred from direct assay /// 5737 // cytoplasm // inferred from direct assay | 3773 // heat shock protein activity // inferred from electronic annotation | — | IPR002068 // Heat shock protein Hsp20 /// IPR001436 // Alpha crystallin /// IPR008978 // HSP20-like chaperone |
| 9408 // response to heat // inferred from electronic annotation | 5634 // nucleus // inferred from direct assay /// 5737 // cytoplasm // inferred from direct assay | 3773 // heat shock protein activity // inferred from electronic annotation | — | IPR002068 // Heat shock protein Hsp20 /// IPR001436 // Alpha crystallin /// IPR008978 // HSP20-like chaperone |
| 6457 // protein folding // inferred from electronic annotation /// 9408 // response to heat // inferred from electronic annotation | 5829 // cytosol // inferred from direct assay | 3754 // chaperone activity // inferred from electronic annotation /// 3773 // heat shock protein activity // inferred from electronic annotation /// 5515 // protein binding // inferred from physical interaction /// 5524 // ATP binding // inferred from electronic annotation /// 42803 // protein homodimerization activity // inferred from physical interaction | — | IPR001404 // Heat shock protein Hsp90 /// IPR003594 // ATP-binding region, ATPase-like /// IPR009079 // Four-helical cytokine |
| 6457 // protein folding // inferred from electronic annotation /// 9408 // response to heat // inferred from electronic annotation | 5829 // cytosol // inferred from direct assay | 3754 // chaperone activity // inferred from electronic annotation /// 3773 // heat shock protein activity // inferred from electronic annotation /// 5515 // protein binding // inferred from physical interaction /// 5524 // ATP binding // inferred from electronic annotation /// 42803 // protein homodimerization activity // inferred from physical interaction | — | IPR001404 // Heat shock protein Hsp90 /// IPR003594 // ATP-binding region, ATPase-like /// IPR009079 // Four-helical cytokine |
| 6508 // proteolysis and peptidolysis // inferred from electronic annotation | 5615 // extracellular space // traceable author statement | 4222 // metalloendopeptidase activity // inferred from electronic annotation /// 8237 // metallopeptidase activity // inferred from electronic annotation /// 16787 // hydrolase activity // inferred from electronic | Gene_Trap_Resource_2-04-02_Named_Genes | IPR001431 // Peptidase M16, insulinase-like /// IPR007863 // Peptidase M16, C-terminal |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| | | annotation /// 4231 // 3.4.24.56; insulysin activity; 3.94e−282 // extended: Unknown | IPR007743 // Interferon-inducible GTPase |
| 6955 // immune response // inferred from electronic annotation | — | — | IPR004020 // Pyrin domain /// IPR004021 // HIN-200/IF120x domain |
| 6955 // immune response // inferred from electronic annotation | — | — | IPR004020 // Pyrin domain /// IPR004021 // HIN-200/IF120x domain |
| 6955 // immune response // inferred from electronic annotation | — | — | IPR004020 // Pyrin domain /// IPR004021 // HIN-200/IF120x domain |
| 6955 // immune response // inferred from electronic annotation | — | — | IPR001440 // TPR repeat /// IPR008941 // TPR-like |
| 6468 // protein amino acid phosphorylation /// inferred from electronic annotation /// 6915 // apoptosis // inferred from electronic annotation | 5634 // nucleus // inferred from direct assay | 3714 // transcription corepressor activity // inferred from direct assay /// 4672 // protein kinase activity // inferred from electronic annotation /// 4674 // protein serine/threonine kinase activity // inferred from electronic annotation /// 5515 // protein binding // inferred from physical interaction /// 5524 // ATP binding // inferred from electronic annotation /// 16301 // kinase activity // inferred from electronic annotation | IPR000719 // Protein kinase /// IPR002290 // Serine/threonine protein kinase |
| 6020 // myo-inositol metabolism // traceable author statement | — | 287 // magnesium ion binding // inferred from electronic annotation /// 4437 // inositol/phosphatidylinositol phosphatase activity // inferred from electronic annotation /// 8934 // inositol-1(or 4)-monophosphatase activity // inferred from sequence or structural similarity /// 16787 // hydrolase activity // inferred from electronic annotation | Streptomycin biosynthesis /// Inositol phosphate metabolism /// Phosphatidylinositol signaling system | IPR000760 // Inositol monophosphatase /// IPR000146 // Inositol phosphatase/fructose-1,6-bisphosphatase |
| 6991 // response to sterol depletion // inferred from direct assay | — | 5515 // protein binding // inferred from physical interaction | — | IPR009904 // Insulin-induced |
| 6355 // regulation of transcription, DNA-dependent // inferred from electronic annotation | 5634 // nucleus // inferred from electronic annotation | 3677 // DNA binding // inferred from electronic annotation /// 3700 // transcription factor activity // inferred from electronic annotation | — | IPR001346 // Interferon regulatory factor /// IPR009058 // Winged helix DNA-binding /// IPR008984 // SMAD/FHA |
| — | — | 5515 // BTB; protein binding; 3.6e−29 // extended: inferred from electronic annotation | — | IPR000210 // BTB/POZ domain /// IPR006652 // Kelch repeat /// IPR006651 // Kelch motif |
| 74 // regulation of cell cycle // inferred from mutant phenotype /// 6355 // regulation of transcription, DNA-dependent // inferred from mutant phenotype /// 8151 // cell growth and/or maintenance // inferred from mutant phenotype /// 35026 // leading edge cell differentiation // inferred from mutant | 5622 // intracellular // inferred from electronic annotation /// 5634 // nucleus // inferred from direct assay /// 5667 // transcription factor complex // inferred from direct assay | 3677 // DNA binding // inferred from direct assay /// 3700 // transcription factor activity // inferred from electronic annotation /// 5515 // protein binding // inferred from physical interaction | Apoptosis /// MAPK_Cascade /// TGF_Beta_Signaling_Pathway /// Wnt_Signaling | IPR004827 // Basic-leucine zipper (bZIP) transcription factor /// IPR005643 // Jun-like transcription factor /// IPR002112 // Transcription factor Jun /// IPR008917 // Eukaryotic transcription factor, DNA-binding |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| phenotype /// 45944 // positive regulation of transcription from Pol II promoter // inferred from direct assay | | | |
| 6839 // mitochondrial transport // traceable author statement /// 7017 // microtubule-based process // traceable author statement /// 7028 // cytoplasm organization and biogenesis // inferred from mutant phenotype | 5871 // kinesin complex // traceable author statement /// 5875 // microtubule associated complex // inferred from electronic annotation | 3774 // motor activity // inferred from electronic annotation /// 3777 // microtubule motor activity // traceable author statement /// 5515 // protein binding // inferred from physical interaction /// 5524 // ATP binding // inferred from electronic annotation | IPR001752 // Kinesin, motor region |
| 6355 // regulation of transcription, DNA-dependent // inferred from electronic annotation | 5634 // nucleus // inferred from electronic annotation | 3677 // DNA binding // inferred from electronic annotation | IPR007087 // Zn-finger, C2H2 type |
| 6418 // tRNA aminoacylation for protein translation // inferred from sequence or structural similarity | 5764 // lysosome // inferred from direct assay /// 16020 // membrane // inferred from electronic annotation /// 16021 // integral to membrane // traceable author statement | 4812 // tRNA ligase activity // inferred from sequence or structural similarity /// 5524 // ATP binding // inferred from sequence or structural similarity | Gene_Trap_Resource_2-04-02_Named_Genes |
| — | 16021 // integral to membrane // traceable author statement | — | IPR002000 // Lysosome-associated membrane glycoprotein (Lamp)/CD68 /// IPR001412 // Aminoacyl-tRNA synthetase, class I |
| — | 16021 // integral to membrane // traceable author statement | — | IPR004687 // Golgi 4-transmembrane spanning transporter |
| — | — | — | IPR004687 // Golgi 4-transmembrane spanning transporter |
| — | — | — | IPR001452 // SH3 /// IPR001781 // Zn-binding protein, LIM /// IPR000900 // Nebulin |
| — | — | — | IPR001452 // SH3 /// IPR001781 // Zn-binding protein, LIM /// IPR000900 // Nebulin |
| — | — | — | IPR001452 // SH3 /// IPR001781 // Zn-binding protein, LIM /// IPR000900 // Nebulin |
| — | — | — | IPR001452 // SH3 /// IPR001781 // Zn-binding protein, LIM /// IPR000900 // Nebulin |
| 6810 // transport // inferred from electronic annotation | 5615 // extracellular space // traceable author statement | 5215 // transporter activity // inferred from electronic annotation /// 5488 // binding // inferred from sequence or structural similarity | IPR000566 // Lipocalin-related protein and Bos/Can/Equ allergen /// IPR002345 // Lipocalin /// IPR003087 // Neutrophil gelatinase-associated lipocalin |
| 7157 // heterophilic cell adhesion // inferred from electronic annotation /// 45445 // myoblast differentiation // inferred from direct assay | 5615 // extracellular space // inferred from direct assay | 5529 // sugar binding // inferred from electronic annotation | IPR001079 // Galectin, galactose-binding lectin /// IPR008985 // Concanavalin A-like lectin/glucanase |
| 7157 // heterophilic cell adhesion // inferred from electronic annotation /// 45445 // myoblast differentiation // inferred from direct assay | 5615 // extracellular space // inferred from direct assay | 5529 // sugar binding // inferred from electronic annotation | IPR001079 // Galectin, galactose-binding lectin /// IPR008985 // Concanavalin A-like lectin/glucanase |
| — | — | — | — |
| — | — | — | IPR004020 // Pyrin domain |
| — | — | — | IPR004882 // Protein of unknown function DUF259 |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| 6952 // defense response // inferred from electronic annotation | 5615 // extracellular space // traceable author statement /// 5886 // plasma membrane // inferred from electronic annotation /// 16020 // membrane // inferred from electronic annotation | — | IPR001526 // CD59 antigen |
| 6952 // defense response // inferred from electronic annotation | 5615 // extracellular space // traceable author statement /// 5886 // plasma membrane // inferred from electronic annotation /// 16020 // membrane // inferred from electronic annotation | — | IPR003632 // Cell-surface glycoprotein Ly-6/CD59 /// IPR001526 // CD59 antigen |
| 6952 // defense response // inferred from electronic annotation | 5615 // extracellular space // traceable author statement /// 5886 // plasma membrane // inferred from electronic annotation /// 16020 // membrane // inferred from electronic annotation | — | IPR003632 // Cell-surface glycoprotein Ly-6/CD59 /// IPR001526 // CD59 antigen |
| 6629 // lipid metabolism // inferred from electronic annotation /// 6631 // fatty acid metabolism // inferred from electronic annotation | — | 3824 // catalytic activity // inferred from sequence or structural similarity /// 4622 // lysophospholipase activity // inferred from electronic annotation /// 16787 // hydrolase activity // inferred from electronic annotation | IPR003140 // Phospholipase/Carboxylesterase /// IPR000379 // Esterase/lipase/thioesterase |
| 6468 // protein amino acid phosphorylation // inferred from electronic annotation /// 6915 // apoptosis // inferred from electronic annotation | — | 4672 // protein kinase activity // inferred from electronic annotation /// 4674 // protein serine/threonine kinase activity // inferred from electronic annotation /// 4713 // protein-tyrosine kinase activity // inferred from electronic annotation /// 5515 // protein binding // inferred from physical interaction /// 5524 // ATP binding // inferred from electronic annotation /// 16740 // transferase activity // inferred from electronic annotation | IPR000719 // Protein kinase /// IPR008271 // Serine/threonine protein kinase, active site /// IPR001179 // Peptidylprolyl isomerase, FKBP-type /// IPR002290 // Serine/threonine protein kinase |
| 6118 // electron transport; 6.7e−148 // extended: Unknown | — | 18685; 1.14.15.3; alkane 1-monooxygenase activity; 6.11e−139 // extended: Unknown | IPR001128 // Cytochrome P450 /// IPR002401 // E-class P450, group I |
| 6508 // proteolysis and peptidolysis // inferred from electronic annotation | 16020 // membrane // inferred from electronic annotation /// 16021 // integral to membrane // traceable author statement | 4245 // neprilysin activity // inferred from electronic annotation /// 8237 // metallopeptidase activity // inferred from electronic annotation /// 8270 // zinc ion binding // inferred from electronic annotation /// 16787 // hydrolase activity // inferred from electronic annotation | Gene_Trap_Resource_2-04-02_Named_Genes /// IPR000718 // Peptidase M13, neprilysin /// IPR008753 // Peptidase M13 /// IPR006025 // Peptidase M, neutral zinc metallopeptidases, zinc-binding site |
| 1558 // regulation of cell growth // inferred from sequence or structural similarity /// 7568 // aging // inferred from sequence or structural similarity | 5634 // nucleus // inferred from sequence or structural similarity | — | Gene_Trap_Resource_2-04-02_Named_Genes /// IPR008676 // MRG |
| 6139 // nucleobase, nucleoside, nucleotide and nucleic acid metabolism // inferred from sequence or structural similarity | — | 4645 // phosphorylase activity // inferred from electronic annotation /// 16740 // transferase activity // inferred from sequence or structural similarity /// 16757 // | IPR001369 // Purine (and other) phosphorylase, family 2 /// IPR010044 // Methylthioadenosine phosphorylase |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| 6470 // protein amino acid dephosphorylation // inferred from sequence or structural similarity | transferase activity, transferring glycosyl groups // inferred from sequence or structural similarity /// 17061 // 5'-methylthioadenosine phosphorylase activity // inferred from sequence or structural similarity | — | IPR010569 // Myotubularin-related /// IPR000387 // Tyrosine specific protein phosphatase and dual specificity protein phosphatase |
| | 4721 // phosphoprotein phosphatase activity // inferred from sequence or structural similarity /// 4722 // protein serine/threonine phosphatase activity // inferred from sequence or structural similarity /// 4725 // protein-tyrosine-phosphatase activity // inferred from sequence or structural similarity /// 4727 // prenylated protein tyrosine phosphatase activity // inferred from sequence or structural similarity /// 8138 // protein tyrosine/serine/threonine phosphatase activity // inferred from sequence or structural similarity /// 16787 // hydrolase activity // inferred from sequence or structural similarity | | |
| 6633 // fatty acid biosynthesis // inferred from electronic annotation | 36 // acyl carrier activity // inferred from electronic annotation /// 5509 // calcium ion binding // inferred from structural similarity /// 8137 // NADH dehydrogenase (ubiquinone) activity // inferred from sequence or structural similarity /// 16491 // oxidoreductase activity // inferred from sequence or structural similarity | 5615 // extracellular space // traceable author statement /// 5624 // membrane fraction // inferred from sequence or structural similarity /// 5739 // mitochondrion // inferred from sequence or structural similarity /// 5747 // respiratory chain complex I (sensu Eukarya) // inferred from sequence or structural similarity | IPR003231 // Acyl carrier protein (ACP) /// IPR006163 // Phosphopantetheine-binding domain /// IPR006162 // Phosphopantetheine attachment site /// IPR002048 // Calcium-binding EF-hand /// IPR009081 // Acyl carrier protein-like |
| 6355 // regulation of transcription, DNA-dependent // inferred from electronic annotation | 3677 // DNA binding // inferred from sequence or structural similarity /// 3700 // transcription factor activity // inferred from electronic annotation /// 3707 // steroid hormone receptor activity // inferred from electronic annotation /// 4872 // receptor activity // inferred from electronic annotation /// 4879 // ligand-dependent nuclear receptor activity // inferred from sequence or structural similarity | 5634 // nucleus // inferred from electronic annotation | IPR000536 // Ligand-binding domain of nuclear hormone receptor /// IPR001723 // Steroid hormone receptor /// IPR008946 // Steroid nuclear receptor, ligand-binding |
| 6355 // regulation of transcription, DNA-dependent // inferred from direct assay | 3677 // DNA binding // inferred from direct assay /// 3700 // transcription factor activity // inferred from direct assay /// 3707 // steroid hormone receptor activity // inferred from electronic annotation /// 4872 // receptor activity // inferred from electronic annotation /// 4879 // ligand-dependent | 5634 // nucleus // inferred from electronic annotation | Nuclear_Receptors | IPR001628 // Zn-finger, C4-type steroid receptor /// IPR000536 // Ligand-binding domain of nuclear hormone receptor /// IPR001723 // Steroid hormone receptor /// IPR001728 // Thyroid hormone receptor /// IPR008946 // Steroid |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | |
|---|---|---|
| | nuclear receptor activity // inferred from electronic annotation | nuclear receptor, ligand-binding /// IPR000324 // Vitamin D receptor /// IPR003079 // Nuclear receptor ROR |
| 6357 // regulation of transcription from Pol II promoter // inferred from sequence or structural similarity | 5667 // transcription factor complex // inferred from sequence or structural similarity | 3713 // transcription coactivator activity // inferred from sequence or structural similarity /// 4872 // receptor activity // inferred from electronic annotation /// 16922 // ligand-dependent nuclear receptor interactor activity // inferred from sequence or structural similarity | — |
| 9166 // nucleotide catabolism // inferred from electronic annotation | 5615 // extracellular space // traceable author statement /// 16021 // integral to membrane // traceable author statement | 16787 // hydrolase activity // inferred from electronic annotation /// 16788 // hydrolase activity, acting on ester bonds // inferred from electronic annotation /// 8253 // 3.1.3.5; 5'-nucleotidase activity; 1.18e-178 // extended: inferred from sequence similarity | IPR004843 // Metallo-phosphoesterase /// IPR008334 // 5'-Nucleotidase, C-terminal /// IPR006179 // 5'-Nucleotidase and apyrase /// IPR006146 // 5'-Nucleotidase, N-terminal |
| 6955 // immune response // inferred from electronic annotation | — | 3723 // RNA binding // inferred from electronic annotation /// 16740 // transferase activity // inferred from electronic annotation /// 16779 // nucleotidyltransferase activity // inferred from electronic annotation | IPR002934 // DNA polymerase, beta-like region /// IPR006117 // 2-5-oligoadenylate synthetase /// IPR006116 // 2-5 oligoadenylate synthetase ubiquitin-like domain /// IPR001201 // PAP/25A core domain /// IPR009008 // ValRS/IleRS editing |
| 6355 // regulation of transcription, DNA-dependent // inferred from sequence or structural similarity /// 42055 // neuronal lineage restriction // inferred from mutant phenotype | 5634 // nucleus // inferred from electronic annotation /// 5667 // transcription factor complex // inferred from sequence or structural similarity | 3677 // DNA binding // inferred from electronic annotation /// 3700 // transcription factor activity // inferred from sequence or structural similarity | IPR001092 // Basic helix-loop-helix dimerization domain bHLH |
| 7155 // cell adhesion // inferred from electronic annotation | 5578 // extracellular matrix // inferred from electronic annotation /// 5615 // extracellular space // traceable author statement | 5194 // cell adhesion molecule activity // inferred from electronic annotation /// 5201 // extracellular matrix structural constituent // inferred from electronic annotation | IPR001611 // Leucine-rich repeat /// IPR000372 // Cysteine-rich flanking region, N-terminal /// IPR003591 // Leucine-rich repeat, typical subtype |
| — | 5615 // extracellular space // traceable author statement /// 5887 // integral to plasma membrane // inferred from electronic annotation | 4872 // receptor activity // inferred from electronic annotation /// 4985 // opioid receptor activity // traceable author statement /// 247 // ERG2_Signal1R; C-8 sterol isomerase activity; 3.7e-133 // extended: inferred from electronic annotation | IPR006716 // ERG2 and sigmal receptor-like protein |
| 6810 // transport // inferred from electronic annotation /// 6953 // acute-phase response // inferred from electronic annotation | 5615 // extracellular space // traceable author statement | 5215 // transporter activity // inferred from electronic annotation | IPR000566 // Lipocalin-related protein and Bos/Can/Equ allergen /// IPR001500 // Alpha-1-acid glycoprotein |
| 6810 // transport // inferred from electronic annotation /// 6869 // lipid transport // inferred from electronic annotation /// 8202 // steroid metabolism // inferred from electronic annotation | — | — | IPR001849 // Pleckstrin-like /// IPR000648 // Oxysterol-binding protein |
| — | — | 3754 // chaperone activity // inferred from electronic annotation /// 3773 // heat shock | IPR001023 // Heat shock protein Hsp70 |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| — | protein activity // inferred from electronic annotation /// 5524 // ATP binding // inferred from electronic annotation /// 3754 // chaperone activity /// 3773 // heat shock protein activity // inferred from electronic annotation /// 5524 // ATP binding // inferred from electronic annotation | — | IPR001023 // Heat shock protein Hsp70 |
| 6164 // purine nucleotide biosynthesis // inferred from electronic annotation /// 6189 // 'de novo' IMP biosynthesis // inferred from electronic annotation | 9320 // phosphoribosylaminoimidazole carboxylase complex // inferred from electronic annotation | 3824 // catalytic activity // inferred from electronic annotation /// 4638 // phosphoribosylaminoimidazole carboxylase activity // inferred from electronic annotation /// 4639 // phosphoribosylaminoimidazole-succinocarboxamide synthase activity // inferred from electronic annotation /// 16829 // lyase activity // inferred from electronic annotation /// 16831 // carboxy-lyase activity // inferred from electronic annotation /// 16874 // ligase activity // inferred from electronic annotation | IPR000031 // 1-(5-Phosphoribosyl)-5-amino-4-imidazole-carboxylate (AIR) carboxylase /// IPR001636 // SAICAR synthetase |
| 6355 // regulation of transcription, DNA-dependent // inferred from electronic annotation | 5634 // nucleus // inferred from electronic annotation /// 5667 // transcription factor complex // inferred from electronic annotation | 3677 // DNA binding // inferred from electronic annotation /// 3700 // transcription factor activity // inferred from electronic annotation | IPR001356 // Homeobox /// IPR005542 // PBX domain /// IPR009057 // Homeodomain-like /// IPR000685 // Ribulose bisphosphate carboxylase, large chain |
| 6098 // pentose-phosphate shunt // inferred from sequence or structural similarity /// 9051 // pentose-phosphate shunt, oxidative branch // inferred from sequence or structural similarity | — | 4616 // phosphogluconate dehydrogenase (decarboxylating) activity // inferred from sequence or structural similarity /// 5489 // electron transporter activity // inferred from sequence or structural similarity /// 8114 // phosphogluconate 2-dehydrogenase activity // inferred from electronic annotation /// 16491 // oxidoreductase activity // inferred from sequence or structural similarity | Pentose phosphate pathway /// Pentose_Phosphate_Pathway | IPR006114 // 6-phosphogluconate dehydrogenase, C-terminal /// IPR006115 // 6-phosphogluconate dehydrogenase, NAD binding domain /// IPR006183 // 6-phosphogluconate dehydrogenase /// IPR006184 // 6-phosphogluconate-binding site /// IPR008927 // 6-phosphogluconate dehydrogenase, C-terminal-like /// IPR006113 // 6-phosphogluconate dehydrogenase, decarboxylating |
| 6098 // pentose-phosphate shunt // inferred from sequence or structural similarity /// 9051 // pentose-phosphate shunt, oxidative branch // inferred from sequence or structural similarity | — | 4616 // phosphogluconate dehydrogenase (decarboxylating) activity // inferred from sequence or structural similarity /// 5489 // electron transporter activity // inferred from sequence or structural similarity /// 8114 // phosphogluconate 2-dehydrogenase activity // inferred from electronic annotation /// 16491 // oxidoreductase activity // inferred from sequence or structural similarity | Pentose phosphate pathway /// Pentose_Phosphate_Pathway | IPR006114 // 6-phosphogluconate dehydrogenase, C-terminal /// IPR006115 // 6-phosphogluconate dehydrogenase, NAD binding domain /// IPR006183 // 6-phosphogluconate dehydrogenase /// IPR006184 // 6-phosphogluconate-binding site /// IPR008927 // 6-phosphogluconate dehydrogenase, C-terminal-like /// IPR006113 // 6-phosphogluconate dehydrogenase, decarboxylating |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| 6098 // pentose-phosphate shunt // inferred from sequence or structural similarity /// 9051 // pentose-phosphate shunt, oxidative branch // inferred from sequence or structural similarity | — | 4616 // phosphogluconate dehydrogenase (decarboxylating) activity // inferred from sequence or structural similarity /// 5489 // electron transporter activity // inferred from sequence or structural similarity /// 8114 // phosphogluconate 2-dehydrogenase activity // inferred from electronic annotation /// 16491 // oxidoreductase activity // inferred from sequence or structural similarity | Pentose phosphate pathway /// Pentose_Phosphate_Pathway | IPR006114 // 6-phosphogluconate dehydrogenase, C-terminal /// IPR006115 // 6-phosphogluconate dehydrogenase, NAD binding domain /// IPR006183 // 6-phosphogluconate dehydrogenase /// IPR006184 // 6-phosphogluconate-binding site /// IPR008927 // 6-phosphogluconate dehydrogenase, C-terminal-like /// IPR006113 // 6-phosphogluconate dehydrogenase, decarboxylating /// IPR001849 // Pleckstrin-like |
| 45210 // FasL biosynthesis // inferred from direct assay | 16021 // integral to membrane // inferred from electronic annotation | 5509 // calcium ion binding // inferred from electronic annotation | — | IPR005552 // Scramblase |
| — | 5615 // extracellular space // traceable author statement /// 16020 // membrane // inferred from sequence or structural similarity | 5044 // scavenger receptor activity // traceable author statement /// 5515 // protein binding // inferred from physical interaction | — | IPR001190 // Speract/scavenger receptor /// IPR000210 // BTB/POZ domain |
| 910 // cytokinesis // inferred from sequence or structural similarity /// 5977 // glycogen metabolism // inferred from sequence or structural similarity | 8287 // protein serine/threonine phosphatase complex // inferred from electronic annotation | 158 // protein phosphatase type 2A activity // inferred from sequence or structural similarity /// 163 // protein phosphatase type 1 activity // inferred from sequence or structural similarity /// 5515 // protein binding // inferred from physical interaction /// 4722 // protein serine/threonine phosphatase activity // inferred from electronic annotation /// 8420 // CTD phosphatase activity // inferred from sequence or structural similarity /// 15071 // protein phosphatase type 2C activity // inferred from sequence or structural similarity /// 16787 // hydrolase activity // inferred from sequence or structural similarity /// 17018 // myosin phosphatase activity // inferred from sequence or structural similarity /// 30145 // manganese ion binding // inferred from electronic annotation | G13_Signaling_Pathway | IPR006186 // Serine/threonine-specific protein phosphatase and bis(5-nucleosyl)-tetraphosphatase /// IPR004843 // Metallo-phosphoesterase |
| 6139 // nucleobase, nucleoside, nucleotide and nucleic acid metabolism // traceable author statement /// 6878 // copper ion homeostasis // traceable author statement /// 6979 // response to oxidative stress // inferred from direct assay | 5783 // endoplasmic reticulum // inferred from direct assay /// 5794 // Golgi apparatus // inferred from direct assay /// 5886 // plasma membrane // inferred from direct assay /// 45121 // lipid raft // inferred from direct assay | 5507 // copper ion binding // inferred from direct assay | — | IPR000817 // Prion protein |
| 6139 // nucleobase, nucleoside, nucleotide and nucleic acid metabolism // traceable author statement /// 6878 // copper ion homeostasis // traceable author statement /// 6979 // response to oxidative stress // inferred from direct assay | 5783 // endoplasmic reticulum // inferred from direct assay /// 5794 // Golgi apparatus // inferred from direct assay /// 5886 // plasma membrane // inferred from direct assay /// 45121 // lipid raft // inferred from direct assay | 5507 // copper ion binding // inferred from direct assay | — | IPR000817 // Prion protein |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| 30163 // protein catabolism // inferred from electronic annotation | 5634 // nucleus // inferred from electronic annotation /// 5737 // cytoplasm // inferred from electronic annotation /// 5829 // cytosol // inferred from electronic annotation | 166 // nucleotide binding // inferred from electronic annotation /// 5524 // ATP binding // inferred from electronic annotation /// 16787 // hydrolase activity // inferred from electronic annotation | IPR003959 // AAA ATPase, central region |
| 6470 // protein amino acid dephosphorylation // inferred from sequence or structural similarity | — | 4721 // phosphoprotein phosphatase activity // inferred from sequence or structural similarity /// 4725 // protein-tyrosine-phosphatase activity // inferred from electronic annotation /// 8138 // protein tyrosine/serine/threonine phosphatase activity // inferred from sequence or structural similarity | IPR000242 // Tyrosine specific protein phosphatase /// IPR000387 // Tyrosine specific protein phosphatase and dual specificity protein phosphatase |
| 7155 // cell adhesion // inferred from direct assay /// 16337 // cell-cell adhesion // inferred from direct assay | 5615 // extracellular space // traceable author statement /// 5911 // intercellular junction // inferred from direct assay /// 5913 // cell-cell adherens junction // inferred from direct assay /// 16021 // integral to membrane // traceable author statement | 5194 // cell adhesion molecule activity // inferred from direct assay /// 5515 // protein binding // inferred from physical interaction | IPR007110 // Immunoglobulin-like /// IPR003599 // Immunoglobulin subtype |
| 1570 // vasculogenesis // inferred from mutant phenotype /// 7626 // locomotory behavior // inferred from electronic annotation /// 8366 // nerve ensheathment // inferred from mutant phenotype | 5634 // nucleus // traceable author statement /// 5737 // cytoplasm // traceable author statement | 3676 // nucleic acid binding // inferred from sequence or structural similarity /// 3723 // RNA binding // traceable author statement | IPR004087 // KH |
| — | 16020 // membrane // inferred from electronic annotation | — | — |
| 74 // regulation of cell cycle // inferred from electronic annotation /// 6259 // DNA metabolism // inferred from sequence or structural similarity /// 6405 // RNA-nucleus export // inferred from sequence or structural similarity /// 6606 // protein-nucleus import // inferred from direct assay /// 6611 // protein-nucleus export // inferred from sequence or structural similarity /// 6886 // intracellular protein transport // inferred from sequence or structural similarity /// 7052 // mitotic spindle assembly // inferred from sequence or structural similarity /// 7067 // mitosis // inferred from sequence or structural similarity /// 7165 // signal transduction // inferred from sequence or structural similarity /// 7264 // small GTPase mediated signal transduction // inferred from sequence or structural similarity /// 8151 // cell growth and/or maintenance // inferred from electronic annotation /// 15031 | 785 // chromatin // inferred from sequence or structural similarity /// 5622 // intracellular // inferred from electronic annotation /// 5634 // nucleus // inferred from sequence or structural similarity /// 5643 // nuclear pore // inferred from sequence or structural similarity | 3925 // small monomeric GTPase activity // inferred from sequence or structural similarity /// 3929 // RAN small monomeric GTPase activity // inferred from sequence or structural similarity /// 4872 // receptor activity // inferred from electronic annotation /// 5515 // protein binding // inferred from physical interaction /// 5525 // GTP binding // inferred from sequence or structural similarity /// 8565 // protein transporter activity // inferred from sequence or structural similarity | IPR001806 // Ras GTPase superfamily /// IPR002041 // GTP-binding nuclear protein Ran // IPR005225 // Small GTP-binding protein domain /// IPR003577 // Ras small GTPase, Ras type // IPR003578 // Ras small GTPase, Rho type // IPR003579 // Ras small GTPase, Rab type |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| // protein transport // inferred from sequence or structural similarity /// 6260 // DNA replication // inferred from sequence or structural similarity /// 6396 // RNA processing // inferred from sequence or structural similarity /// 6445 // regulation of translation // inferred from sequence or structural similarity | | | IPR000504 // RNA-binding region RNP-1 (RNA recognition motif) /// IPR002343 // Paraneoplastic encephalomyelitis antigen |
| | 5634 // nucleus // inferred from sequence or structural similarity | 3676 // nucleic acid binding // inferred from sequence or structural similarity /// 3677 // DNA binding // inferred from sequence or structural similarity /// 3690 // double-stranded DNA binding // inferred from sequence or structural similarity /// 3697 // single-stranded DNA binding // inferred from sequence or structural similarity /// 3723 // RNA binding // inferred from sequence or structural similarity | |
| | — | 3676 // nucleic acid binding // inferred from electronic annotation /// 3723 // RNA binding // inferred from electronic annotation | Gene_Trap_Resource_2-04-02_Named_Genes |
| 30033 // microvillus biogenesis // inferred from mutant phenotype /// 45176 // apical protein localization // inferred from mutant phenotype | 5856 // cytoskeleton // inferred from electronic annotation /// 5902 // microvillus // inferred from direct assay | 3779 // actin binding // inferred from electronic annotation /// 5198 // structural molecule activity // inferred from electronic annotation /// 5515 // protein binding // inferred from physical interaction | IPR000299 // Band 4.1 /// IPR000798 // Ezrin/radixin/moesin ERM /// IPR009065 // FERM /// IPR008954 // Moesin |
| 6355 // regulation of transcription, DNA-dependent // inferred from sequence or structural similarity | — | 3677 // DNA binding // inferred from sequence or structural similarity | IPR003150 // DNA-binding RFX |
| 7165 // signal transduction // inferred from electronic annotation /// 7186 // G-protein coupled receptor protein signaling pathway // traceable author statement | — | 4871 // signal transducer activity // inferred from electronic annotation /// 5096 // GTPase activator activity // traceable author statement | IPR000342 // Regulator of G protein |
| 7165 // signal transduction // inferred from electronic annotation /// 7186 // G-protein coupled receptor protein signaling pathway // traceable author statement | — | 4871 // signal transducer activity // inferred from electronic annotation /// 5096 // GTPase activator activity // traceable author statement | IPR000342 // Regulator of G protein |
| 7399 // neurogenesis // inferred from direct assay | 5783 // endoplasmic reticulum // inferred from direct assay /// 16021 // integral to membrane // inferred from electronic annotation | — | IPR003388 // Reticulon |
| 7399 // neurogenesis // inferred from direct assay | 5783 // endoplasmic reticulum // inferred from direct assay /// 16021 // integral to membrane // inferred from electronic annotation | — | IPR003388 // Reticulon |
| — | — | 5125 // cytokine activity // inferred from electronic annotation /// 5509 // calcium ion binding // inferred from electronic annotation | IPR002048 // Calcium-binding EF-hand /// IPR001751 // Calcium-binding protein, S-100/ICaBP type |
| 6953 // acute-phase response // inferred from electronic annotation | 5576 // extracellular // inferred from electronic annotation | 5319 // lipid transporter activity // inferred from electronic annotation /// 5515 // protein binding // inferred from physical interaction /// 3794 // SAA_proteins; acute-phase response protein activity; 6.5e-78 // extended: Unknown | — |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| 6953 // acute-phase response // inferred from electronic annotation | 5576 // extracellular // inferred from electronic annotation | 5319 // lipid transporter activity // inferred from electronic annotation /// 5515 // protein binding // inferred from physical interaction /// 3794 // SAA_proteins; acute-phase response protein activity; 1.3e−72 // extended: Unknown | IPR000096 // Serum amyloid A protein |
| 6953 // acute-phase response // inferred from electronic annotation | 5576 // extracellular // inferred from electronic annotation | 5319 // lipid transporter activity // inferred from electronic annotation /// 5515 // protein binding // inferred from physical interaction /// 3794 // SAA_proteins; acute-phase response protein activity; 1.3e−72 // extended: Unknown | IPR000096 // Serum amyloid A protein |
| 6953 // acute-phase response // inferred from electronic annotation | 5576 // extracellular // inferred from electronic annotation /// 5615 // extracellular space // traceable author statement | 5319 // lipid transporter activity // inferred from electronic annotation /// 3794 // SAA_proteins; acute-phase response protein activity; 1.9e−82 // extended: Unknown | IPR000096 // Serum amyloid A protein |
| 8152 // metabolism // inferred from electronic annotation /// 16126 // sterol biosynthesis // inferred from electronic annotation | 5783 // endoplasmic reticulum // inferred from electronic annotation /// 16021 // integral to membrane // traceable author statement | 3824 // catalytic activity // inferred from electronic annotation /// 16491 // oxidoreductase activity // inferred from electronic annotation | IPR006088 // Sterol desaturase /// IPR006087 // SUR2-type hydroxylase/desaturase, catalytic domain |
| 6887 // exocytosis // inferred from mutant phenotype | 8021 // synaptic vesicle // traceable author statement /// 16021 // integral to membrane // traceable author statement /// synaptic vesicle membrane // inferred from direct assay /// 42589 // zymogen granule membrane // inferred from direct assay | — | IPR007273 // SCAMP |
| — | 5615 // extracellular space // traceable author statement /// 16020 // membrane // inferred from electronic annotation /// 16021 // integral to membrane // traceable author statement | Cholesterol_Biosynthesis | — |
| — | 5615 // extracellular space // traceable author statement /// 16020 // membrane // inferred from electronic annotation /// 16021 // integral to membrane // traceable author statement | 8092 // cytoskeletal protein binding // inferred from electronic annotation | IPR001050 // Syndecan /// IPR003585 // Neurexin/syndecan/glycophorin C |
| — | 5615 // extracellular space // traceable author statement /// 16021 // integral to membrane // traceable author statement | 8092 // cytoskeletal protein binding // inferred from electronic annotation | IPR001050 // Syndecan /// IPR003585 // Neurexin/syndecan/glycophorin C |
| — | — | — | IPR007110 // Immunoglobulin-like /// IPR009151 // Basigin /// IPR003598 // Immunoglobulin C-2 type /// IPR003599 // Immunoglobulin subtype |
| 6810 // transport // inferred from electronic annotation /// 6886 // intracellular protein transport // inferred from electronic annotation /// 6887 // exocytosis // inferred from electronic annotation /// 15031 // protein transport // inferred from electronic annotation | — | 8565 // protein transporter activity // inferred from electronic annotation | IPR007191 // Sec8 exocyst complex component specific domain |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | Gene_Trap_Resource_2-04-02_Named_Genes_2 | |
|---|---|---|---|
| 910 // cytokinesis // inferred from electronic annotation /// 7049 // cell cycle // inferred from electronic annotation /// 16288 // cytokinesis // inferred from electronic annotation | — | 5525 // GTP binding // inferred from electronic annotation | IPR000038 // Cell division/GTP binding protein /// IPR008115 // Septin 7 |
| 42176 // regulation of protein catabolism // inferred from physical interaction | — | 4866 // endopeptidase inhibitor activity /// inferred from electronic annotation /// 4867 // serine-type endopeptidase inhibitor activity // inferred from electronic annotation | IPR000215 // Serpin |
| 42176 // regulation of protein catabolism // inferred from physical interaction | — | 4866 // endopeptidase inhibitor activity /// inferred from electronic annotation /// 4867 // serine-type endopeptidase inhibitor activity // inferred from electronic annotation /// 8233 // peptidase activity // inferred from electronic annotation | IPR000215 // Serpin |
| | — | 4866 // endopeptidase inhibitor activity /// inferred from electronic annotation /// 4867 // serine-type endopeptidase inhibitor activity // inferred from electronic annotation /// 8233 // peptidase activity // inferred from electronic annotation | IPR000215 // Serpin |
| 6468 // protein amino acid phosphorylation // inferred from electronic annotation /// 6915 // apoptosis // inferred from electronic annotation | 5634 // nucleus // inferred from electronic annotation | 4672 // protein kinase activity // inferred from electronic annotation /// 4674 // protein serine/threonine kinase activity // inferred from electronic annotation /// 5524 // ATP binding // inferred from electronic annotation /// 16301 // kinase activity // inferred from electronic annotation /// 16740 // transferase activity // inferred from electronic annotation | IPR000719 // Protein kinase /// IPR000961 // Protein kinase C-terminal domain /// IPR008271 // Serine/threonine protein kinase, active site /// IPR002290 // Serine/threonine protein kinase |
| 6665 // sphingolipid metabolism // inferred from direct assay /// 6668 // sphinganine-1-phosphate metabolism // inferred from direct assay /// 6670 // sphingosine metabolism // inferred from direct assay /// 6915 // apoptosis // inferred from direct assay | 5624 // membrane fraction // inferred from direct assay /// 5739 // NOT mitochondrion // inferred from direct assay /// 5783 // endoplasmic reticulum // inferred from direct assay /// 5794 // NOT Golgi apparatus // inferred from direct assay /// 15629 // NOT actin cytoskeleton // inferred from direct assay /// 16021 // integral to membrane // traceable author statement | 16787 // hydrolase activity // inferred from electronic annotation /// 42392 // sphingosine-1-phosphate phosphatase activity // inferred from direct assay | IPR000326 // PA-phosphatase related phosphoesterase /// IPR008934 // Acid phosphatase/vanadium-dependent haloperoxidase |
| | — | — | IPR006993 // SH3-binding, glutamic acid-rich protein |
| | — | — | IPR006993 // SH3-binding, glutamic acid-rich protein |
| 6810 // transport // inferred from electronic annotation /// 6839 // mitochondrial transport // inferred from electronic annotation | 5739 // mitochondrion // inferred from direct assay /// 16020 // membrane // inferred | 5488 // binding // inferred from electronic annotation /// 15290 // electrochemical | IPR001993 // Mitochondrial substrate carrier /// IPR002030 // Mitochondrial |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| transport // inferred from sequence or structural similarity | from electronic annotation /// 16021 // integral to membrane // inferred from electronic annotation /// 19866 // inner membrane // inferred from electronic annotation | potential-driven transporter activity // inferred from direct assay | brown fat uncoupling protein /// IPR003382 // Flavoprotein |
| 6810 // transport // inferred from electronic annotation /// 6839 // mitochondrial transport // inferred from electronic annotation | 5739 // mitochondrion // inferred from electronic annotation /// 5743 // mitochondrial inner membrane // inferred from electronic annotation /// 16020 // membrane // inferred from electronic annotation /// 16021 // integral to membrane // inferred from electronic annotation /// 19866 // inner membrane // inferred from electronic annotation | 5215 // transporter activity // inferred from sequence or structural similarity /// 5488 // binding // inferred from electronic annotation | Electron_Transport_Chain | IPR001993 // Mitochondrial substrate carrier /// IPR002030 // Mitochondrial brown fat uncoupling protein /// IPR002067 // Mitochondrial carrier protein /// IPR002113 // Adenine nucleotide translocator 1 |
| 6810 // transport // inferred from electronic annotation /// 6811 // ion transport // inferred from electronic annotation /// 15711 // organic anion transport // inferred from direct assay | 5887 // integral to plasma membrane // inferred from sequence or structural similarity /// 16020 // membrane // inferred from electronic annotation /// 16021 // integral to membrane // inferred from electronic annotation | 5215 // transporter activity // inferred from electronic annotation /// 8514 // organic anion transporter activity // inferred from direct assay | — | IPR004157 // Organic anion transporter polypeptide (OATP), C-terminal /// IPR007114 // Major facilitator superfamily /// IPR004156 // Organic anion transporter polypeptide (OATP), N-terminal |
| 6886 // intracellular protein transport // inferred from sequence or structural similarity /// 6892 // post-Golgi transport // inferred from sequence or structural similarity /// 6903 // vesicle targeting // inferred from sequence or structural similarity /// 6944 // membrane fusion // inferred from sequence or structural similarity /// 7033 // vacuole organization and biogenesis // inferred from sequence or structural similarity /// 15031 // protein transport // inferred from sequence or structural similarity | 5886 // plasma membrane // inferred from sequence or structural similarity /// 16020 // membrane // inferred from sequence or structural similarity /// 19717 // synaptosome // inferred from electronic annotation /// 30133 // transport vesicle // inferred from sequence or structural similarity | 5486 // t-SNARE activity // inferred from sequence or structural similarity /// 8565 // protein transporter activity // inferred from sequence or structural similarity | — | IPR000928 // SNAP-25 /// IPR000727 // Target SNARE coiled-coil domain |
| 1558 // regulation of cell growth // inferred from electronic annotation /// 7165 // signal transduction // inferred from electronic annotation /// 7242 // intracellular signaling cascade // inferred from electronic annotation /// 40014 // regulation of body size // inferred from mutant phenotype /// 45666 // positive regulation of neuron differentiation // inferred from direct assay | — | — | Gene_Trap_Resource_2-04-02_Named_Genes | IPR000980 // SH2 motif /// IPR001496 // SOCS protein, C-terminal |
| — | 1725 // stress fibers // inferred from direct assay | 5515 // protein binding // inferred from direct assay /// 19901 // protein kinase binding // inferred from direct assay | — | IPR001452 // SH3 /// IPR003127 // Sorbin-like /// IPR000108 // Neutrophil cytosol factor 2 |
| 1503 // ossification // inferred from electronic annotation /// 7155 // cell adhesion // inferred from electronic annotation | 5615 // extracellular space // traceable author statement | 5125 // cytokine activity // inferred from electronic annotation /// 5194 // cell adhesion molecule activity // inferred from electronic annotation | TGF_Beta_Signaling_Pathway | IPR002038 // Osteopontin |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| 6520 // amino acid metabolism // inferred from electronic annotation | — | 16829 // lyase activity // inferred from electronic annotation /// 16853 // isomerase activity // inferred from electronic annotation | IPR001926 // Pyridoxal-5'-phosphate-dependent enzyme, beta subunit /// IPR000634 // Serine/threonine dehydratase, pyridoxal-phosphate-binding site |
| 6355 // regulation of transcription, DNA-dependent // inferred from electronic annotation /// 7165 // signal transduction // inferred from electronic annotation /// 7242 // intracellular signaling cascade // inferred from electronic annotation | 5634 // nucleus // inferred from direct assay /// 5737 // cytoplasm // inferred from direct assay | 3677 // DNA binding // inferred from electronic annotation /// 3700 // transcription factor activity // inferred from electronic annotation /// 4871 // signal transducer activity // inferred from electronic annotation | TGF_Beta_Signaling_Pathway IPR000980 // SH2 motif /// IPR001217 // STAT protein /// IPR008967 // p53-like transcription factor |
| 6457 // protein folding // inferred from electronic annotation | 5615 // extracellular space // traceable author statement | 3754 // chaperone activity // inferred from electronic annotation /// 5524 // ATP binding // inferred from electronic annotation | Gene_Trap_Resource_2-04-02_IMAGE_and_RIKEN_cDNAs IPR001023 // Heat shock protein Hsp70 |
| — | 5783 // endoplasmic reticulum // inferred from electronic annotation /// 16021 // integral to membrane // inferred from electronic annotation /// 19013 // viral nucleocapsid // inferred from electronic annotation /// 30529 // ribonucleoprotein complex // inferred from electronic annotation | — | IPR002995 // Surf4 protein |
| — | 5783 // endoplasmic reticulum // inferred from electronic annotation /// 16021 // integral to membrane // inferred from electronic annotation /// 19013 // viral nucleocapsid // inferred from electronic annotation /// 30529 // ribonucleoprotein complex // inferred from electronic annotation | — | IPR002995 // Surf4 protein |
| 7067 // mitosis // inferred from direct assay /// 7126 // meiosis // inferred from direct assay | 793 // condensed chromosome // inferred from direct assay /// 795 // synaptonemal complex // inferred from direct assay /// 5634 // nucleus // inferred from electronic annotation | 5515 // protein binding // inferred from physical interaction | IPR006888 // Cor1/Xlr/Xmr conserved region // IPR002742 // Desulfoferrodoxin, ferrous iron-binding region |
| 7067 // mitosis // inferred from direct assay /// 7126 // meiosis // inferred from direct assay | 793 // condensed chromosome // inferred from direct assay /// 795 // synaptonemal complex // inferred from direct assay /// 5634 // nucleus // inferred from electronic annotation | 5515 // protein binding // inferred from physical interaction | IPR006888 // Cor1/Xlr/Xmr conserved region /// IPR002742 // Desulfoferrodoxin, ferrous iron-binding region |
| — | — | — | IPR005334 // Tctex-1 family |
| 7596 // blood coagulation // inferred from electronic annotation | 5615 // extracellular space // traceable author statement | 4867 // serine-type endopeptidase inhibitor activity // inferred from electronic annotation | IPR005334 // Tctex-1 family IPR002223 // Pancreatic trypsin inhibitor (Kunitz) /// IPR008296 // Tissue factor pathway inhibitor |
| 6355 // regulation of transcription, DNA-dependent // inferred from sequence or structural similarity | 5634 // nucleus // inferred from sequence or structural similarity | 3700 // transcription factor activity // inferred from sequence or structural similarity | IPR000580 // TSC-22/Dip/Bun |
| — | 5794 // Golgi apparatus // inferred from | — | — |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| — | electronic annotation /// 16021 // integral to membrane // inferred from electronic annotation | 5525 // GTP binding // inferred from sequence or structural similarity | — | IPR007743 // Interferon-inducible GTPase |
| — | 5634 // nucleus // inferred from electronic annotation | — | — | IPR009786 // Thyroid hormone-inducible hepatic Spot 14 |
| 7338 // fertilization (sensu Animalia) // inferred from mutant phenotype /// 40008 // regulation of growth // inferred from mutant phenotype | — | 4802 // transketolase activity // inferred from direct assay /// 5509 // calcium ion binding // inferred from electronic annotation /// 16740 // transferase activity // inferred from electronic annotation | Pentose_Phosphate_Pathway | IPR005474 // Transketolase, N terminal /// IPR005475 // Transketolase, central region /// IPR005476 // Transketolase, C terminal /// IPR009014 // Transketolase, C-terminal-like |
| 45329 // carnitine biosynthesis // inferred from direct assay | 5739 // mitochondrion // inferred from direct assay | 16491 // oxidoreductase activity // inferred from electronic annotation /// 16702 // oxidoreductase activity, acting on single donors with incorporation of molecular oxygen, incorporation of two atoms of oxygen // inferred from direct assay | Lysine degradation | IPR004994 // Gamma-butyrobetaine hydroxylase |
| 6936 // muscle contraction // traceable author statement /// 7517 // muscle development // inferred from electronic annotation | 5856 // cytoskeleton // inferred from electronic annotation /// 5862 // muscle thin filament tropomyosin // traceable author statement | 3779 // actin binding // inferred from electronic annotation /// 5200 // structural constituent of cytoskeleton // inferred from electronic annotation | — | IPR000533 // Tropomyosin /// IPR002017 // Spectrin repeat |
| — | 5622 // intracellular // inferred from electronic annotation /// 5737 // cytoplasm // inferred from direct assay | 5515 // protein binding // inferred from physical interaction /// 8270 // zinc ion binding // inferred from electronic annotation | — | IPR001258 // NHL repeat /// IPR001841 // Zn-finger, RING /// IPR001298 // Filamin/ABP280 repeat /// IPR000315 // Zn-finger, B-box /// IPR003649 // B-box, C-terminal /// IPR008941 // TPR-like |
| 7017 // microtubule-based process // inferred from electronic annotation /// 7018 // microtubule-based movement // inferred from sequence or structural similarity | 5874 // microtubule // inferred from electronic annotation | 5198 // structural molecule activity // inferred from sequence or structural similarity /// 5200 // structural constituent of cytoskeleton // inferred from electronic annotation | — | IPR003008 // Tubulin/FtsZ, GTPase /// IPR000217 // Tubulin /// IPR002452 // Alpha tubulin /// IPR008280 // Tubulin/FtsZ, C-terminal |
| 7017 // microtubule-based process // inferred from electronic annotation | 5874 // microtubule // inferred from electronic annotation | 5200 // structural constituent of cytoskeleton // inferred from electronic annotation /// 5525 // GTP binding // inferred from electronic annotation | — | IPR008280 // Tubulin/FtsZ, C-terminal /// IPR002453 // Beta tubulin /// IPR003008 // Tubulin/FtsZ, GTPase /// IPR000217 // Tubulin /// IPR010916 // TONB Box N terminus |
| 6118 // electron transport // inferred from sequence or structural similarity | — | 5489 // electron transporter activity // inferred from sequence or structural similarity | Gene_Trap_Resource_2-04-02_Named_Genes_2 | IPR006662 // Thioredoxin type domain /// IPR006663 // Thioredoxin domain 2 /// IPR004480 // Glutaredoxin-related protein |
| 6512 // ubiquitin cycle // inferred from sequence or structural similarity | — | 4840 // ubiquitin conjugating enzyme activity // inferred from sequence or structural similarity /// 16874 // ligase activity // inferred from electronic annotation | — | IPR000608 // Ubiquitin-conjugating enzymes |
| 74 // regulation of cell cycle // inferred from mutant phenotype /// 278 // mitotic cell | — | 19781 // NEDD8 activating enzyme activity // traceable author statement /// 3824 // | — | IPR000594 // UBA/THIF-type NAD/FAD binding fold /// IPR000127 |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| cycle // inferred from mutant phenotype /// 7113 // endomitotic cell cycle // inferred from mutant phenotype | | ThiF; catalytic activity; 2.1e−57 // extended: Unknown | Ubiquitin-activating enzyme repeat /// IPR000205 // NAD-binding site /// IPR009036 // Molybdenum cofactor biosynthesis |
| 74 // regulation of cell cycle // inferred from mutant phenotype /// 278 // mitotic cell cycle // inferred from mutant phenotype /// 7113 // endomitotic cell cycle // inferred from mutant phenotype | — | 19781 // NEDD8 activating enzyme activity // traceable author statement /// 3824 // ThiF; catalytic activity; 2.1e−57 // extended: Unknown | IPR000594 // UBA/THIF-type NAD/FAD binding fold /// IPR000127 // Ubiquitin-activating enzyme repeat /// IPR000205 // NAD-binding site /// IPR009036 // Molybdenum cofactor biosynthesis |
| 6464 // protein modification // inferred from sequence or structural similarity /// 6512 // ubiquitin cycle // inferred from sequence or structural similarity | — | 3824 // catalytic activity // inferred from sequence or structural similarity /// 4839 // ubiquitin activating enzyme activity // inferred from sequence or structural similarity /// 8642 // ubiquitin-like activating enzyme activity // inferred from electronic annotation | IPR000127 // Ubiquitin-activating enzyme repeat /// IPR009036 // Molybdenum cofactor biosynthesis /// IPR000594 // UBA/THIF-type NAD/FAD binding fold /// IPR000345 // Cytochrome c heme-binding site /// IPR000205 // NAD-binding site |
| 6810 // transport // inferred from electronic annotation /// 6839 // mitochondrial transport // inferred from electronic annotation | 5739 // mitochondrion // inferred from sequence or structural similarity /// 16020 // membrane // inferred from electronic annotation /// 16021 // integral to membrane // inferred from electronic annotation /// 19866 // inner membrane // inferred from electronic annotation | 5488 // binding // inferred from electronic annotation | IPR001993 // Mitochondrial substrate carrier /// IPR002030 // Mitochondrial brown fat uncoupling protein /// IPR02113 // Adenine nucleotide translocator 1 |
| 6118 // electron transport // inferred from electronic annotation | — | — | Electron_Transport_Chain |
| 6511 // ubiquitin-dependent protein catabolism // inferred from electronic annotation | — | 3979 // UDP-glucose 6-dehydrogenase activity // inferred from electronic annotation /// 16491 // oxidoreductase activity // inferred from electronic annotation | IPR001732 // UDP-glucose/GDP-mannose dehydrogenase /// IPR008927 // 6-phosphogluconate dehydrogenase, C-terminal-like |
| | — | 4197 // cysteine-type endopeptidase activity // inferred from electronic annotation /// 4221 // ubiquitin thiolesterase activity // inferred from electronic annotation /// 8234 // cysteine-type peptidase activity // inferred from electronic annotation /// 16787 // hydrolase activity // inferred from electronic annotation | IPR001394 // Peptidase C19, ubiquitin carboxyl-terminal hydrolase family 2 |
| 6869 // lipid transport // inferred from electronic annotation /// 6897 // endocytosis // inferred from electronic annotation /// 8203 // cholesterol metabolism // inferred from electronic annotation | 5615 // extracellular space // traceable author statement /// 5905 // coated pit // inferred from electronic annotation /// 16020 // membrane // inferred from electronic annotation /// 16021 // integral to membrane // traceable author statement | 4872 // receptor activity // inferred from electronic annotation /// 5319 // lipid transporter activity // inferred from electronic annotation /// 5509 // calcium ion binding // inferred from electronic annotation | IPR006209 // EGF-like domain /// IPR002172 // Low density lipoprotein-receptor, class A /// IPR000033 // Low-density lipoprotein receptor, YWTD repeat /// IPR000152 // Aspartic acid and asparagine hydroxylation site /// IPR001881 // EGF-like calcium-binding /// IPR000742 // EGF-like domain, subtype 2 |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | |
|---|---|---|
| 6807 // nitrogen metabolism // inferred from electronic annotation | 5615 // extracellular space // traceable author statement | 16787 // hydrolase activity // inferred from electronic annotation /// 16810 // hydrolase activity, acting on carbon-nitrogen (but not peptide) bonds // inferred from electronic annotation | IPR003010 // Nitrilase/cyanide hydratase and apolipoprotein N-acyltransferase |
| 6807 // nitrogen metabolism // inferred from electronic annotation | 5615 // extracellular space // traceable author statement | 16787 // hydrolase activity // inferred from electronic annotation /// 16810 // hydrolase activity, acting on carbon-nitrogen (but not peptide) bonds // inferred from electronic annotation | IPR003010 // Nitrilase/cyanide hydratase and apolipoprotein N-acyltransferase |
| — | — | 3831 // beta-N-acetylglucosaminylglycopeptide beta-1,4-galactosyltransferase activity // inferred from direct assay | — |
| 6605 // protein targeting // inferred from direct assay | — | 4497 // monooxygenase activity // inferred from electronic annotation /// 16301 // kinase activity // inferred from electronic annotation /// 19904 // protein domain specific binding // inferred from direct assay | IPR001680 // G-protein beta WD-40 repeat /// IPR000306 // Zn-finger, FYVE type /// IPR000409 // Beige/BEACH domain IPR000308 // 14-3-3 protein |
| 6355 // regulation of transcription, DNA-dependent // inferred from sequence or structural similarity | 5634 // nucleus // inferred from direct assay | 3676 // nucleic acid binding // inferred from electronic annotation /// 3700 // transcription factor activity // inferred from sequence or structural similarity /// 8270 // zinc ion binding // inferred from sequence or structural similarity | IPR007087 // Zn-finger, C2H2 type |
| — | — | 5524 // HATPase_c; ATP binding; 6.7e–18 // extended: inferred from electronic annotation | — |
| — | — | — | — |
| — | — | — | — |
| 6605 // MAS20; protein targeting; 2.9e–05 // extended: inferred from electronic annotation | — | 19904 // 14-3-3; protein domain specific binding; 5e–149 // extended: Unknown 3824 // Om_Arg_deC_N; catalytic activity; 1e–129 // extended: Unknown /// 4586 // 4.1.1.17; ornithine decarboxylase activity; 3.45e–152 // extended: inferred from electronic annotation 5488 // mito_carr; binding; 3.9e–34 // extended: inferred from electronic annotation | — |
| — | — | — | — |
| — | — | — | — |
| — | — | — | — |
| — | — | — | — |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| 6118 // p450; electron transport; 8.2e-195 // extended: Unknown | — | — | — |
| — | — | — | — |
| 5975 // Glucosamine_iso; carbohydrate metabolism; 9.9e-164 // extended: Unknown | — | 3700 // TSC22; transcription factor activity; 5.9e-43 // extended: inferred from electronic annotation | — |
| — | — | 5489 // cytochrome_c; electron transporter activity; 4.1e-39 // extended: inferred from sequence similarity | — |
| — | — | — | — |
| — | — | 5524 // DEAD; ATP binding; 8.3e-31 // extended: inferred from electronic annotation | — |
| — | — | 3676 // rrm; nucleic acid binding; 4.8e-19 // extended: inferred from electronic annotation | — |
| — | — | — | — |
| — | — | — | — |
| 6355 // regulation of transcription, DNA-dependent // inferred from sequence or structural similarity | — | 3824 // 4HBT; catalytic activity; 7.8e-09 // extended: Unknown | — |
| | | 3677 // DNA binding // inferred from sequence or structural similarity /// 3700 // transcription factor activity // inferred from sequence or structural similarity | |
| — | 5615 // extracellular space // traceable author statement /// 16021 // integral to membrane // traceable author statement | — | — |
| — | — | 5529 // sugar binding // inferred from sequence or structural similarity | — |
| — | — | — | IPR007884 // DREV methyltransferase /// IPR006683 // Thioesterase superfamily |
| — | — | — | IPR002110 // Ankyrin /// IPR000086 // NUDIX hydrolase |
| — | — | — | IPR008151 // Phytoene dehydrogenase-related protein |
| — | — | — | — |
| — | — | — | IPR001079 // Galectin, galactose-binding lectin /// IPR008985 // Concanavalin A-like lectin/glucanase |
| — | — | — | IPR001683 // Phox-like |
| — | — | — | IPR005036 // Putative phosphatase regulatory subunit |
| 9116 // nucleoside metabolism // inferred from sequence or structural similarity | — | 3824 // catalytic activity // inferred from sequence or structural similarity /// 16740 // | IPR000845 // Purine and other phosphorylases, family 1 /// |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | |
|---|---|---|
| — | — | IPR010059 // Uridine phosphorylase, eukaryotic |
| — | transferase activity // inferred from electronic annotation /// 16757 // transferase activity, transferring glycosyl groups // inferred from electronic annotation /// 4850 // 2.4.2.3; uridine phosphorylase activity; 2.59e–118 // extended: inferred from electronic annotation | |
| — | — | IPR009311 // Interferon-induced 6-16 |
| 6465 // signal peptide processing // inferred from electronic annotation /// 6508 // proteolysis and peptidolysis // inferred from electronic annotation | 5615 // extracellular space // traceable author statement /// 16021 // integral to membrane // traceable author statement /// 5783 // endoplasmic reticulum // inferred from electronic annotation /// 5792 // microsome // inferred from electronic annotation /// 16020 // membrane // inferred from electronic annotation /// 16021 // integral to membrane // inferred from electronic annotation | 8233 // peptidase activity // inferred from electronic annotation /// 16787 // hydrolase activity // inferred from electronic annotation |
| — | — | IPR000508 // Peptidase S26, signal peptidase I /// IPR001733 // Peptidase S26B, eukaryotic signal peptidase |
| 6118 // electron transport // inferred from sequence or structural similarity | 5739 // mitochondrion // inferred from sequence or structural similarity /// 16021 // integral to membrane // traceable author statement /// 19867 // outer membrane // inferred from sequence or structural similarity | — |
| — | — | IPR001199 // Cytochrome b5 |
| 6790 // sulfur metabolism // inferred from sequence or structural similarity /// 8152 // metabolism // inferred from sequence or structural similarity | 5615 // extracellular space // inferred from sequence or structural similarity /// 5783 // endoplasmic reticulum // inferred from electronic annotation /// 5794 // Golgi apparatus // inferred from electronic annotation | 4065 // arylsulfatase activity // inferred from sequence or structural similarity /// 8449 // N-acetylglucosamine-6-sulfatase activity // inferred from sequence or structural similarity /// 8484 // sulfuric ester hydrolase activity // inferred from sequence or structural similarity /// 16787 // hydrolase activity // inferred from electronic annotation |
| — | — | IPR000917 // Sulfatase |
| — | — | — |
| — | 5615 // extracellular space // traceable author statement /// 16021 // integral to membrane // traceable author statement | — |
| — | — | IPR001623 // Heat shock protein DnaJ, N-terminal /// IPR002939 // Chaperone DnaJ, C-terminal /// IPR003095 // Heat shock protein DnaJ /// IPR008971 // HSP40/DnaJ peptide-binding |
| — | — | IPR007947 // CD164 related protein |
| — | — | IPR004279 // Perilipin |
| — | 5829 // cytosol // inferred from electronic annotation | IPR004279 // Perilipin |
| — | — | IPR000717 // Proteasome component region PCI /// IPR008941 // TPR-like /// IPR007110 // Immunoglobulin-like /// IPR003598 // Immunoglobulin C-2 type |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | |
|---|---|---|
| 6928 // cell motility // inferred from sequence or structural similarity | 5198 // structural molecule activity // inferred from sequence or structural similarity | IPR008273 // Cellular retinaldehyde-binding/triple function, N-terminal /// IPR001251 // Cellular retinaldehyde-binding/triple function, C-terminal /// IPR000535 // Major sperm protein (MSP) domain /// IPR008962 // PapD-like |
| — | 5615 // extracellular space // traceable author statement | 3824 // catalytic activity // inferred from sequence or structural similarity | IPR007197 // Radical SAM /// IPR006638 // Elongator protein 3/MiaB/NifB |
| — | 5615 // extracellular space // traceable author statement | 3824 // catalytic activity // inferred from sequence or structural similarity | IPR007197 // Radical SAM /// IPR006638 // Elongator protein 3/MiaB/NifB |
| — | — | — | IPR006840 // ChaC-like protein |
| 6118 // electron transport // inferred from electronic annotation | 5739 // mitochondrion // inferred from electronic annotation | 3995 // acyl-CoA dehydrogenase activity // inferred from electronic annotation /// 16491 // oxidoreductase activity // inferred from electronic annotation | IPR006090 // Acyl-CoA dehydrogenase, C-terminal /// IPR006091 // Acyl-CoA dehydrogenase, central domain /// IPR006092 // Acyl-CoA dehydrogenase, N-terminal /// IPR006089 // Acyl-CoA dehydrogenase /// IPR009075 // Acyl-CoA dehydrogenase C-terminal-like /// IPR009100 // Acyl-CoA dehydrogenase, middle and N-terminal |
| 8152 // metabolism // inferred from sequence or structural similarity | — | 5498 // sterol carrier activity // inferred from sequence or structural similarity /// 16491 // oxidoreductase activity // inferred from electronic annotation | IPR002198 // Short-chain dehydrogenase/reductase SDR /// IPR002347 // Glucose/ribitol dehydrogenase /// IPR003033 // Sterol-binding |
| 6461 // protein complex assembly // inferred from sequence or structural similarity | 16020 // membrane // inferred from sequence or structural similarity /// 16021 // integral to membrane // traceable author statement | — | IPR003780 // Cytochrome oxidase assembly |
| — | — | — | IPR001601 // Generic methyltransferase /// IPR000051 // SAM (and some other nucleotide) binding motif |
| — | — | — | IPR010370 // Transcription elongation factor A, SII-related |
| — | — | 8483 // transaminase activity // inferred from electronic annotation /// 16740 // transferase activity // inferred from electronic annotation /// 4021 // 2.6.1.2; alanine transaminase activity; 2.08e–113 // extended: Unknown 3676 // nucleic acid binding // inferred from sequence or structural similarity | IPR004839 // Aminotransferase, class I and II |
| — | — | — | — |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| 6508 // proteolysis and peptidolysis // inferred from sequence or structural similarity | 5615 // extracellular space // traceable author statement | 3824 // catalytic activity // inferred from sequence or structural similarity /// 4177 // aminopeptidase activity // inferred from sequence or structural similarity /// 4180 // carboxypeptidase activity // inferred from electronic annotation /// 4185 // serine carboxypeptidase activity // inferred from sequence or structural similarity /// 16787 // hydrolase activity // inferred from electronic annotation | Gene_Trap_Resource_2-04-02_Named_Genes | IPR001563 // Peptidase S10, serine carboxypeptidase /// IPR000379 // Esterase/lipase/thioesterase |
| — | — | — | — | — |
| 6810 // transport // inferred from electronic annotation | 5743 // mitochondrial inner membrane // inferred from sequence or structural similarity /// 16020 // membrane // inferred from electronic annotation /// 16021 // integral to membrane // inferred from electronic annotation | 5488 // binding // inferred from sequence or structural similarity | — | IPR008011 // Complex 1 LYR protein<br>IPR001993 // Mitochondrial substrate carrier /// IPR002030 // Mitochondrial brown fat uncoupling protein /// IPR002067 // Mitochondrial carrier protein /// IPR002113 // Adenine nucleotide translocator 1 |
| 7264 // small GTPase mediated signal transduction // inferred from sequence or structural similarity /// 15031 // protein transport // inferred from sequence or structural similarity | 5795 // Golgi stack // inferred from sequence or structural similarity | 3925 // small monomeric GTPase activity // inferred from sequence or structural similarity /// 3928 // RAB small monomeric GTPase activity // inferred from sequence or structural similarity /// 5525 // GTP binding // inferred from electronic annotation | — | IPR001806 // Ras GTPase superfamily /// IPR005225 // Small GTP-binding protein domain /// IPR003579 // Ras small GTPase, Rab type |
| — | — | — | — | IPR008590 // Eukaryotic protein of unknown function DUF872 /// IPR008994 // Nucleic acid-binding OB-fold |
| — | — | — | Gene_Trap_Resource_2-04-02_IMAGE_and_RIKEN_cDNAs | — |
| 6397 // mRNA processing // inferred from sequence or structural similarity /// 6406 // mRNA-nucleus export // inferred from sequence or structural similarity /// 6606 // protein-nucleus import // inferred from sequence or structural similarity /// 6810 // transport // inferred from sequence or structural similarity /// 6886 // intracellular protein transport // inferred from sequence or structural similarity /// 15031 // protein transport // inferred from sequence or structural similarity | 5856 // Band 41; cytoskeleton; 1.2e-19 // extended: Unknown<br>5622 // intracellular // inferred from sequence or structural similarity /// 5634 // nucleus // inferred from sequence or structural similarity | 8565 // protein transporter activity // inferred from sequence or structural similarity | — | IPR000299 // Band 4.1 /// IPR009065 // FERM<br>IPR002075 // Nuclear transport factor 2 (NTF2) |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | |
|---|---|---|
| 6917 // induction of apoptosis // inferred from direct assay /// 8632 // apoptotic program // inferred from direct assay | 5635 // nuclear membrane // inferred from direct assay /// 5783 // endoplasmic reticulum // inferred from direct assay /// 16021 // integral to membrane // traceable author statement | 16506 // apoptosis activator activity // inferred from direct assay | — |
| 6917 // induction of apoptosis // inferred from direct assay /// 8632 // apoptotic program // inferred from direct assay | 5635 // nuclear membrane // inferred from direct assay /// 5783 // endoplasmic reticulum // inferred from direct assay /// 16021 // integral to membrane // traceable author statement | 16506 // apoptosis activator activity // inferred from direct assay | — |
| — | 5615 // extracellular space // traceable author statement | — | — |
| — | 5615 // extracellular space // traceable author statement | 3824 // catalytic activity // inferred from sequence or structural similarity /// 16787 // hydrolase activity // inferred from electronic annotation /// 16789 // carboxylic ester hydrolase activity // inferred from sequence or structural similarity | IPR002018 // Carboxylesterase, type B /// IPR000379 // Esterase/lipase/thioesterase |
| — | — | 3676 // nucleic acid binding // inferred from sequence or structural similarity /// 4386 // helicase activity // inferred from sequence or structural similarity /// 5524 // ATP binding // inferred from sequence or structural similarity /// 8026 // ATP dependent helicase activity // inferred from sequence or structural similarity /// 16787 // hydrolase activity // inferred from electronic annotation | IPR001410 // DEAD/DEAH box helicase /// IPR001650 // Helicase, C-terminal |
| — | — | — | — |
| — | — | — | IPR010916 // TONB Box N terminus IPR002114 // HPr serine |

TABLE 1-continued

Directional Analysis of Gene Expression comparison of Calorie Restricted Mice and Oxaloacetate Mice to Control Mice change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| — | — | — | phosphorylation site IPR002097 // Profilin/allergen |
| — | — | 4842 // HECT; ubiquitin-protein ligase activity; 3.3e−70 // extended: Unknown | IPR000569 // HECT domain (Ubiquitin-protein ligase) |
| 6412 // protein biosynthesis // inferred from electronic annotation /// 6414 // translational elongation // inferred from electronic annotation | 5739 // mitochondrion // inferred from electronic annotation | 3746 // translation elongation factor activity // inferred from electronic annotation /// 5525 // GTP binding // inferred from electronic annotation /// 8547 // protein-synthesizing GTPase activity // inferred from electronic annotation /// 4563 // 3.2.1.52; beta-N-acetylhexosaminidase activity; 3.22e−177 // extended: Unknown /// 4563 // Glyco_hydro_20b; beta-N-acetylhexosaminidase activity; 2.1e−67 // extended: Unknown | IPR000795 // Protein synthesis factor, GTP-binding /// IPR000640 // Elongation factor G, C-terminal /// IPR004161 // Elongation factor Tu, domain 2 /// IPR005517 // Elongation factor G, domain IV /// IPR009000 // Translation factor /// IPR009022 // Elongation factor G, III and V /// IPR005225 // Small GTP-binding protein domain |
| — | — | — | — |
| — | — | — | IPR000379 // Esterase/lipase/thioesterase |
| — | — | — | IPR002328 // Zinc-containing alcohol dehydrogenase |
| — | — | — | |

TABLE 2

1.7 Fold Cut-Off in Either Calorie Restricted or Oxaloacetate Gene Expression Directional Analysis of Gene Expression Comparison of Calorie Restricted Mice and Oxaloacetate Mice to Control Mice Change in Gene Activity Expressed by Oxaloacetate and CR Mice Versus Control Mice Expression for Genes Shown to Change Commonly Affymatrix Mouse Genome 430 2.0 Array

| | | | CR to C | | OX to C | | |
|---|---|---|---|---|---|---|---|
| Gene Symbol | Gene Title | Affymatrix No. | Signal Log Ratio | Change | Signal Log Ratio | Change | Gene Movement in Same Direction? |
| Cyp2b9 | cytochrome P450, family 2, subfamily b, polypeptide 9 | 3985 | −2.5 | D | −1 | D | YES |
| Dgat2l1 | diacylglycerol O-acyltransferase 2-like 1 | 3899 | −1.8 | D | −1.4 | D | YES |
| Fabp4 | fatty acid binding protein 4, adipocyte | 19390 | −1.7 | D | −1.4 | D | YES |
| Fabp5 | fatty acid binding protein 5, epidermal | 417 | 1.2 | I | 1.8 | I | YES |
| Foxq1 | forkhead box Q1 | 6994 | 1.1 | I | 2.1 | I | YES |
| Foxq1 | forkhead box Q1 | 30006 | 1.9 | I | 2.2 | I | YES |
| Ifit1 | interferon-induced protein with tetratricopeptide repeats 1 | 18910 | −2 | D | −0.5 | D | YES |
| Lcn2 | lipocalin 2 | 12006 | −1.8 | D | −0.7 | D | YES |
| Lgals1 | lectin, galactose binding, soluble 1 | 3968 | −1.7 | D | −0.5 | D | YES |
| LOC209387 | tripartite motif protein 30-like | 22024 | −1.9 | D | −0.4 | D | YES |
| Ly6d | lymphocyte antigen 6 complex, locus D | 1325 | −3.4 | D | −2.2 | D | YES |
| Saa1 | serum amyloid A 1 | 18915 | −1.9 | D | −0.5 | D | YES |
| Saa2 | serum amyloid A 2 | 3470 | −1.8 | D | −0.3 | D | YES |
| Saa2 | serum amyloid A 2 | 17502 | −1.9 | D | −0.5 | D | YES |
| Serpina4-ps1 | serine (or cysteine) proteinase inhibitor, clade A, member 4, pseudogene 1 | 35241 | 3.6 | I | 1.8 | I | YES |
| Serpinb1a | serine (or cysteine) proteinase inhibitor, clade B, member 1a | 713 | −1.7 | D | −1.2 | D | YES |
| Socs2 | suppressor of cytokine signaling 2 | 17285 | 2.8 | I | 0.8 | I | YES |
| Trim2 | tripartite motif protein 2 | 16727 | −1.7 | D | −0.4 | D | YES |
| Tubb2 | tubulin, beta 2 | 11606 | −2.7 | D | −1 | D | YES |
| Ucp2 | uncoupling protein 2, mitochondrial | 16364 | −1.7 | D | −0.5 | D | YES |
| Usp18 | ubiquitin specific protease 18 | 2586 | −1.8 | D | −0.8 | D | YES |
| — | Mus musculus transcribed sequence with weak similarity to protein sp: P32456 (H. sapiens) GBP2_HUMAN Interferon-induced guanylate-binding protein 2 (Guanine nucleotide-binding protein 2) | 15668 | −2.6 | D | −0.9 | D | YES |
| — | Mus musculus similar to cytochrome P450 2B4-rat (fragments) (LOC232993), mRNA | 17655 | −3.6 | D | −4.2 | D | YES |
| — | Mus musculus transcribed sequences | 18738 | −1.9 | D | −1.2 | D | YES |
| — | Mus musculus transcribed sequences | 38815 | −2.9 | D | −0.7 | D | YES |
| — | Mus musculus transcribed sequences | 43312 | −2.1 | D | −2.1 | D | YES |
| — | Mus musculus transcribed sequences | 45080 | −1.8 | D | −0.7 | D | YES |
| 1110067D22Rik | RIKEN cDNA 1110067D22 gene | 19440 | −1.8 | D | −0.6 | D | YES |
| 1600032L17Rik | RIKEN cDNA 1600032L17 gene | 23279 | −0.8 | D | −1.7 | D | YES |
| 2510004L01Rik | RIKEN cDNA 2510004L01 gene | 5268 | −1.8 | D | −0.9 | D | YES |
| 2510004L01Rik | RIKEN cDNA 2510004L01 gene | 14650 | −2.1 | D | −0.6 | D | YES |
| 4933433D23Rik | RIKEN cDNA 4933433D23 gene | 5094 | 1.6 | I | 0.7 | I | YES |
| 5730494M16Rik | RIKEN cDNA 5730494M16 gene | 44727 | −2.2 | D | −1.2 | D | YES |
| 9130019P20Rik | RIKEN cDNA 9130019P20 gene | 39136 | 2 | I | 0.6 | I | YES |
| A430056A10Rik | RIKEN cDNA A430056A10 gene | 7814 | −2.6 | D | −1.5 | D | YES |
| AW539457 | expressed sequence AW539457 | 26927 | −1.8 | D | −0.9 | D | YES |

TABLE 2-continued 1.7 Fold Cut-Off in Either Calorie Restricted or Oxaloacetate Gene Expression Directional Analysis of Gene Expression Comparison of Calorie Restricted Mice and Oxaloacetate Mice to Control Mice Change in Gene Activity Expressed by Oxaloacetate and CR Mice Versus Control Mice Expression for Genes Shown to Change Commonly Affymatrix Mouse Genome 430 2.0 Array

| | | |
|---|---|---|
| Mice Fed Oxaloacetate with Genes Moving in Same Direction as Calorie Restricted Mice (1.7 Fold Cut Off) | | 36 |
| Mice Fed Oxaloacetate with Genes Moving in Opposite Direction as Calorie Restricted Mice (1.7 Fold Cut Off) | | 0 |
| Percentage of Mice Fed Oxaloacetate with Genes Moving in Same Direction as Calorie Restricted Mice | | 100.0% |

| Gene Ontology Biological Process | Gene Ontology Cellular Component | Gene Ontology Molecular Function | Pathway | InterPro |
|---|---|---|---|---|
| 6118 // electron transport // inferred from electronic annotation | 5783 // endoplasmic reticulum // inferred from electronic annotation /// 5792 // microsome // inferred from electronic annotation /// 16020 // membrane // inferred from electronic annotation | 4497 // monooxygenase activity // inferred from electronic annotation /// 16491 // oxidoreductase activity // inferred from electronic annotation /// 16712 // oxidoreductase activity, acting on paired donors, with incorporation or reduction of molecular oxygen, reduced flavin or flavoprotein as one donor, and incorporation of one atom of oxygen // inferred from electronic annotation | — | IPR001128 // Cytochrome P450 /// IPR002401 // E-class P450, group I /// IPR008068 // E-class P450, CYP2B |
| — | — | 8415 // acyltransferase activity // inferred from electronic annotation /// 16740 // transferase activity // inferred from electronic annotation | — | IPR007130 // Diacylglycerol acyltransferase /// IPR006662 // Thioredoxin type domain |
| 6810 // transport // inferred from electronic annotation | — | 5215 // transporter activity // inferred from electronic annotation /// 5488 // binding // lipid binding // inferred from electronic annotation /// 8289 // lipid binding // inferred from electronic annotation | — | IPR000566 // Lipocalin-related protein and Bos/Can/Equ allergen /// IPR000463 // Cytosolic fatty-acid binding protein |
| 6810 // transport // inferred from electronic annotation | — | 5215 // transporter activity // inferred from electronic annotation /// 5488 // binding // lipid binding // inferred from electronic annotation /// 8289 // lipid binding // inferred from electronic annotation | — | IPR000566 // Lipocalin-related protein and Bos/Can/Equ allergen /// IPR000463 // Cytosolic fatty-acid binding protein |
| 6355 // regulation of transcription, DNA-dependent // inferred from electronic annotation | 5634 // nucleus // inferred from electronic annotation /// 5667 // transcription factor complex // inferred from electronic annotation | 3677 // DNA binding // inferred from electronic annotation /// 3700 // transcription factor activity // inferred from electronic annotation | — | IPR001766 // Fork head transcription factor /// IPR009058 // Winged helix DNA-binding |
| 6355 // regulation of transcription, DNA-dependent // inferred from electronic annotation | 5634 // nucleus // inferred from electronic annotation /// 5667 // transcription factor complex // inferred from electronic annotation | 3677 // DNA binding // inferred from electronic annotation /// 3700 // transcription factor activity // inferred from electronic annotation | — | IPR001766 // Fork head transcription factor /// IPR009058 // Winged helix DNA-binding |
| 6955 // immune response // inferred from electronic annotation | — | — | — | IPR001440 // TPR repeat /// IPR008941 // TPR-like |
| 6810 // transport // inferred from electronic annotation | 5615 // extracellular space // traceable author statement | 5215 // transporter activity // inferred from electronic annotation /// 5488 // binding // inferred from sequence or structural similarity | — | IPR000566 // Lipocalin-related protein and Bos/Can/Equ allergen /// IPR002345 // Lipocalin /// IPR003087 // Neutrophil gelatinase-associated lipocalin |

TABLE 2-continued 1.7 Fold Cut-Off in Either Calorie Restricted or Oxaloacetate Gene Expression Directional Analysis of Gene Expression Comparison of Calorie Restricted Mice and Oxaloacetate Mice to Control Mice Change in Gene Activity Expressed by Oxaloacetate and CR Mice Versus Control Mice Expression for Genes Shown to Change Commonly Affymetrix Mouse Genome 430 2.0 Array

| | | | |
|---|---|---|---|
| 7157 // heterophilic cell adhesion // inferred from electronic annotation /// 45445 // myoblast differentiation // inferred from direct assay | 5615 // extracellular space // inferred from direct assay | 5529 // sugar binding // inferred from electronic annotation | IPR001079 // Galectin, galactose-binding lectin /// IPR008985 // Concanavalin A-like lectin/glucanase |
| 6952 // defense response // inferred from electronic annotation | 5615 // extracellular space // traceable author statement /// 5886 // plasma membrane // inferred from electronic annotation /// 16020 // membrane // inferred from electronic annotation | — | IPR003632 // Cell-surface glycoprotein Ly-6/CD59 /// IPR001526 // CD59 antigen |
| 6953 // acute-phase response // inferred from electronic annotation | 5576 // extracellular // inferred from electronic annotation | — | — |
| 6953 // acute-phase response // inferred from electronic annotation | 5576 // extracellular // inferred from electronic annotation | 5319 // lipid transporter activity // inferred from electronic annotation /// 5515 // protein binding // inferred from physical interaction /// 3794 // SAA_proteins; acute-phase response protein activity; 6.5e-78 // extended: Unknown | IPR000096 // Serum amyloid A protein |
| 6953 // acute-phase response // inferred from electronic annotation | 5576 // extracellular // inferred from electronic annotation | 5319 // lipid transporter activity // inferred from electronic annotation /// 5515 // protein binding // inferred from physical interaction /// 3794 // SAA_proteins; acute-phase response protein activity; 1.3e-72 // extended: Unknown | IPR000096 // Serum amyloid A protein |
| — | — | 5319 // lipid transporter activity // inferred from electronic annotation /// 5515 // protein binding // inferred from physical interaction /// 3794 // SAA_proteins; acute-phase response protein activity; 1.3e-72 // extended: Unknown | IPR000215 // Serpin |
| — | — | 4866 // endopeptidase inhibitor activity // inferred from electronic annotation /// 4867 // serine-type endopeptidase inhibitor activity // inferred from electronic annotation | IPR000215 // Serpin |
| 42176 // regulation of protein catabolism // inferred from physical interaction | — | 4866 // endopeptidase inhibitor activity // inferred from electronic annotation /// 4867 // serine-type endopeptidase inhibitor activity // inferred from electronic annotation /// 8233 // peptidase activity // inferred from electronic annotation | — |
| 1558 // regulation of cell growth // inferred from electronic annotation /// 7165 // signal transduction // inferred from electronic annotation /// 7242 // intracellular signaling cascade // inferred from electronic annotation /// 40014 // regulation of body size // inferred from mutant phenotype /// 45666 // positive regulation of neuron differentiation // inferred from direct assay | — | — | Gene_Trap_Resource_2-04-02_Named_Genes /// IPR000980 // SH2 motif /// IPR001496 // SOCS protein, C-terminal |
| — | 5622 // intracellular // inferred from electronic annotation /// 5737 // cytoplasm // inferred from direct assay | 5515 // protein binding // inferred from physical interaction /// 8270 // zinc ion binding // inferred from electronic annotation | IPR01258 // NHL repeat /// IPR001841 // Zn-finger, RING |

TABLE 2-continued 1.7 Fold Cut-Off in Either Calorie Restricted or Oxaloacetate Gene Expression Directional Analysis of Gene Expression Comparison of Calorie Restricted Mice and Oxaloacetate Mice to Control Mice Change in Gene Activity Expressed by Oxaloacetate and CR Mice Versus Control Mice Expression for Genes Shown to Change Commonly Affymatrix Mouse Genome 430 2.0 Array

| | | | |
|---|---|---|---|
| 7017 // microtubule-based process // inferred from electronic annotation | 5874 // microtubule // inferred from electronic annotation | 5200 // structural constituent of cytoskeleton // inferred from electronic annotation /// 5525 // GTP binding // inferred from electronic annotation | — | IPR001298 // Filamin/ABP280 repeat /// IPR000315 // Zn-finger, B-box /// IPR003649 // B-box, C-terminal IPR008280 // Tubulin/FtsZ, C-terminal /// IPR002453 // Beta tubulin /// IPR003008 // Tubulin/FtsZ, GTPase /// IPR000217 // Tubulin /// IPR010916 // TONB Box N terminus |
| 6810 // transport // inferred from electronic annotation /// 6839 // mitochondrial transport // inferred from electronic annotation | 5739 // mitochondrion // inferred from sequence or structural similarity /// 16020 // membrane // inferred from electronic annotation /// 16021 // integral to membrane // inferred from electronic annotation /// 19866 // inner membrane // inferred from electronic annotation | 5488 // binding // inferred from electronic annotation | Electron_Transport_Chain | IPR001993 // Mitochondrial substrate carrier /// IPR002030 // Mitochondrial brown fat uncoupling protein /// IPR002113 // Adenine nucleotide translocator 1 |
| 6511 // ubiquitin-dependent protein catabolism // inferred from electronic annotation | — | 4197 // cysteine-type endopeptidase activity // inferred from electronic annotation /// 4221 // ubiquitin thiolesterase activity // inferred from electronic annotation /// 8234 // cysteine-type peptidase activity // inferred from electronic annotation /// 16787 // hydrolase activity // inferred from electronic annotation | — | IPR001394 // Peptidase C19, ubiquitin carboxyl-terminal hydrolase family 2 |
| 6118 // p450; electron transport; 8.2e-195 // extended: Unknown | — | — | — | — |
| — | — | — | — | — |
| — | — | — | — | — |
| — | — | 5529 // sugar binding // inferred from sequence or structural similarity | — | IPR001079 // Galectin, galactose-binding lectin /// IPR008985 // Concanavalin A-like lectin/glucanase |
| — | — | — | — | IPR005036 // Putative phosphatase regulatory subunit |
| — | 5615 // extracellular space // traceable author statement | 3824 // catalytic activity // inferred from sequence or structural similarity | — | IPR007197 // Radical SAM /// IPR006638 // Elongator protein 3/MiaB/NifB |

TABLE 2-continued 1.7 Fold Cut-Off in Either Calorie Restricted or Oxaloacetate Gene Expression Directional Analysis of Gene Expression Comparison of Calorie Restricted Mice and Oxaloacetate Mice to Control Mice Change in Gene Activity Expressed by Oxaloacetate and CR Mice Versus Control Mice Expression for Genes Shown to Change Commonly Affymatrix Mouse Genome 430 2.0 Array

| | 5615 // extracellular space // traceable author statement | 3824 // catalytic activity // inferred from sequence or structural similarity | | IPR007197 // Radical SAM /// IPR006638 // Elongator protein 3/MiaB/NifB |
|---|---|---|---|---|
| 6810 // transport // inferred from electronic annotation | 5743 // mitochondrial inner membrane // inferred from sequence or structural similarity /// 16020 // membrane // inferred from electronic annotation /// 16021 // integral to membrane // inferred from electronic annotation | 5488 // binding // inferred from sequence or structural similarity | | IPR001993 // Mitochondrial substrate carrier /// IPR002030 // Mitochondrial brown fat uncoupling protein /// IPR002067 // Mitochondrial carrier protein /// IPR002113 // Adenine nucleotide translocator 1 |
| — | — | — | — | — |
| — | — | — | — | IPR010916 // TONB Box N terminus |
| — | — | — | — | IPR002097 // Profilin/allergen |
| — | — | — | — | — |

Table 1 shows a gene expression directional analysis indicating that 98% of the genes that changed expression from the control group and were commonly expressed also in the oxaloacetate supplemented group and Calorie Restricted group moved in the same direction (up regulated or down regulated). Table 1 further illustrates that both calorie restriction and the supplementation of oxaloacetate in the diet causes changes in gene expression as compared to the expression genes in a control group fed as much food as they desired (fed ad libitum). It documents the 363 genes that change in common expression from the control group, and the directional analysis of the change in gene expression for oxaloacetate and calorie restricted mice as compared to the control group.

Table 2 shows increases and decreases in gene expression of commonly expressed changed genes of 1.7 fold in either oxaloacetate supplemented mice or calorie restricted mice as compared to a control group. Table 2 demonstrates that genes expressed by either the calorie restricted group of mice or the oxaloacetate supplemented group of mice that resulted in a 1.7 or greater fold increase (or decrease) in expression as compared to the control group. Both average lifespan and maximal lifespan of the individual are substantially increased with the application of excess oxaloacetate to the organism. However, unlike CR, there is no need for reduction in caloric intake. It is interesting to note that in the liver no increase in the Sirt1 gene in the mice was observed, however this does not exclude the increase of Sirt1 gene in other tissues. In our C. elegans experiments represented in FIG. 3, Sir2 (and their homologues, such as Sirt1 in humans) was shown to add approximately a 10% increase in lifespan over control animals. Other beneficial genes, turned on in CR, operate in a parallel but independent pathway to the Sir2 type genes are also activated by oxaloacetate and increase lifespan by greater amounts, as much as up to an additional 26%. Between the activation of the Sir2 type genes and the other beneficial genes, a total increase of up to 36% in lifespan over control animals has been shown to be obtainable.

In one embodiment of the invention, a nutritional supplement comprising an effective dose of oxaloacetate is provided to extend the lifespan of an individual and to reduce the onset of age-related disease. Oxaloacetate acts to reduce NADH levels in the cytosol of the cell, which increases the NAD+/NADH ratio to levels seen during CR, but without a restriction in calories or genetic modification of the individual. External cellular contact with an oxaloacetate compound, and subsequent transfer of the oxaloacetate into the cell, leads to metabolic changes that increase the NAD/NADH ratio and activate beneficial genes. The oxaloacetate is converted to malate by interaction with cytosolic malate dehydrogenase. In this conversion, NADH is converted to NAD+, which increases the intercellular NAD+/NADH ratio. The present invention is based, in part, on the surprising and novel discovery that the increase in NAD+/NADH ratio signals the activation of the beneficial genes that then act upon the cell to increase lifespan and reduce the onset of age related disease.

In another embodiment of the current invention, methods for extending lifespan and reducing the onset of age-related disease is provided comprising administering an effective dose of oxaloacetate to an individual in need thereof. As used herein, the phrase "age-related disease" refers to any number of conditions attributable to advance in age. These conditions include, without limitation, osteoporosis, bone loss, arthritis, stiffening joints, cataracts, macular degeneration, and heart disease including atherosclerosis and dyslipidemia. The phrase "age related disease" further encompasses neurodegenerative diseases such as Alzheimer Disease and related disorders, Parkinson's Disease, and cancer. It has been observed that mammals which undergo CR have a reduced incidence of neurological disorders, including Alzheimer disease. The addition of excess oxaloacetate to the cytosol of the cell results in the same signaling mechanism in the cells as CR to turn on the necessary beneficial genes necessary for neurological protection.

Also included within the meaning of "age-related disease" are cosmetic concerns such as loss of skin firmness and elasticity as well as increase wrinkle depth and pore sizes associated with aging. "Age-related disease" further includes other symptoms associated with aged skin such as wrinkles, rhytids, sun damage, dull appearance of the skin, sagging skin, jowls, keratosis, melasma, and hyperpigmentation.

Oxaloacetate can be used to protect DNA and enhance DNA repair in skin and other tissues subjected to ultra violet (UV) light. Unlike a sunscreen that blocks UV, oxaloacetate enhances the repairs to DNA in a similar fashion as occurs in CR (Lipman et al.) because addition of excess oxaloacetate mimics the same intercellular signaling conditions as exist in CR. CR has been shown to enhance repairs to DNA in many studies as per mechanisms outlined in references 36, 37, 38, 39 40 and 44. One advantage of using oxaloacetate to mimic CR rather than utilizing CR is that oxaloacetate can be localized on the skin, to create "localized CR" conditions in just the contacted skin, while all other forms of CR take place in the entire organism. Thus, oxaloacetate can be combined with a UV sunblock or cosmetic to produce on-going enhancement of DNA repair to skin cells from UV damage. Reduction in this damage and repair of the damage leads to maintaining younger looking skin for a longer period of time, leads to reduced incidences of skin cancer and may be used as a treatment or assist in the treatment of skin cancer.

Oxaloacetate can act in another pathway to extend lifespan and reduce the onset of age related disease by interfering with insulin signaling. Insulin-like signaling has been shown to also control aging, metabolism and development. Mutations in the daf-2 gene and age-1 phosphoinositide 3-kinase gene of Caenorhabditis elegans have lead to increases in lifespan. The insulin-like signaling pathway may also be affected by caloric restriction to retard aging. Oxaloacetate has been shown to block at least a portion of the insulin signaling pathways by Kahn (Kahn, et al, Insulin Increases NADH/NAD+ Redox State, Which Stimulates Guanylate Cyclase in Vascular Smooth Muscle, American Journal of Hypertension, Ltd. 2002, Vol. 15, 273-279). NADH is also important to insulin signaling as shown by MacDonald (MacDonald, et al, Histochemical Evidence for Pathways Insulin Cells Use to Oxidize Glycolysis-Derived NADH, Metabolism, Vol. 51, No. 3 (March), 2002, pp 318-321), and oxaloacetate added to the cytosol reduces the availability of NADH.

A third pathway to extend lifespan and reduce the onset of age related disease by oxaloacetate may be in the protective effects of oxaloacetate to mitochondrial DNA. Yamamoto, et al (Yamamoto et al, "Effect of alpha-ketoglutarate and Oxaloacetate on brain mitochondrial DNA damage and seizures induced by kainic acid in mice", Toxicology Letters: 2003: 143: 115-122) showed that both Oxaloacetate and its precursor alpha-ketoglutarate protected brain mitochondrial DNA from damage in mice. Yamamoto failed to teach, however, if this protection could increase lifespan or reduce the onset of age related disease, as was discovered in this invention.

Oxaloacetate can be administered alone to extend lifespan and reduce the onset of age-related disease or in combination with another therapeutic agent. As used herein, the term "therapeutic agent" is a broad term that includes antibacterial agents, antiviral agents, anti-fungals, chemotherapeutics, antihistamines, proteins, enzymes, hormones, non-steroidal anti-inflammatory drugs, immunostimulatory compounds such as cytokines, and steroids. Suitable antibiotics include, without limitation, amoxicillin, ampicillin, bacampicillin, carbenicillin indanyl, mezlocillin, peperacillin, ticarcillin, amoxicillin-clavulanic acid, ampicillin-sulbactam, benzylpenicillin, cloxacillin, dicloxacillin, methicillin, oxacillin, penicillin G, penicillin V, piperacillin+tazobactam, ticarcillin+clavulanic acid, nafeillin, cefadroxil, cefazolin, cephalexin, cephalothin, cephapirin, cephradine, cefaclor, cefamandol, cefonicid, cefotetan, cefoxitin, cefprozil, ceftmetazole, cefuroxime, cefuroxime axetil, larcarbef, cefdinir, ceftibuten, cefoperazone, cefixime, cefotaxime, cefpodoxime proxetil, ceftazidime, ceftizoxime, ceftriaxone, cefepime, azithromycin, clarithromycin, clindamycin, erythromycin, lincomycin, troleandomycin, cinoxacin, ciprofloxacin, enoxacin, gatifloxacin, grepafloxacin, levofloxacin, lomefloxacin, moxifloxacin, nalidixic acid, norfloxacin, ofloxcin, sparfloxacin, trovafloxacin, oxolinic acid, gemifloxacin, perfloxacin, imipenem cilastatin, meropenem, aztreonam, amikacin, gentamicin, kanamycin, neomycin, netilmicin, streptomycin, tobramycin, paaromomycin, teicoplanin, vancomycin, demeclocycline, doxycycline, methacycline, minocycline, oxytetracycline, tetracycline, chlortetracycline, mafenide, silver sulfadiazine, sulfacetamide, sulfadiazine, sulfamethoxazole, sulfasalazine, sulfisoxazole, trimethoprim-sulfamethoxazole, sulfamethizole, rifabutin, rifampin, rifapentine, linezolid, quinopristin+dalfopristin, chlroamphenico, colistemetate, fosfomycin, isoniazid, methenamnine, metronidazol, mupirocin, nitrofurantoin, nitrofurazone, novobiocin, spectinomycin, trimethoprim, colistin, cycloserine, capreomycin, ethionamide, pyrazinamide, para-aminosalicyclic acid, and erythromycin ethylsuccinate+sulfisoxazole. Examples of suitable chemotherapeutic agents include an anticancer agent like cyclophosphamide, chlorambucil, melphalan, estramustine, iphosphamide, prednimustin, busulphan, tiottepa, carmustin, lomustine, methotrexate, azathioprine, mercaptopurine, thioguanine, cytarabine, fluorouracil, vinblastine, vincristine, vindesine, etoposide, teniposide, dactinomucin, doxorubin, dunorubicine, epirubicine, bleomycin, nitomycin, cisplatin, carboplatin, procarbazine, amacrine, mitoxantron, tamoxifen, nilutamid, or aminoglutemide. Immunostimulatory compounds include, without limitation, a vaccine adjuvant, a vaccine, a peptide, a cytokine like IL-1, IL-2, IL-12, IL-15, IFN-α, IFN-β, or IFN-γ, or a flavonoid like flavone acetic acids and xanthenone-4-acetic acids.

When administered in combination with another therapeutic agent, oxaloacetate can be administered separately or as a single formulation with the antibiotic. If administered separately, oxaloacetate should be given in a temporally proximate manner with the antibiotic. In one embodiment, the therapeutic agent and oxaloacetate are given within one week of each other. In another embodiment, the therapeutic agent and oxaloacetate are given within twenty-four hours of each other. In yet another embodiment, the therapeutic agent and oxaloacetate are given within one hour of each other. The administration can be by oral, local, or by systemic injection or infusion. Other methods of administration may also be suitable as will be appreciated by one of skill in the art.

Methods and compositions are described herein for the modulation of body weight, reduction of fat, treatment of obesity, reduction in cellulite accumulation. In addition to the activation of beneficial CR genes, the administration of oxaloacetate results in the reduction of fat, despite the amount of food consumed, as the differentiation of cells into fat cells is blocked by the activation of Sir2 (Sirt1 in humans), which also causes current fat cells shed their fat. Activation of the human Sirt1 gene that is normally activated in CR blunts the protein PPAR gamma that activates fat storage genes. Sirt1 activation also causes formed fat cells to shed their fat. In some embodiments of the invention, a method of treating obesity via the administration of an effective dose of oxaloacetate is provided. Obesity, defined as an excess of body fat relative to lean body mass, also contributes to a host of other diseases including, without limitation, increased incidences of coronary artery disease, stroke, and diabetes. Hence, the administration of oxaloacetate would be beneficial not only for treating obesity but also for treating the diseases associated with obesity. In one embodiment, a method of treating a non-obese individual for the reduction of unwanted body fat is provided comprising administering an effective dose of oxaloacetate.

In another embodiment of the current invention, oxaloacetate can be used to reduce the incidence of cancer, or to stop the spread of cancer to non-cancerous cells. Mammals that undergo CR have up to a 40% lower cancer rate. CR has been shown to enhance the repair of DNA (Lipman et al, "The influence of dietary restriction on DNA repair in rodents: a preliminary study", Mech Ageing Dev 1989: 48: 135-43; Weraarchakul et al, "The effect of aging and dietary restriction on DNA repair", Exp Cell Res 1989; 181:197-204; Licastro et al, "Effect of dietary restriction upon the age-associated decline of lymphocyte DNA repair activity in mice", Age 1988: 11: 48-52; Srivastava et al, "Decreased fidelity of DNA polymerases and decreased DNA excision repair in aging mice: Effects of caloric restriction", Biochem Biophys Res Commun 1992: 182: 712-21; Tilley et al, "Enhanced unscheduled DNA synthesis by secondary cultures of lung cells established from calorically restricted aged rats", Mech Ageing Dev 1992: 63" 165-76), which may be one reason for the reduction in cancer rates. Addition of excess oxaloacetate to the cytosol of the cell results in the same signaling mechanism in the cells as CR to turn on the necessary beneficial genes necessary for cancer protection. Malignancies against which the treatment may be directed include, but are not limited to, primary and metastatic malignant solid tumor disease, and hematological malignancies such as acute and chronic myelogenous leukemia, acute and chronic lymphatic leukemia, multiple myeloma, Waldenstrom's macroglobulinemia, hairy cell leukemia, myelodisplastic syndrome, polycytaemia vera, and essential thrombocytosis.

Methods and compositions for countering the effects of alcohol composition are disclosed herein. The administration of oxaloacetate results in an increase in NAD+/NADH ratio, which can quickly counter the effects of alcohol consumption and reduce the symptoms associated with over-indulgence of alcohol. These symptoms include, without limitation, headache, poor sense of overall well-being, diarrhea, loss of appetite, shakiness, fatigue, and nausea. Other symptoms include decreased reaction times, less ability to concentrate, lower managerial skills, and increased risk for injury, even after some of the more obvious hang-over symptoms are gone and alcohol can no longer be detected in the blood. The method includes identifying an individual who has consumed amounts of alcohol and administering to that individual an effective amount of oxaloacetate. As used herein, an effective amount of oxaloacetate includes from about 0.5 mg to about 75 mg of oxaloacetate per kg of weight. In a preferred embodiment, an effective amount of oxaloacetate is between about 2 mg to about 40 mg of oxaloacetate per kg of body weight. As will be described in greater detailed below, in a preferred embodiment, oxaloacetate can be administered via injection or ingestion.

Pharmaceutical Preparations and Methods of Administration

Oxaloacetate can be administered to an individual at therapeutically effective doses to prolong lifespan and/or treat or ameliorate age related diseases and body weight disorders. As used herein, "oxaloacetate" includes oxaloacetic acid, the salt of the acid, or oxaloacetate in a buffered solution as well as mixtures thereof. The term similarly includes oxaloacetate precursors such as alpha-ketoglutarate and aspartate.

A therapeutically effective dose refers to that amount of oxaloacetate sufficient to result in the desired effect such as the prolongation of life span, treatment of age-related disorders, and/or amelioration of symptoms of body weight disorders.

Effective Dose

Toxicity and therapeutic efficacy of oxaloacetate can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. The LD50 of alpha-ketoglutarate for mice is above 5 g/kg of body weight. The LD50 of oxaloacetate is above 5 g/kg of body weight. Oxaloacetate has a very low toxicity, as would be expected from a chemical involved in the Citric Acid Cycle of every cell.

Toxicity studies of oxaloacetate run in Japan in 1968 on rats indicates that levels of oxaloacetate at 83 mg/kg of body weight caused changes in pancreatic islets. Some islets were decreased in size and hyperemic, alpha cells being atrophic, while beta cells were hypertrophic and stained densely. At lower doses, 41 mg/kg of body weight, the pancreas of the rates only demonstrated proliferation and hyperplasia of the islet cells. The liver, hypophysis, adrenals and gonadal glands showed no particular changes (Yoshikawa, Kiyohiko, "Studies on Anti-diabetic Effect of Sodium Oxaloacetate", Tohoku Journal of Experimental Medicine, 1968, volume 96, pp. 127-141). Further studies by the inventor using oxaloacetate in mice at a dosage 300% to 50,000% greater than proposed in humans indicated negative toxicity—the mice live longer than the control group. The safety of this compound in reasonable amounts is assured because the compound is a human metabolite.

In clinical studies examining the effect of oxaloacetate on diabetes in humans, 21 diabetic patients received 100 mg to 1,000 mg (2-10 mg/kg of body weight). There were no negative side effects. Fasting blood glucose levels dropped an average of 24% in the patients and urine glucose levels dropped in 19 out of the 21 patients (Yoshikawa).

An example of an effective dose of oxaloacetate administered by an intravenous injection is from between about 0.5 mg to about 1 g of oxaloacetate for each kg of body weight. In a preferred embodiment, the effective dose of oxaloacetate is between about 2.0. mg and about 40 mg for each kg of body weight. The effective dose can be administered in multiple injections over several hours, or continuously. Effective oral dosing would likewise range from about 0.5 mg to about 1 g of oxaloacetate for each kg of body weight with the preferred effective dosage range between about 2 mg to about 40 mg of oxaloacetate for each kg of body weight. For example, an adult male weighing approximately 80 kg would be administered between about 150 mg to about 3.5 g of oxaloacetate orally per day. Dermally, topical formulations comprising concentrations of about 0.5 to 16 mM of oxaloacetate are effective. CR studies indicate that restricting calories every-other-day yields the same beneficial results as daily CR. Similarly, in some embodiments, oxaloacetate can be administered every-other-day, as once the genes are activated, the effect lasts for at least a two-day period of time. In other embodiments, oxaloacetate is administered 3 times per day after each meal.

Formulations

Pharmaceutical compositions for use in accordance with the present invention may be formulated in conventional manner using one or more physiologically acceptable carriers or excipients. Thus, oxaloacetate and its physiologically acceptable salts and solvates may be formulated for administration by inhalation or insufflation (either through the mouth or the nose) or oral, buccal, topical, transdermal, parenteral, or rectal administration. In the case of inhalation, the administration of oxaloacetate will provide aging benefits directly to lung tissue, even if the dosage of oxaloacetate administered is less than is needed to benefit the entire organism. Inhalation of oxaloacetate will delay the on-set of age-related diseases of the lungs and will provide protection from lung diseases.

Oxaloacetate is acidic. The acidity is unlikely to affect organisms that ingest the compound in beneficial amounts as the interior conditions of the stomach are also very acidic. The acidity may affect other tissues, including but not limited to the skin or lungs, that may benefit from the direct application of oxaloacetate. Therefore, in another embodiment, a composition of matter can be created by mixing oxaloacetate with a buffer solution or a base or used as a salt of oxaloacetate so the delivered compound is not caustic. This will enable higher concentrations of oxaloacetate to be delivered safely to the organism, especially if the oxaloacetate is not delivered by oral ingestion.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p- hydroxybenzoates or sorbic acid). The preparations may also contain buffer salts, flavoring, coloring and sweetening agents as appropriate.

While the absorption of oxaloacetate from the digestive tract will increase the entire organism's oxaloacetate levels, the immediate contact of oxaloacetate to the cells in the digestive tract will preferentially be in contact with the digestive tract cells, allowing the reduction in age-related diseases such as colon cancer, even if the ingested amounts of oxaloacetate are insufficient to provide benefit to the entire organism.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

For the protection of DNA from UV exposure and to enhance DNA repair of the UV damage, also for the treatment of rhytids or skin wrinkles, a preferred method of administration of oxaloacetate is by topical application. The topical pharmaceutical and cosmetic compositions of the present invention maybe made into a wide variety of product types. These include, but are not limited to lotions, creams, beach oils, gels, sticks, sprays, ointments, pastes, mousses and cosmetics. These product types may comprise several types of pharmaceutical or cosmetic carrier systems including, but not limited to solutions, emulsions, gels and solids. The topical pharmaceutical and cosmetic compositions of the present invention formulated as solutions typically include a pharmaceutically-acceptable aqueous or organic solvent. The terms "pharmaceutically-acceptable aqueous solvent" and "pharmaceutically-acceptable organic solvent" refer to a solvent which is capable of having dissolved therein the anti-wrinkle oxaloacetate, and possesses acceptable safety properties (e.g., irritation and sensitization characteristics). One example of a suitable pharmaceutically acceptable aqueous solvent is distilled water. Examples of a suitable pharmaceutically acceptable organic solvent include, for example, monohydric alcohols, such as ethanol, and polyhydric alcohols, such as glycols. If the topical pharmaceutical and cosmetic compositions of the present disclosure are formulated as an aerosol and applied to the skin as a spray-on, a propellant is added to a solution composition.

In one embodiment, topical pharmaceutical and cosmetic compositions of the present invention further comprise a suitable amount of a topical pharmaceutical and cosmetically-acceptable emollient. As used herein, "emollients" refer to materials used for the prevention or relief of dryness, as well as for the protection of the skin. Wide varieties of suitable emollients are known and may be used herein. Sagarin, Cosmetics, Science and Technology, 2nd Edition, Vol. 1, pp. 32-43 (1972), contains numerous examples of suitable materials. Examples of classes of useful emollients include hydrocarbon oils and waxes such as mineral oil, petrolatum, paraffin, ceresin, ozokerite, microcrystalline wax, polyethylene, and perhydrosqualene; silicone oil, such as dimethyl polysiloxanes, methylphenyl polysiloxanes, and water-soluble and alcohol-soluble silicone glycol copolymers. Other suitable emollients include triglyceride esters such as vegetable and animal fats and oils including castor oil, safflower oil, cotton seed oil, corn oil, olive oil, cod liver oil, almond oil, avocado oil, palm oil, sesame oil, and soybean oil; acetoglyceride esters, such as acetylated monoglycerides; ethoxylated glycerides, such as ethoxylated glycerylmonostearate; alkyl esters of fatty acids including methyl, isopropyl, and butyl esters of fatty acids, alkyl esters including hexyl laurate, isohexyl laurate, iso-hexyl palmitate, isopropyl palmitate, decyl oleate, isodecyl oleate, hexadecyl stearate, decyl stearate, isopropyl isostearate, diisopropyl adipate, dissohexyl adipate, di-hexyldecyl adipate, di-isopropyl sebacate, lauryl lactate, myristyl lactate, and cetyl lactate; and alkenyl esters of fatty acids such as oleyl myristate, oleyl stearate, and oleyl oleate. Other suitable classes of emollients include fatty acids such as pelargonic, lauric, myristic, palmitic, stearic, isostearic, hydroxystearic, oleic, linoleic, ricinoleic, arachidic, behenic, and erucic acids.; fatty alcohols such as lauryl, myristyl, cetyl, hexadecyl, stearyl, isostearyl, hydroxystearyl, oleyl, ricinoleyl, behenyl, and erucyl alcohols, as well as 2-octyl dodecanol; fatty alcohol ethers; ethoxylated fatty alcohols; ether-esters such as fatty acid esters of ethoxylated fatty alcohols; lanolin and derivatives including lanolin oil, lanolin wax, lanolin alcohols, lanolin fatty acids, isopropyllanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysis of lanolin, ethoxylated hydrogenated lanolin, ethoxylated sorbitol lanolin, and liquid and semisolid lanolin absorption bases are illustrative of emollients derived from lanolin; polyhydric alcohols and polyether derivatives such as propylene glycol, dipropylene glycol, polypropylene glycols 2000 and 4000, polyoxyethylene polyoxypropylene glycols, polyoxypropylene polyoxyethylene glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol (2-methyl-2,4-pentanediol), 1,3-butylene glycol, 1,2,6-hexanetriol, ethohexadiol USP (2-ethyl,3-hexanediol), C15-C18 vicinal glycol, and polyoxypropylene derivatives of trimethylolpropane; polydydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylatedpropylene glycol monostearate, glyceryl mono- and di-fatty acid esters, polyglycerol poly-fatty acid esters, ethoxylated glyceryl monostearate, 1,3-butylene glycol-monostearate, 1,3-butylene glycol distearate, polyoxyethylene polyol fatty acid ester, sorbitan fatty acid esters, and polyoxyethylene sorbitan fatty acid esters; wax esters such as beeswax, spermaceti, myristyl myristate and stearyl stearate; beeswax derivatives, e.g., polyoxyethylene sorbitol beeswax; vegetable waxes including carnauba and candelilla waxes; and phospholipids, such as lecithin and derivatives; sterols including, for example, cholesterol and cholesterol fatty acid esters; amides such as fatty acid amides, ethoxylated fatty acid amides and solid fatty acid alkanolamides.

Particularly useful emollients which provide skin conditioning are glycerol, hexanetriol, butanetriol, lactic acid and its salts, urea, pyrrolidone carboxylic acid and its salts, amino acids, guanidine, diglycerol and triglycerol.

Alternatively, the composition can be formulated as a lotion. A lotion can be made from a solution carrier system. In some embodiments, the lotion includes from about 1% to about 20%, for example, from about 5% to about 10%, of an emollient; and from about 50% to about 90%, for example, from about 60% to about 80% of water.

Another type of product that may be formulated from a solution carrier system is a cream or ointment. An ointment can comprise a simple base of animal or vegetable oils or semi-solid hydrocarbons (oleaginous). Ointments can also include absorption ointment bases which absorb water to form emulsions. Optionally, the ointment carriers is water soluble. An ointment can include from about 2% to about 10% of an emollient plus from about 0.1% to about 2% of a thickening agent. Examples of suitable thickening agents include: cellulose derivatives (e.g., methyl cellulose and hydroxy propylmethylcellulose), synthetic high molecular weight polymers (e.g., carboxyvinyl polymer and polyvinyl alcohol), plant hydrocolloids (e.g., karaya gum and tragacanth gum), clay thickeners (e.g., colloidal magnesium aluminum silicate and bentonite), and carboxyvinyl polymers (CARBOPOLS®; sold by B. F. Goodrich Company, such polymers are described in detail in Brown, U.S. Pat. No. 2,798,053, issued Jul. 2, 1975). A more complete disclosure of thickening agents useful herein can be found in Sagarin, Cosmetics, Science and Technology, 2nd Edition, Vol. 1, pp. 72-73 (1972). If the carrier is formulated as an emulsion, from about 1% to about 10%, for instance, from about 2% to about 5%, of the carrier system comprises an emulsifier. Suitable emulsifiers include nonionic, anionic or cationic emulsifiers. Exemplary emulsifiers are disclosed in, for example, McCutcheon's Detergents and Emulsifiers, North American Edition, pages 317-324 (1986). Preferred emulsifiers are anionic or nonionic, although other types can also be employed.

Single emulsion skin care preparations, such as lotions and creams, of the oil-in-water type and water-in-oil type are well known in the cosmetic arts and are useful in the present embodiments. Multiphase emulsion compositions, such as the water-in-oil-in water type are also useful in the present embodiments. In general, such single or multiphase emulsions contain water, emollients and emulsifiers as essential ingredients. Triple emulsion carrier systems comprising an oil-in-water-in-silicone fluid emulsion composition are also useful in the present embodiments.

Another emulsion carrier system useful in the topical pharmaceutical and cosmetic compositions of the present disclosure is a microemulsion carrier system. Such a system preferably comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water. This carrier system is combined with the therapeutic agents described above.

If the topical pharmaceutical and cosmetic compositions of the present disclosure are formulated as a gel or a cosmetic stick, a suitable amount of a thickening agent, as disclosed supra, is added to a cream or lotion formulation. The topical pharmaceutical and cosmetic compositions of the present disclosure may also be formulated as makeup products such as foundations, blush, and lipstick and can contain conventional cosmetic adjuvants, such as dyes, opacifiers, pigments and perfumes. Foundations are solution or lotion-based with appropriate amounts of thickeners such as algin, xanthan gum, cellulose gum, cocamide DEA, guar gum lanolin alcohol, paraffin, and propylene glycol, pigments including ultramarine blue, titanium dioxide, and carmine, colorants such as FD&C Red No. 40 and FD&C Yellow No. 5, moisturizers, and fragrance. Optionally, the foundation can include a sunscreen agent. The topical pharmaceutical and cosmetic compositions of the present disclosure may contain, in addition to the aforementioned components, a wide variety of additional oil-soluble materials and/or water-soluble materials conventionally used in topical compositions, at their established levels. Various water-soluble materials may also be present in the compositions of this invention. These include humectants, such as glycerol, sorbitol, propylene glycol, alkoxylated glucose and hexanetriol, ethyl cellulose, polyvinylalcohol, carboxymethyl cellulose, vegetable gums and clays such as VEEGUM® (magnesium aluminum silicate, R. T. Vanderbilt, Inc.); proteins and polypeptides, preservatives such as the methyl, ethyl, propyl and butyl esters of hydroxybenzoic acid (Parabens®—Mallinckrodt Chemical Corporation), EDTA, methylisothiazolinone and imidazolidinyl ureas (Germall 115®—Sutton Laboratories); and an alkaline agent such as sodium hydroxide or potassium hydroxide to neutralize, if desired, part of the fatty acids or thickener which may be present.

In some embodiments, oxaloacetate can be formulated as a hair product such as a shampoo or conditioner. Use of these products would then have a dual benefit to the user including a reduction in skin aging and delay in the onset of age-related skin disease including cancer. Oxaloacetate, when applied topically to the hair, can also prevent or reduce hair loss and hair graying.

The topical pharmaceutical and cosmetic compositions of the present disclosure can also include a safe and effective amount of a penetration enhancing agent. Other conventional skin care product additives may also be included in the compositions of the present invention. For example, collagen, elastin, hydrolysates, primrose oil, jojoba oil, epidermal growth factor, soybean saponins, mucopolysaccharides, and mixtures thereof may be used. Various vitamins can also be included in the compositions of the present invention. For example, Vitamin A, and derivatives thereof, Vitamin B2, biotin, pantothenic, Vitamin D, and mixtures thereof can be used.

In some embodiments, the composition comprising oxaloacetate is incorporated into anti-wrinkle skin cleaning compositions. The skin cleaning compositions comprise a cosmetically acceptable surfactant in addition to oxaloacetate. The term "cosmetically-acceptable surfactant" refers to a surfactant that is not only an effective skin cleanser, but also can be used without undue toxicity, irritation, allergic response, and the like. Furthermore, the surfactant should be capable of being commingled with the anti-wrinkle components in a manner such that there is no interaction that would substantially reduce the efficacy of the composition for treating wrinkles in mammalian skin. In addition to the cosmetically effective amounts of the active ingredients, the skin cleaning compositions of the present disclosure contain from about 1% to about 90%, preferably from about 5% to about 10%, of a cosmetically-acceptable surfactant. The physical form of the skin cleansing compositions is not critical. The compositions can be, for example, formulated as toilet bars, liquids, pastes, or mousses. Toilet bars are most preferred since this is the form of cleansing agent most commonly used to wash the skin. The surfactant component of the disclosed compositions is selected from the group consisting of anionic, nonionic, zwitterionic, amphoteric and ampholytic surfactants, as well as mixtures of these surfactants. Such surfactants are well known to those skilled in the detergency art. The cleaning compositions of the present disclosure can optionally contain, at their art-established levels, materials which are conventionally used in skin cleansing compositions.

Other skin care products for the treatment of skin wrinkles may contain combinations of additional active ingredients. Such combinations include, for example, sunscreens and sunblocks. Optimum regulation of skin wrinkling resulting from exposure to U.V. light can be obtained by using a combination of oxaloacetate together with sunscreens or sunblocks. Useful sunblocks include, for example, zinc oxide and titanium dioxide. Photo damage is a predominant cause of skin wrinkling. Thus, for purposes of wrinkle prevention, the combination of the disclosed compositions with a UVA and/or UVB sunscreen would be most desirable. The inclusion of sunscreens in compositions of the present invention will provide immediate protection against acute UV damage. Thus, the sunscreen will prevent further wrinkle formation caused by UV radiation, while the anti-wrinkle agents treat existing wrinkles and skin atrophy, and enhances DNA repair in the cells of the skin.

A wide variety of conventional sunscreening agents are suitable for use in combination with the anti-wrinkle formulations. Sagarin, et al., at Chapter VII, pages 189 et seq., of Cosmetics Science and Technology, disclose numerous suitable agents. Specific suitable sunscreening agents include, for example: p-aminobenzoic acid, its salts and its derivatives (ethyl, iso-butyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropylene glycol esters); cinnamic acid derivatives (methyl and benzyl esters, .alpha.-phenyl cinnamonitrile; butyl cinnamoyl pyruvate); dihydroxycinnamic acid derivatives (umbelliferone, methyl umbelliferone, methylacetoumbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxynaphthoic acid and its salts; o- and p-hydroxybiphenyidisulfonates; (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); (butyl carbotol)(6-propyl piperonyl) ether; hydroquinone; benzophenones (oxybenzene, sulisobenzone, dioxybenzone, benzoresorcinol, 2,2',4,4'tetrahydroxy-benzophenone, 2,2'-dihydroxy-4,4'-dimethoxybenzophenone, octabenzone; 4-isopropyidibenzoyl-methane; butylmethoxy dibenzoylmethane; etocrylene; and 4-isopropyl-dibenzoyl-methane). Mixtures of sunscreen compounds may be used to optimize the desired sunscreen properties of the formulation. A safe and effective amount of sunscreen may be used in the compositions of the present invention. The sun-screening agent must be compatible with the anti-wrinkle agents. Generally the composition may comprise from about 1% to about 20%, preferably from about 2% to about 10%, of a sunscreening agent. Exact amounts will vary depending upon the sunscreen chosen and the desired Sun Protection Factor (SPF). An agent may also be added to any of the compositions of the present invention to improve the skin substantivity of those compositions, particularly to enhance their resistance to being washed off by water, or rubbed off.

In yet a further embodiment of the current invention, the oxaloacetate delivered topically can be mixed with a penetration enhancing agent such as dimethylsulfoxide (DMSO), combinations of sucrose fatty acid esters with a sulfoxide or phosphoric oxide, or eugenol, that allows faster migration of the oxaloacetate into the dermal tissues and then further into deeper cellular tissues, including cellulite tissues where stimulation of the Sirt1 gene will cause a reduction of fat tissues.

In one embodiment, the disclosed compounds are administered through a topical delivery system. Implantable or injectable polymer matrices, and transdennal formulations, from which active ingredients are slowly released are also well known and can be used in the disclosed methods. The controlled release components described above can be used as the means to delivery the disclosed compounds. The compositions can further include components adapted to improve the stability or effectiveness of the applied formulation, such as preservatives, antioxidants, skin penetration enhancers and sustained release materials. Examples of such components are described in the following reference works hereby incorporated by reference: *Martindale-The Extra Pharmacopoeia* (Pharmaceutical Press, London 1993) and Martin (ed.), *Remington's Pharmaceutical Sciences*.

Controlled release preparations can be achieved by the use of polymers to complex or absorb oxaloacetate. The controlled delivery can be exercised by selecting appropriate macromolecule such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active compound.

Hydrogels, wherein the oxaloacetate is dissolved in an aqueous constituent to gradually release over time, can be prepared by copolymerization of hydrophilic mono-olefinic monomers such as ethylene glycol methacrylate. Matrix devices, wherein the oxaloacetate is dispersed in a matrix of carrier material, can be used. The carrier can be porous, non-porous, solid, semi-solid, permeable or impermeable. Alternatively, a device comprising a central reservoir of the oxaloacetate compound surrounded by a rate controlling membrane can be used to control the release of oxaloacetate. Rate controlling membranes include ethylene-vinyl acetate copolymer or butylene terephthalate/polytetramethylene ether terephthalate. Use of silicon rubber depots are also contemplated.

In another embodiment, transdermal patches, steady state reservoirs sandwiched between an impervious backing and a membrane face, and transdermal formulations, can also be used to deliver oxaloacetate. Transdermal administration systems are well known in the art. Occlusive transdermal patches for the administration of an active agent to the skin or mucosa are described in U.S. Pat. Nos. 4,573,996, 4,597, 961 and 4,839,174, which are hereby incorporated by reference. One type of transdermal patch is a polymer matrix in which the active agent is dissolved in a polymer matrix through which the active ingredient diffuses to the skin. Such transdermal patches are disclosed in U.S. Pat. Nos. 4,839,174, 4,908,213 and 4,943,435, which are hereby incorporated by reference. In one embodiment, the steady state reservoir carries doses of oxaloacetate in doses from about 2 mg to 40 mg per day.

Present transdermal patch systems are designed to deliver smaller doses over longer periods of time, up to days and weeks. A rate-controlling outer microporous membrane, or micropockets of the disclosed oxaloacetate dispersed throughout a silicone polymer matrix, can be used to control the release rate. Such rate-controlling means are described in U.S. Pat. No. 5,676,969, which is hereby incorporated by reference. In another embodiment, the oxaloacetate is released from the patch into the skin of the patient in about 20-30 minutes or less.

These transdermal patches and formulations can be used with or without use of a penetration enhancer such as dimethylsulfoxide (DMSO), combinations of sucrose fatty acid esters with a sulfoxide or phosphoric oxide, or eugenol. The use of electrolytic transdermal patches is also within the scope of the methods disclosed herein. Electrolytic transdermal patches are described in U.S. Pat. Nos. 5,474,527, 5,336,168, and 5,328,454, the entire contents of which are hereby incorporated by reference.

Oxaloacetate may be formulated for parenteral administration by injection, e.g., by bolus injection or continuous infusion. The injected oxaloacetate can be mixed with other beneficial agents prior to injection including but not limited to antibiotics and other medications, saline solutions, blood plasma, and other fluids. Immediate contact of elevated levels of oxaloacetate with the vascular system cells will result in the reduction in age-related diseases such as hardening of the arteries, even if the amounts of oxaloacetate are insufficient to provide age-related benefits to the entire organism. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

Oxaloacetate may also be formulated in rectal compositions such as suppositories or retention enemas, e.g., containing conventional suppository bases such as cocoa butter or other glycerides.

In addition to the formulations described previously, oxaloacetate may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

In yet still another embodiment, oxaloacetate can be mixed with animal foods to increase the life span and general health of pets and other animals. Oxaloacetate can either be formulated as part of the animal food or administered separately as a supplement to the animal's food. As those skilled in the art know, dry pet foods, typically dry dog foods, normally contain protein, fat, fiber, non-fiber carbohydrates, minerals, vitamins and moisture components. For example, as major ingredients, there are typically one or two cereal grains, generally corn, wheat and/or rice. In addition, for a protein source they may contain poultry meal, by-product meat, meat and bone meal, or other animal or fish meal by-products. At times as well, grain protein supplements such as corn gluten, soybean meal or other oil seed meals can be added. In addition to an effective amount of oxaloacetate of between about 0.01% to 0.1% by weight of the chow, animal chow of the present invention additionally includes the following: typical nutrient content in the food dry matter includes crude protein from 14% to 50%, usually 20% to 25%; crude fat from 5% to 25%; and crude fiber usually is present in the range of from about 3% to 14%, usually about 5% to 7%, with the total mineral or ash content being within the range of 3% to 10%, usually 4% to 7%. The important point is not the precise formulation of the pet food, since many conventional and satisfactory ones for use in conjunction with the present invention are available on the market. Rather, the key to success is that a sufficient amount of oxaloacetate component be added to pet food rations, whichever formulation is used, to provide the oxaloacetate activity level at the ranges necessary to increase life span, reduce body weight, and treat age-related disorders.

EXAMPLES

Particular aspects herein can be more readily understood by reference to the following examples, which are intended to exemplify the teachings herein, without limiting their scope to the particular exemplified embodiments.

Example 1

The *Caenorhabditis elegans* nematode worm is commonly used as a test animal because its genetics are well understood and the basic cellular energy pathways are well conserved throughout all animal species, including hunans. A test with these well-understood worms on metabolic energy pathways is a test on the animal kingdom. The conservation of the energy pathways is a reason that CR has worked in all animal species tested.

*C. elegans* (N2 wild type, from Carolina Biological Supply) was used as a test organism to assess the addition of oxaloacetate therapy (from Sigma Aldrich Company) applied to the cells to extend lifespan and to act as a caloric restriction "mimic". The oxaloacetate was mixed in a concentration of 16 mM into the nematode growth agar (from Carolina Biological Supply Company) on eight experimental plates on which the *C. elegans* resides. A similar set of eight control plates with the same nematode growth agar was also prepared. Both the eight oxaloacetate plates and eight control plates included 80 μM of 5'flurodeoxyuridine (from Sigma Aldrich Company) to eliminate the development of eggs into live progeny. In addition, five "starter plates" were made using nematode growth agar and no 5'flurodeoxyuridine.

All plates were streaked with 0.5 ml bacteria Luria broth containing *E. coli* as a food source for the nematodes. The bacteria were allowed to grow on the plates for several days at 37° C. prior to adding *C. elegans*.

Ten *C. elegans* nematodes were transferred to each of five "starter plates" and were left on the plates for 12 hours to lay eggs. The *C. elegans* were then removed and the eggs were allowed to grow into young adults for two days. Ten nematodes were then transferred to each control plate and oxaloacetate plate by "picking" worms with a microprobe from the starter plate and moving it onto the target test plates.

Figure 2:
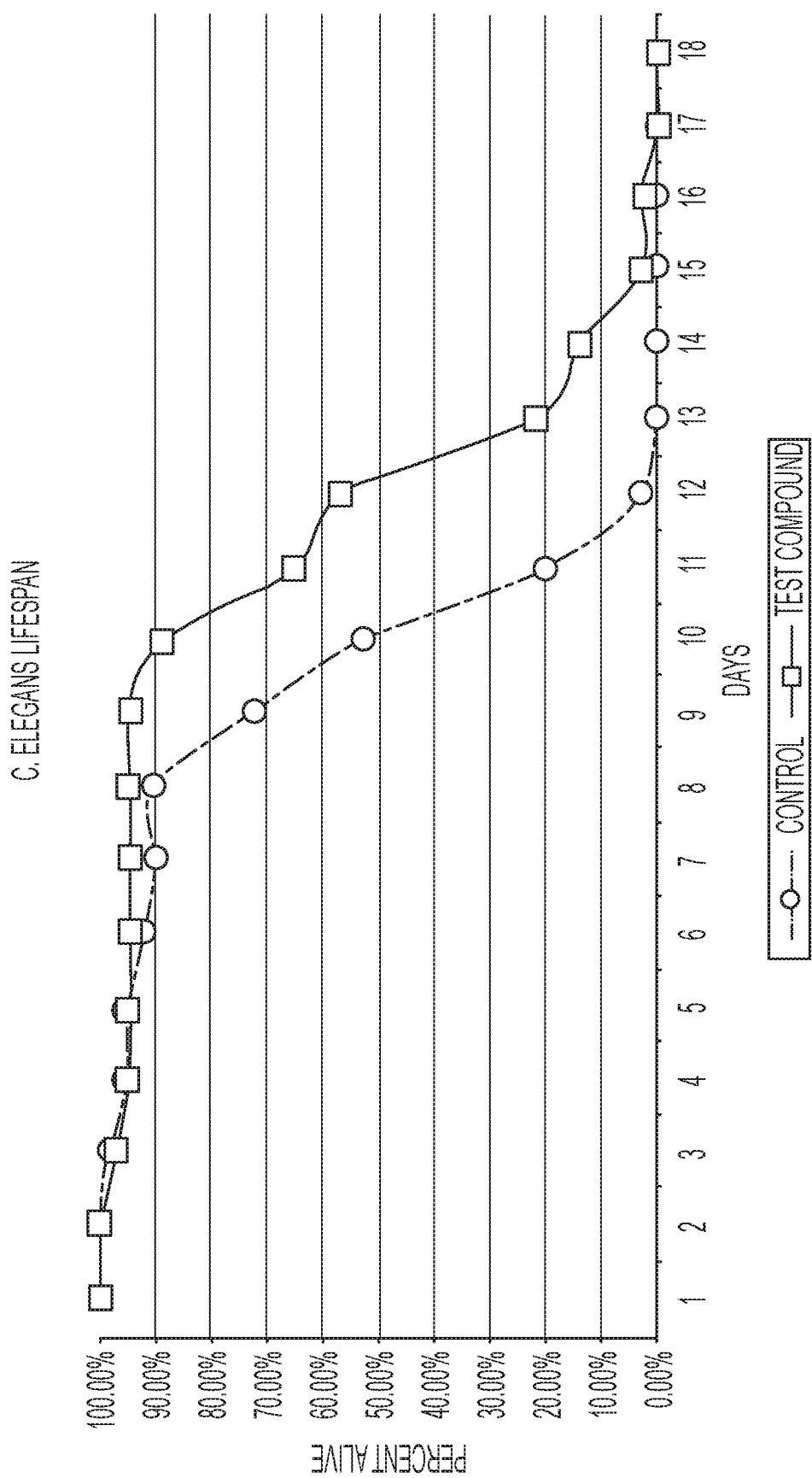
FIG. 2 is a graph illustrating the effect of oxaloacetate supplementation on extending the life span of the C. elegans nematode.

The day after the starter plates have been started with the 10 C. elegans was designated "day 0", and was the estimated time of birth. The C. elegans were kept out of direct sunlight and were raised at a temperature of 21° C. The plates with the C. elegans were counted every day to determine the number of dead nematodes. Nematodes were scored as dead when they no longer respond to a gentle prodding with a probe. Lifespan is defined as the time elapsed from when the nematodes are hatched (lifespan=0) to when they are scored as dead. Nematodes that crawl off the plates or are otherwise lost during the assay have been excluded from calculations. The dead nematodes were removed from the plates each day with microprobe. The total population is the sum of all found dead worms. The counting of the nematodes was continued until all nematodes were dead. The data was then charted and is represented in FIG. 2.

Data indicated an increase in average lifespan of 23.6% in the nematodes that lived on the oxaloacetate plates as opposed to the control group. Maximal life span was also increased in the oxaloacetate containing plates by 40%.

Example 2

The experiment in Example 1 was repeated for a range of oxaloacetate concentrations in the nematode growth agar. An increase in lifespan for C. elegans was seen at 2 mM oxaloacetate in the agar, and increased with 4 mM, 6 mM, 8 mM, 10 mM, 12 mM, 14 mM and 16 mM concentrations. The highest increase in lifespan was at 16 mM (approximate 25%) for the concentrations tested, and the lowest increase was a 2 mM (approximately 10%).

Example 3

Figure 3:
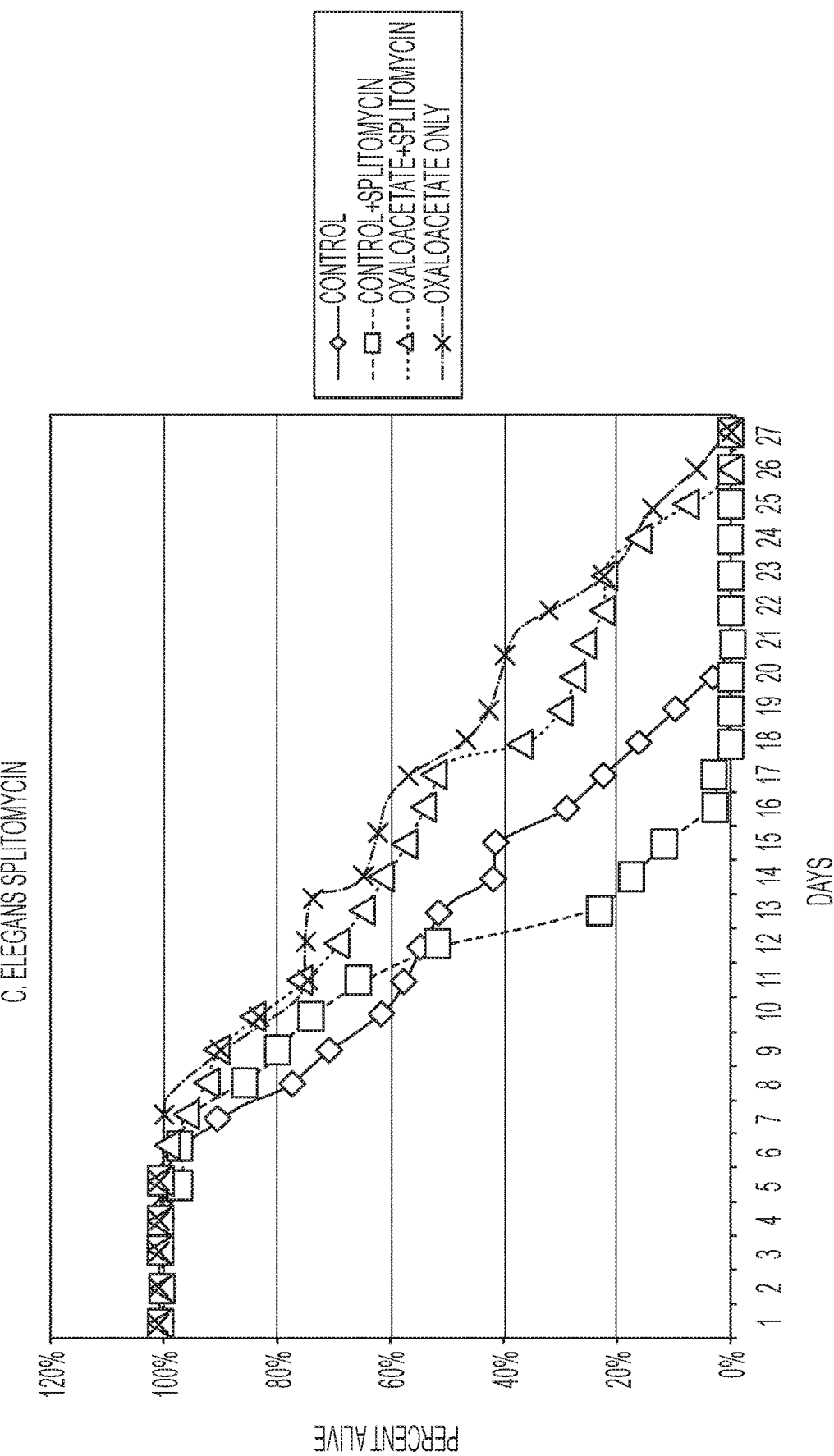
FIG. 3 is a graph illustrating the effect of Splitomycin (a selective Sir2 inhibitor) and oxaloacetate supplementation on the lifespan of the C. elegans nematode.

The experiment in Example 1 was repeated but additional plates containing splitomycin alone with the agar and splitomycin with oxaloacetate and the agar were also used. Splitomycin is a selective inhibitor for the Sir2 gene (Sir2a in yeast, Sirt1 in humnans). The nematodes on plates with inhibited Sir2 function but no oxaloacetate lived for shorter periods than the control group as reflected in FIG. 3. FIG. 3 illustrates that similar to CR, oxaloacetate upregulates the Silent Information Regulator gene (Sir2) to increase lifespan. It also shows that other beneficial CR activated genes are upregulated and downregulated by oxaloacetate to increase lifespan without Sir2 activation. Nematodes on plates with oxaloacetate lived approximately 36% longer than the control group. Nematodes on plates with inhibited Sir2 function but also included oxaloacetate had an increased lifespan above the control group of 15%. This demonstrates that Sir2 makes up approximately ⅓ of the lifespan increase in CR, while the other CR beneficial genes contribute to as much as ⅔ of the lifespan increase. It also demonstrates that one of the genes activated by oxaloacetate addition is Sir2 (Sir2a in yeast, Sirt1 in humans).

Example 4

The fruit fly *Drosophila melanogaster* (Vestigal type, from Carolina Biological Supply) was used as a test organism to assess the addition of oxaloacetate therapy (from Sigma Aldrich Company) applied to the cells to extend lifespan and to act as a caloric restriction "mimic". The fruit fly is more complex than C. elegans, but the metabolic pathways that involve calorie restriction are a basic building block of life, and are conserved throughout the animal kingdom. In the test group of 53 flies in four vials (2 virgin male, 2 virgin female), oxaloacetate was mixed in a concentration of 16 mM into the 15 ml of distilled water used to wet the 15 ml of dry fly food (from Carolina Biological Supply Company). A small amount of yeast was added on top of the fly food. A similar control group of 56 flies in 4 vials (2 virgin male, 2 virgin female) were also prepared, except that no Oxaloacetate was added.

The flies were kept in a room receiving reflected natural sunlight at a temperature of 21° C. Each of the flies used emerged from the pupae state within 8 hours of each other.

Figure 4:
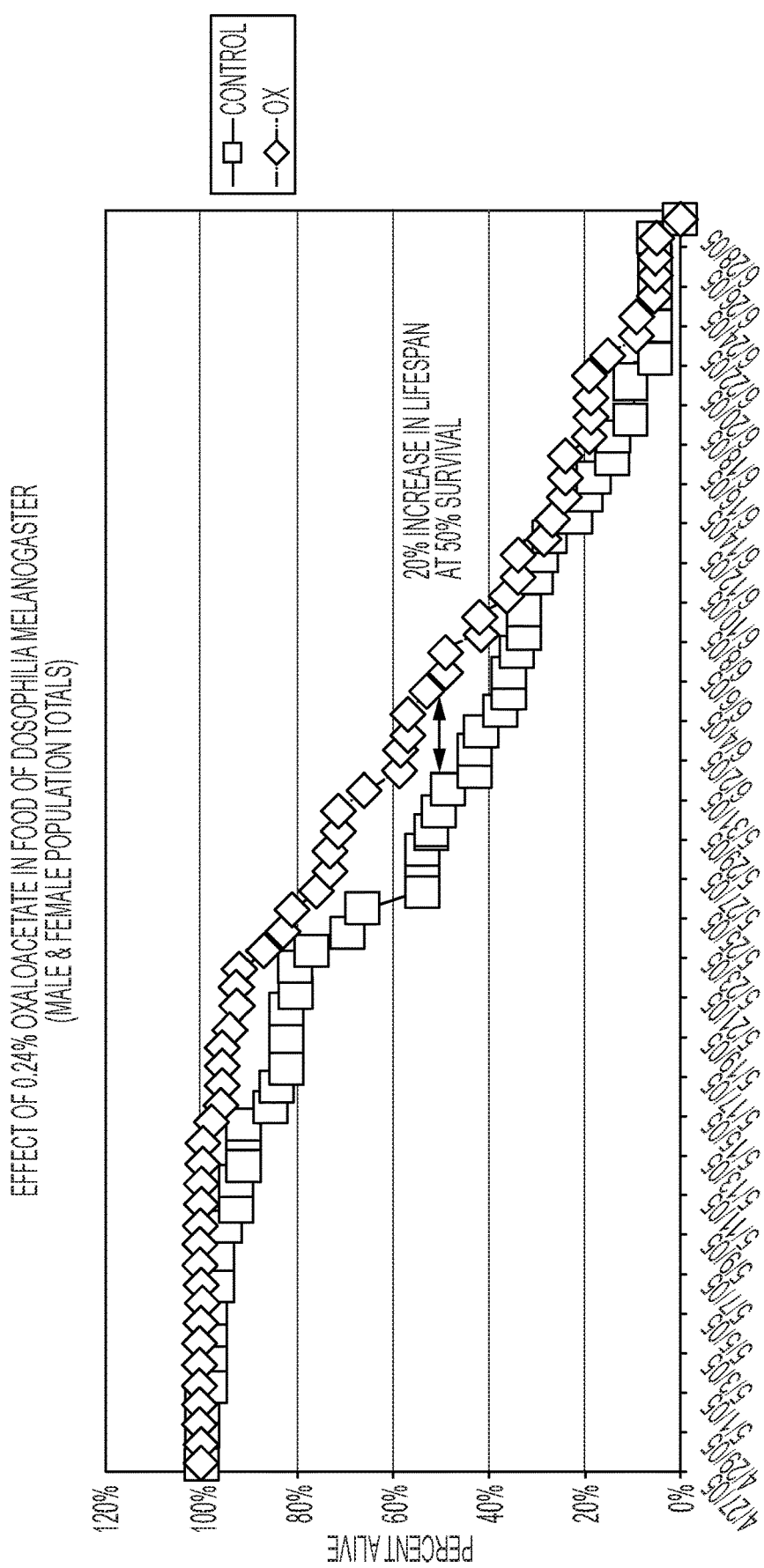
FIG. 4 is a graph illustrating the effect of oxaloacetate supplementation on extending the life span of the D. melanogaster fruit fly.

The day the flies were moved to the test vials was designated "day 0", reflecting the emergence of the fly into adulthood. The flies were kept out of direct sunlight and were raised at a temperature of 21° C. The food vials were prepared every 3 to 4 days and the flies transferred to prevent infestation of mites and other pathogenic microbial organisms. The vials with the flies were counted every day to determine the number of dead vs. living. Flies were scored as dead when they no longer respond to a gentle prodding with a probe. Lifespan is defined as the time elapsed from when the flies enter into adulthood (lifespan=0) to when they are scored as dead. Flies that were lost due to transfer between food vials or were otherwise lost during the assay have been excluded from calculations. The dead flies were removed from the vials each day with microprobe. The total population is the sum of all found dead flies. The counting of the flies was continued until all flies were dead. The data was then charted and is represented in FIG. 4.

Data indicated an increase in average lifespan of 20% in the flies that lived on the oxaloacetate supplemented vials as opposed to the control group.

Example 5

Figure 5:
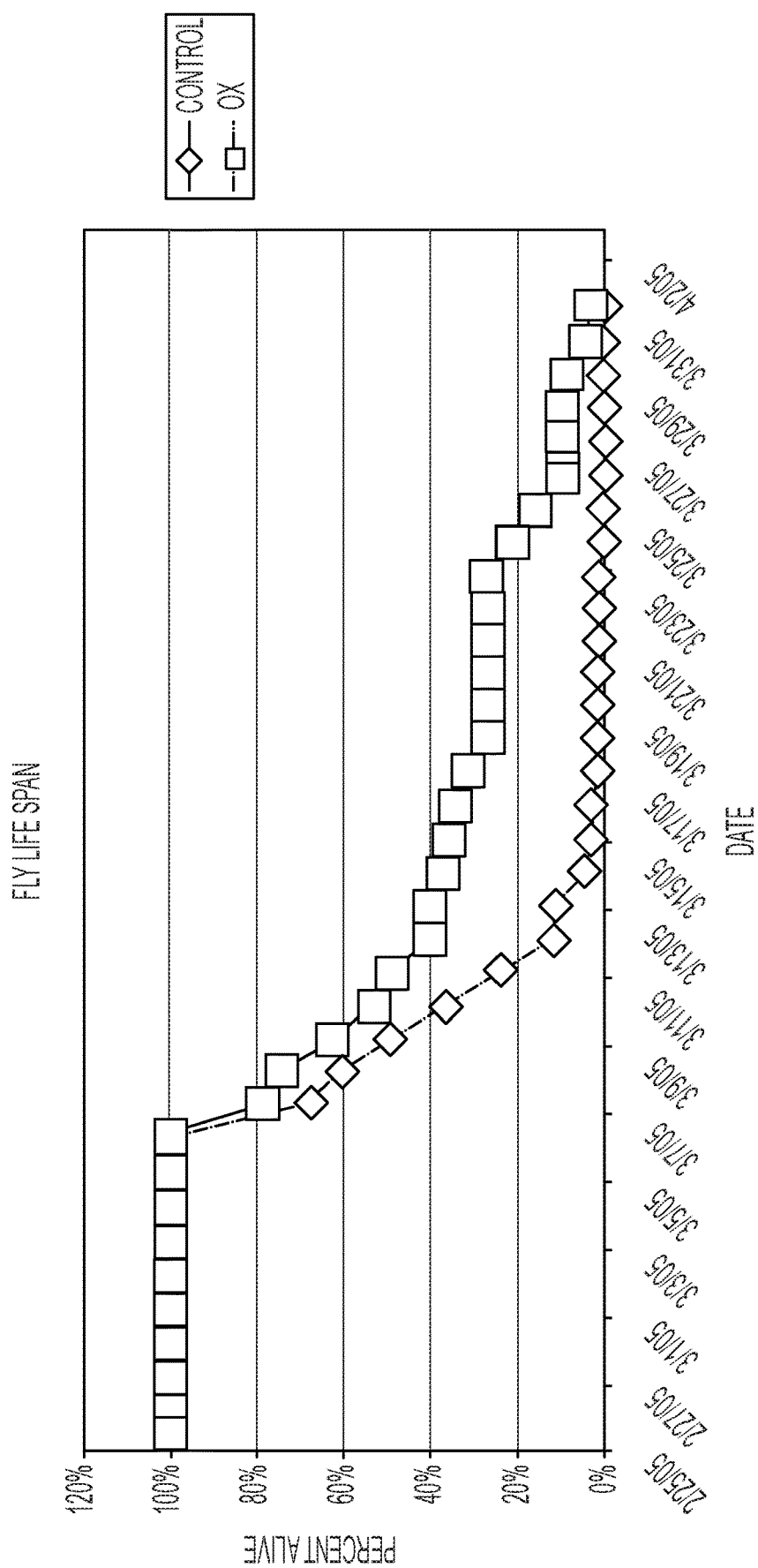
FIG. 5 is a graph illustrating the effect of oxaloacetate supplementation on extending the life span of the D. melanogaster fruit fly when the fly is placed under stress.

The experiment in Example 4 was repeated, except that the food vials were not changed out every 3 to 4 days and 71 flies were supplemented with oxaloacetate and 70 flies were not. This resulted in infestations of microbial pathogens that attacked the flies, placing the flies under "stress". It is well known in the literature that calorie restricted animals survive stress better than the control animals fed an ad libitum diet. The data from the experiment were charted and are represented in FIG. 5.

Data indicated an increase of both average lifespan under stress, and a maximal increase in lifespan of 30%. The oxaloacetate supplemented group lived significantly longer, indicating an improved resistance to stress (also found in calorie restricted animals).

Example 6

C57Bl/6 type male mice approximately 9 months of age were obtained from Harlan, San Diego, Calif. as retired breeders. These mice were all born on the same day. The C57Bl/6 type mouse is inbred to reduce the genetic variation between individuals. The mice were housed in individual cages and were provided with ad libitum amounts of fortified food pellets (Kadee). The amount of food consumed was weighed daily, while the mice were weighed weekly. After two weeks, a baseline of the average food consumed by the mice was established at 7.1 grams per mouse per day. In addition, after an overnight fast, blood glucose readings for each mouse were recorded for each mouse. At the two-week point the mice were grouped into three equivalent groups (based on initial weight and fasting blood glucose measurements) of I) eight "Control Mice" fed ad libitum; II) eight "Calorie Restricted" mice, initially fed 20% less than the control group for two weeks, then increased to being fed 40% less than the control group, and III) nine "oxaloacetate" supplemented mice that were fed an increasing dose of oxaloacetate in their food, but were allowed to eat freely.

Figure 6:
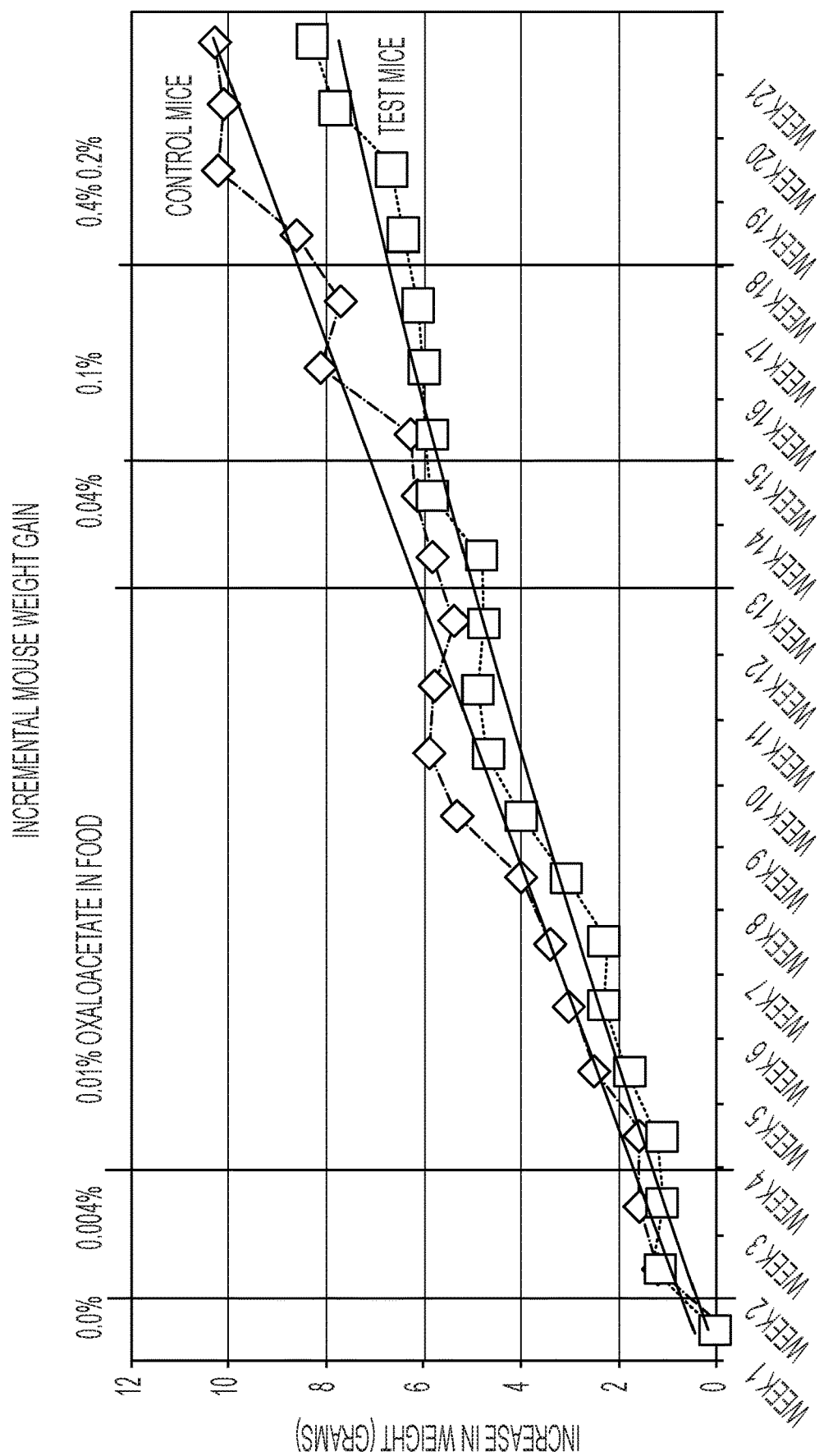
FIG. 6 is a graph illustrating the effect of oxaloacetate supplementation on the reduced weight gain of older C57Bl/6 type mice.

Male C57Bl/6 type mice, when allowed to eat freely, gain weight with age in a linear fashion. The mice were weighed weekly for 21 weeks, and the individual weights were recorded and averaged to form a "group average" for each of the three groups. The incremental increase in weight between the "Control" group and the "Oxaloacetate" supplemented group was charted as represented by FIG. 6. The data indicates that control mice increase in weight in a linear fashion, whereas oxaloacetate supplementation decreases the amount of body weight that mice will gain when eating freely. The larger the amount of supplementation of oxaloacetate, the larger the reduction in weight gain in a dose dependent fashion. At 0.4% oxaloacetate in the food, the oxaloacetate mice gained 20% less weight than the control group, even though both groups were allowed to eat freely.

The results of this experiment indicate that oxaloacetate supplementation can be used to reduce body weight in mammals.

Example 7

The experiment in Example 6 was repeated with one month old male mice (as compared to the nine month old mice used in Example 6). As in the previous Example 6, young C57Bl/6 type mice grouped by weight into three groups, I) Control; II) Calorie Restricted; and III) Oxaloacetate supplemented. Instead of slowly increasing the dose of oxaloacetate, however, the mice were subjected to a concentration of 0.4% oxaloacetate from the start of the experiment, and calorie restricted mice were immediately placed on a 40% restricted diet. The mice were weighed weekly, and the results were plotted as represented by FIG. 7.

Figure 7:
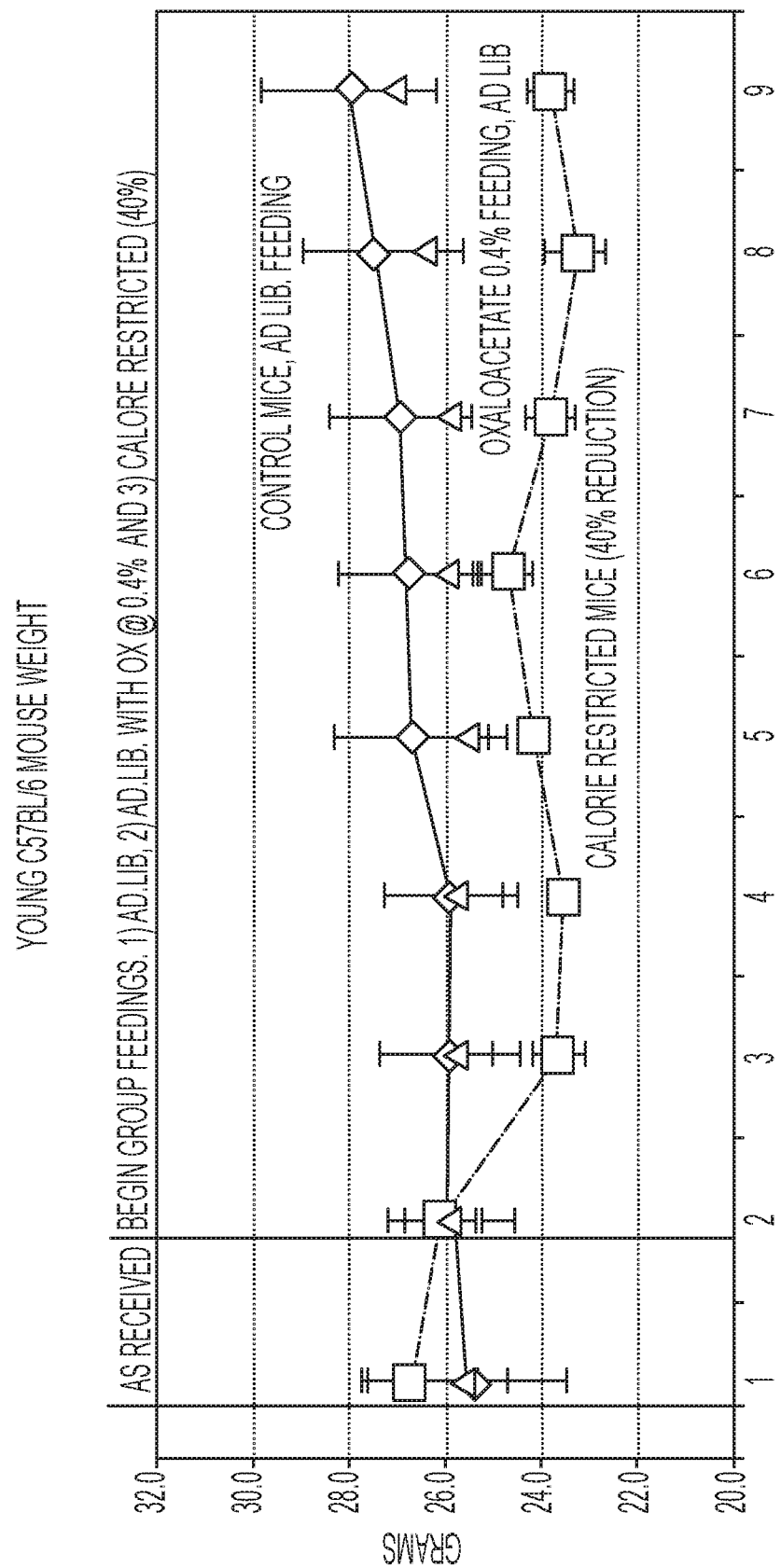
FIG. 7 is a graph illustrating the effect of oxaloacetate supplementation on the reduced weight gain of younger C57BL/6 type mice.

FIG. 7 shows that young mice also respond to oxaloacetate supplementation for reduced weight gain. Note that it took about three weeks for the effect of the oxaloacetate to fully be seen, after which point the weight differential remained constant due to the non-varying dosage.

Example 8

Figure 8:
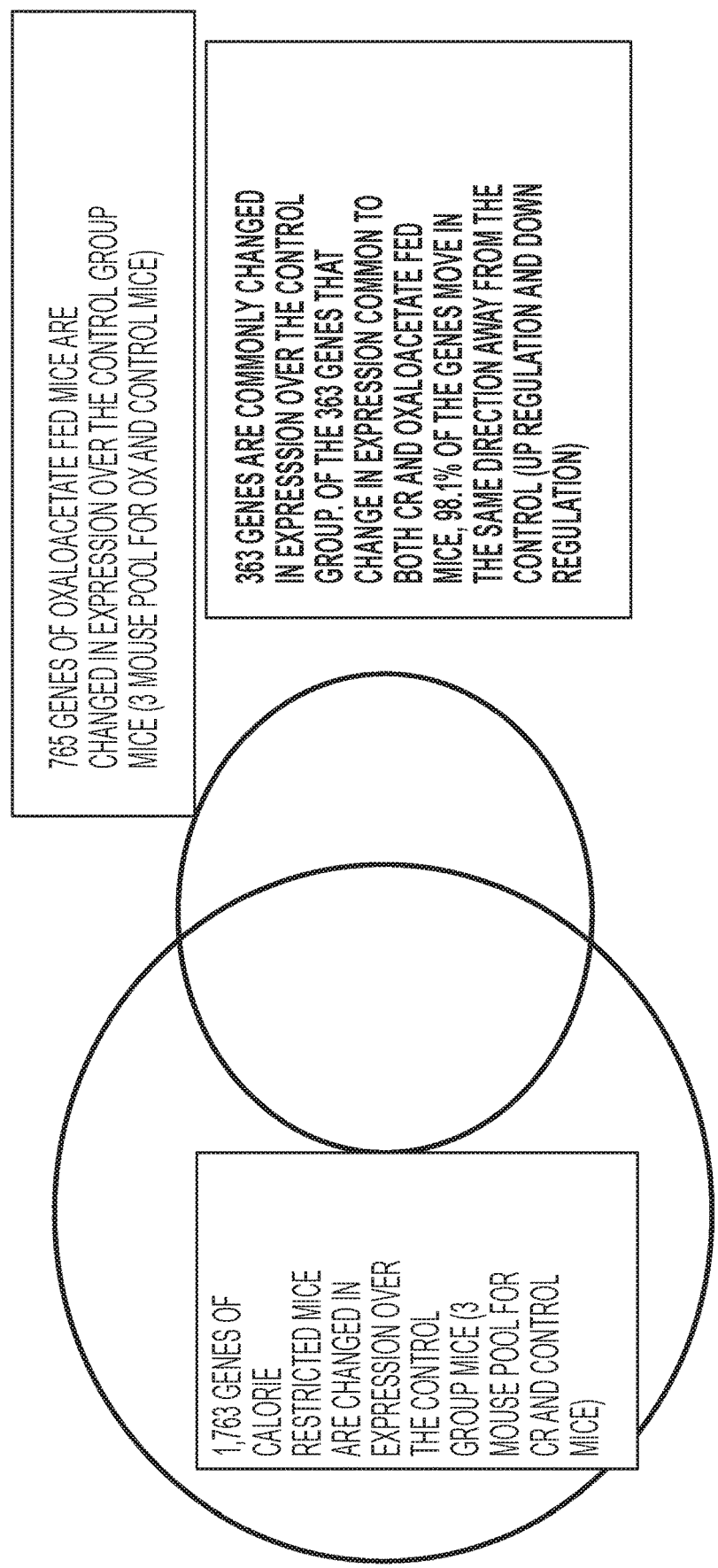
FIG. 8 is a graph illustrating the effect of oxaloacetate supplementation on extending the life span of C57Bl/6 type mice.

Three mice of each of the three groups of the C57Bl/6 mice of Example 6 were sacrificed after 21 weeks. The liver of each animal was extracted and each set of three mice was pooled and analyzed for gene activity as described by Cao et al. The gene expression of the pooled mice group was shown to change in response to supplementation with oxaloacetate and in a similar fashion to mice under CR, as compared to the control group of mice. The CR mice showed a measurable change in the expression of 1,763 genes, while the oxaloacetate mice showed a measurable change in 765. Because each group was a pooling of three mice, there are a variety of individual responses. Changes in the physical results of the group (such as weight loss, increase in health span, and increase in life span) are due to genes expressed in common by the group, not in individual variation. Thus it is important to look at the genes that changed in expression from the control group, but are commonly expressed between the calorie restricted group and the oxaloacetate supplemented group. There were 363 genes expressed in common between the oxaloacetate group and the calorie restricted group that changed in genomic expression when compared to the control group. A directional analysis of these 363 common genes indicated that 98% of the changed genes expressed in common between the oxaloacetate group of mice and the calorie restricted group of mice moved in the same direction (upregulated or down-regulated) as compared to the control group of mice. Thus, the supplementation of oxaloacetate mimicked the same genomic change in mice as did mice under calorie restriction, for 98% of the genes in common that changed expression from the control group. The oxaloacetate mice, however, did not have to restrict their diets, but ate freely. The 98% similarity in change between the oxaloacetate fed mice and the calorie restricted mice also ties to the fact that the oxaloacetate supplemented mice did not gain as much weight as the control mice (Example 6 and 7 above) and also live longer and are healthier (Example 9 below). Oxaloacetate supplementation mimics the same critical genomic response as calorie restriction (See FIG. 8). Effective doses of oxaloacetate fed to *C. elegans* and *D. melanogaster* increase lifespan by 20 to 36%, and minimum increase in lifespan of mice by 10%.

Example 9

The C57Bl/6 mice of Example 6 that were not sacrificed in Example 8 were continued to be fed as three separate groups, 1) Control, 2) Calorie Restricted and 3) Oxaloacetate supplemented (at a continuing dose of 0.4% in food by weight). It was noted that the Calorie Restricted group and the Oxaloacetate group was the healthiest group during the experiment, with a portion of the Control group being affected by inflammation characterized by intermittent bouts of itching and redness of the skin. The experiment is in continuation as this application for patent is filed, but initial indications are that the oxaloacetate group is living longer than the control group, and at least equal to the calorie restricted group.

Figure 9:
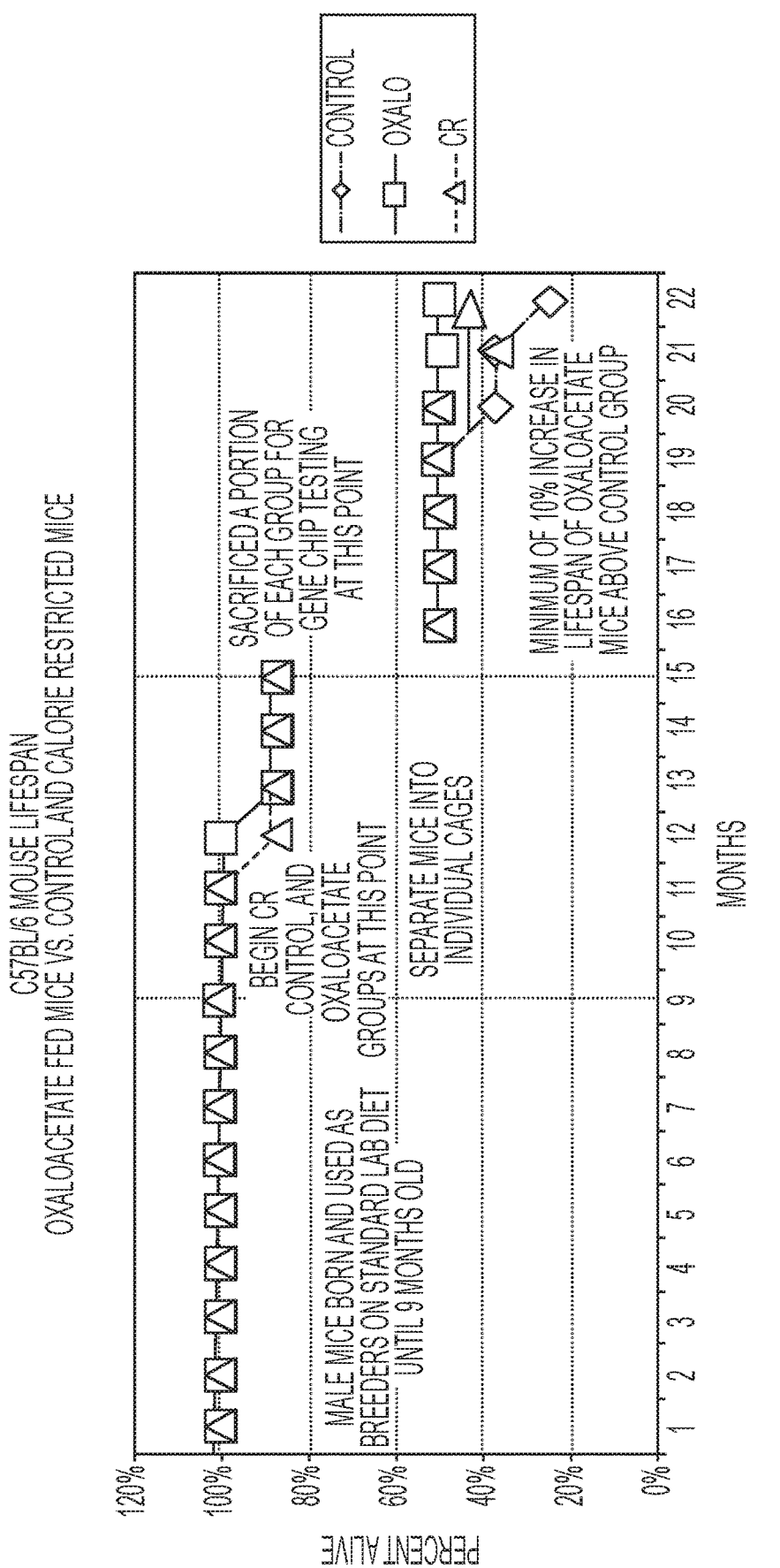
FIG. 9 is graph indicating the overlap between the change in gene expression between mice that are calorie restricted and mice that are supplemented with oxaloacetate versus a control group of mice fed ad libitum.

Lifespan data is represented by FIG. 9, which at the 21st month in their lives, oxaloacetate supplementation increased lifespan of the group by a minimum of 10% (and still continuing) over the control group, and at least equal to (or better) than the calorie restricted group.

Example 10

An obese individual weighing approximately 200 kg is identified. 1,000 mg of oxaloacetate is administered orally for a period of 30 days, taken every other day. The individual does not restrict calories. A reduction of body fat and body weight is observed following treatment.

Example 11

Individuals presenting with age related disorders including heart disease and osteoporosis are identified. Half of the individuals are administered an effective dose of approximately 7 mg of oxaloacetate per kg of body weight, taken every other day over a period of 30 days or more. The other half of the individuals are administered a placebo. Individuals receiving oxaloacetate demonstrate a reduction in symptoms associated with aging including a decrease in fasting glucose levels, fasting insulin levels, triglycerides, Hs-CRP levels, total cholesterol, LDL cholesterol, and systolic and diastolic blood pressure. Additionally, a reduction in the risk for atherosclerosis is also observed as compared with the untreated individuals.

Example 12

Two groups of individuals are exposed to UV radiation from the sun. One group applies an 8 mM concentration of oxaloacetate to the skin, while the control group does not. Both groups have their skin measured for unscheduled DNA synthesis (UDS), to measure the relative rate of DNA repair. The group with oxaloacetate has a significant increase in UDS over the control group.

Example 13

Two groups of individuals are diagnosed with similar types of cancer tumors. One group ingests a dose of 2,000 mg of oxaloacetate per day, whereas the control group does not. The oxaloacetate reduces the amount of glucose available to the tumor, which limits the growth of the tumor in a fashion similar to that seen in calorie restriction. The control group sees no limitation in tumor growth.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being redefined herein to be restricted to including any specific characteristics of the features or aspects of the invention with which that terminology is associated. The scope of the invention should therefore be construed in accordance with the appended claims and any equivalents thereof. Additionally, throughout this application, various publications have been referenced. The disclosures in these publications are incorporated herein by reference in order to more fully describe the state of the art.

What is claimed is:

1. A method for treating Alzheimer's disease comprising administering to a subject in need thereof a composition comprising a compound selected from the group consisting of oxaloacetate, oxaloacetic acid, and an oxaloacetate salt, and wherein the compound is administered at a dose of about 0.5 mg/kg to about 75 mg/kg.

2. The method of claim 1, wherein said composition is administered orally.

3. The method of claim 1, further comprising administering a therapeutic agent to the subject.

4. The method of claim 3, wherein the therapeutic agent is an antibacterial, an antifungal, a chemotherapeutic agent, an anti-histamine, protein, enzyme, vitamin, hormone, non-steroidal anti-inflammatory, an immune-stimulatory compound, or a steroid.

5. The method of claim 1, wherein said subject is a mammal.

6. The method of claim 5, wherein said mammal is a human.

7. The method of claim 1, wherein the compound is administered at a dose of about 2 mg/kg to about 40 mg/kg.

8. The methods of claim 1, wherein the compound is in a capsule.

9. The methods of claim 8, wherein the capsule is a hydroxypropyl methylcellulose capsule.

* * * * *